(12) United States Patent
Son et al.

(10) Patent No.: US 7,319,001 B2
(45) Date of Patent: Jan. 15, 2008

(54) HIGH THROUGHPUT SYSTEM FOR PRODUCING RECOMBINANT VIRUSES USING SITE-SPECIFIC RECOMBINATION

(75) Inventors: Ho-Sun Son, Seoul (KR); Do-Hui Kim, Busan (KR); Neon-C Jung, Seoul (KR); Eun-Wook Choi, Seoul (KR); Dong-Seung Seen, Seoul (KR); Min-Sung Kim, Gyeonggi-do (KR); Yong-Weon Yi, Daejeon (KR); Kyung-Jin Kim, Seoul (KR)

(73) Assignee: Neurogenex Co., Ltd., Seoul (KR)

( * ) Notice: Subject to any disclaimer, the term of this patent is extended or adjusted under 35 U.S.C. 154(b) by 415 days.

(21) Appl. No.: 10/383,838

(22) Filed: Mar. 7, 2003

(65) Prior Publication Data

US 2004/0185565 A1    Sep. 23, 2004

(30) Foreign Application Priority Data

Mar. 9, 2002    (KR) ............... 10-2002-0012634

(51) Int. Cl.
| | |
|---|---|
| C12N 15/10 | (2006.01) |
| C12N 15/63 | (2006.01) |
| C12N 15/64 | (2006.01) |
| C12N 15/866 | (2006.01) |
| C12N 15/86 | (2006.01) |
| A61K 48/00 | (2006.01) |

(52) U.S. Cl. ..................... 435/5; 435/6; 435/91.1; 435/91.4; 435/91.5; 435/455

(58) Field of Classification Search ............... None
See application file for complete search history.

(56) References Cited

U.S. PATENT DOCUMENTS

| | | | | |
|---|---|---|---|---|
| 5,348,886 A | * | 9/1994 | Lee et al. .................. 435/69.1 |
| 6,406,863 B1 | * | 6/2002 | Zhu et al. .................. 435/7.1 |
| 2004/0203016 A1 | * | 10/2004 | Elledge et al. ............ 435/6 |

FOREIGN PATENT DOCUMENTS

| | | |
|---|---|---|
| EP | 0 453 242 B1 | 10/1991 |
| WO | WO 95/02697 | 1/1995 |
| WO | WO 99/08692 | 2/1999 |

OTHER PUBLICATIONS

Kitts et al. Nuc. Acids Res. 1990; 18:5667-72.*
Parks, Robin J., et al. "A helper-dependent adenovirus vector system: Removal of helper virus by Cre-mediated excision of the viral packaging signal," *Proc. Nat'l. Acad. Sci. USA*, Nov. 1996, pp. 13565-13570, vol. 93, Applied Biological Sciences, USA.
Patience, Clive, et al. "Packaging of Endogenous Retroviral Sequences in Retroviral Vectors Produced by Murine and Human Packaging Cells," *Journal of Virology*, Apr. 1998, pp. 2671-2676, vol. 72, No. 4, American Society for Microbiology, USA.
Peakman, Timothy C., et al. "Highly efficient generation of recombinant baculoviruses by enzymatically mediated site-specific in vitro recombination," *Nucleic Acids Research*, pp. 495-500, vol. 20, No. 3, Oxford University Press, United Kingdom, 1992.
Powell, Sharon K., et al. "Efficacy of Antiretroviral Agents against Murine Replication-Competent Retrovirus Infection in Human Cells," *Journal of Virology*, Oct. 1999, pp. 8813-8816, vol. 73, No. 10, American Society for Microbiology, USA.
Shenk, Thomas. "Adenoviridae: The Viruses and Their Replication," *Fields Virology*, Third Edition, 1996, pp. 2111-2148, Lippincott-Raven Publishers, Philadelphia, USA.
Smith, Gale E., et al. "Production of Human Beta Interferon in Insect Cells Infected with a Baculovirus Expression Vector," *Molecular and Cellular Biology*, Dec. 1983, pp. 2156-2165, vol. 3, No. 12, American Society for Microbiology, USA.
Van Der Vliet, Peter C., et al. "Thermolabile DNA Binding Proteins from Cells Infected with a Temperature-Sensitive Mutant of Adenovirus Defective in Viral DNA Synthesis," *Journal of Virology*, Feb. 1975, pp. 348-354, vol. 15, No. 2, American Society for Microbiology, USA.
Wang, Yibin, et al. "Adenovirus technology for gene manipulation and functional studies," *Drug Discovery Today*, Jan. 2000, pp. 10-16, vol. 5, No. 1, Elsevier Science Ltd., USA.
Yang, Wei, et al. "Site-specific recombination in plane view," *Structure*, Nov. 15, 1997, pp. 1401-1406, vol. 5, Nat'l Institute of Diabetes and Digestive and Kidney Diseases, NIH, Bethesda, USA.

* cited by examiner

*Primary Examiner*—David Guzo
(74) *Attorney, Agent, or Firm*—Blakely, Sokoloff, Taylor & Zafman; Stephen M. De Klerk

(57) ABSTRACT

Disclosed are the methods for producing recombinant viruses using site-specific recombination in vitro. In the present invention, circular viral genomic DNAs are digested with restriction enzymes to generate a linear form viral genomic DNAs flanked by site-specific recombination sites, and then are subjected to site-specific recombination with the desired genomic materials flanked by site-specific recombination sites in vitro. According to the present invention, since the site-specific recombination mixture can be applied to host cells without further procedures of selecting the desired recombinant viral genomic DNAs, it is possible to obtain numerous recombinant viruses rapidly at the same time. Thus, the present invention can be used as a high throughput system for generating and screening hundreds or thousands of recombinant viruses.

9 Claims, 29 Drawing Sheets

(A)

M: λ HindIII size marker
1: BacPAK6
2: BacPAK6 (Bsu36I)
3: LacZ
4: LacZ (Bsu36I)
5: BacHTS
6: BacHTS (Bsu36I)
7: HGST-HTS
8: HGST-HTS (Bsu36I)
9: GFP-HTS
10: GFP-HTS

FIG. 16 (B) and (C)
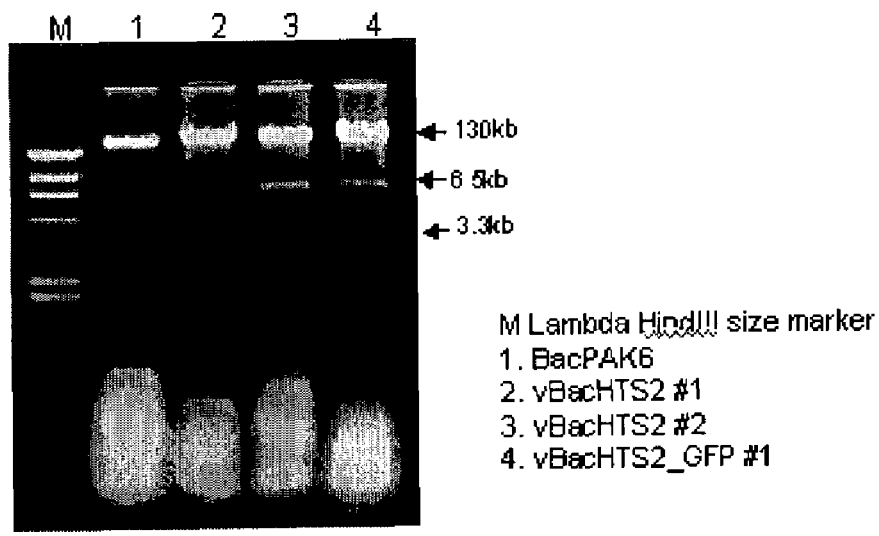
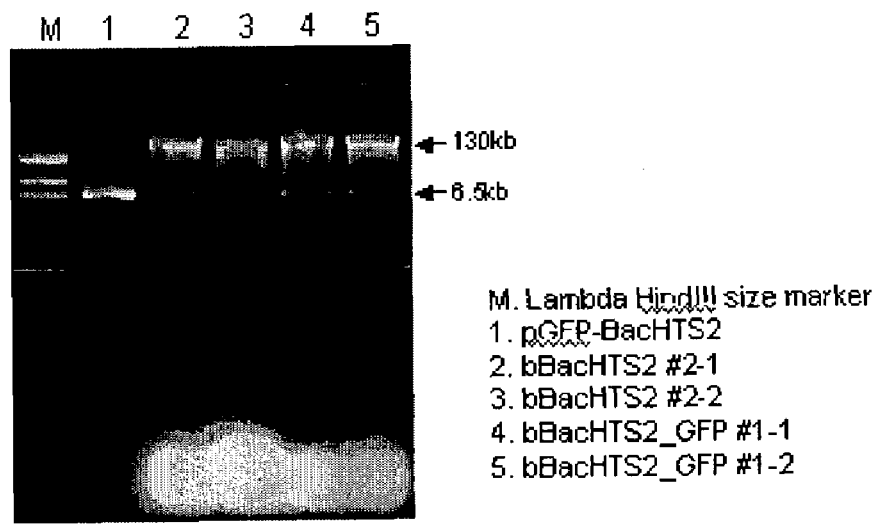

GFP expression in Sf21
48hr after transfection

GUS expression

GFP plaque

Gus plaque

GFP image      Anti-GFP western

FIG.23
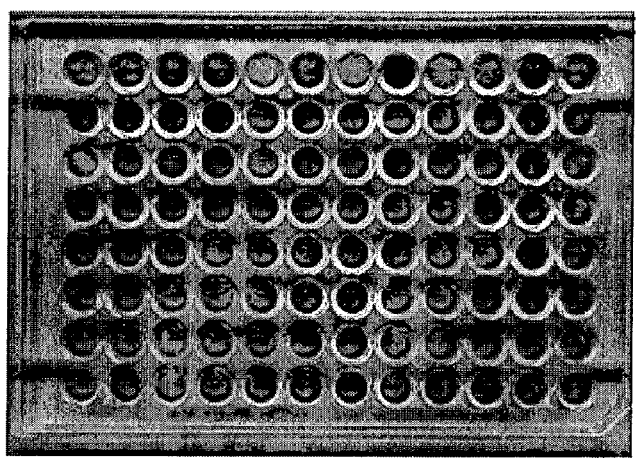
Recombinant GUS baculovirus
FIG.24
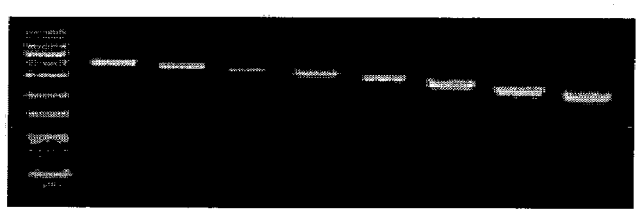
FIG.25

SEQUENCE LISTING

<160> NUMBER OF SEQ ID NOS: 9

<210> SEQ ID NO 1
<211> LENGTH: 10000
<212> TYPE: DNA
<213> ORGANISM: Artificial Sequence
<220> FEATURE:
<223> OTHER INFORMATION: Polyhedrin locus of vBacHTS virus
<220> FEATURE:

-continued

```
<221> NAME/KEY: promoter
<222> LOCATION: (4428)..(4520)
<223> OTHER INFORMATION: F pPolyhedrin
<220> FEATURE:
<221> NAME/KEY: misc_feature
<222> LOCATION: (4084)..(5109)
<223> OTHER INFORMATION: F ccdB
<220> FEATURE:
<221> NAME/KEY: misc_feature
<222> LOCATION: (5126)..(5250)
<223> OTHER INFORMATION: R attR2
<220> FEATURE:
<221> NAME/KEY: misc_feature
<222> LOCATION: (4537)..(4661)
<223> OTHER INFORMATION: F attR1

<400> SEQUENCE: 1
```

| | | | | | |
|---|---|---|---|---|---|
| gaattctacc | cgtaaagcga | gtttagtttt | gaaaaacaaa | tgacatcatt | tgtataatga | 60 |
| catcatcccc | tgattgtgtt | ttacaagtag | aattctatcc | gtaaagcgag | ttcagttttg | 120 |
| aaaacaaatg | agtcatacct | aaacacgtta | ataatcttct | gatatcagct | tatgactcaa | 180 |
| gttatgagcc | gtgtgcaaaa | catgagataa | gtttatgaca | tcatccactg | atcgtgcgtt | 240 |
| acaagtagaa | ttctactcgt | aaagccagtt | cggttatgag | ccgtgtgcaa | acatgacat | 300 |
| cagcttatga | ctcatacttg | attgtgtttt | acgcgtagaa | ttctactcgt | aaagcgagtt | 360 |
| cggttatgag | ccgtgtgcaa | acatgacat | cagcttatga | gtcataatta | atcgtgcgtt | 420 |
| acaagtagaa | ttctactcgt | aaagcgagtt | gaaggatcat | atttagttgc | gtttatgaga | 480 |
| taagattgaa | agcacgtgta | aaatgtttcc | cgcgcgttgg | cacaactatt | tacaatgcgg | 540 |
| ccaagttata | aaagattcta | atctgatatg | ttttaaaaca | cctttgcggc | ccgagttgtt | 600 |
| tgcgtacgtg | actagcgaag | aagatgtgtg | gaccgcagaa | cagatagtaa | aacaaaaccc | 660 |
| tagtattgga | gcaataatcg | atttaaccaa | cacgtctaaa | tattatgatg | gtgtgcattt | 720 |
| tttgcgggcg | ggcctgttat | acaaaaaaat | tcaagtacct | ggccagactt | tgccgcctga | 780 |
| aagcatagtt | caagaattta | ttgacacggt | aaaagaattt | acagaaaagt | gtcccggcat | 840 |
| gttggtgggc | gtgcactgca | cacacggtat | taatcgcacc | ggttacatgg | tgtgcagata | 900 |
| tttaatgcac | accctgggta | ttgcgccgca | ggaagccata | gatagattcg | aaaaagccag | 960 |
| aggtcacaaa | attgaaagac | aaaattacgt | tcaagattta | ttaatttaat | taatattatt | 1020 |
| tgcattcttt | aacaaatact | ttatcctatt | ttcaaattgt | tgcgcttctt | ccagcgaacc | 1080 |
| aaaactatgc | ttcgcttgct | ccgtttagct | tgtagccgat | cagtggcgtt | gttccaatcg | 1140 |
| acggtaggat | taggccggat | attctccacc | acaatgttgg | caacgttgat | gttacgttta | 1200 |
| tgcttttggt | tttccacgta | cgtcttttgg | ccggtaatag | ccgtaaacgt | agtgccgtcg | 1260 |
| cgcgtcacgc | acaacaccgg | atgtttgcgc | ttgtccgcgg | ggtattgaac | cgcgcgatcc | 1320 |
| gacaaatcca | ccactttggc | aactaaatcg | gtgacctgcg | cgtctttttt | ctgcattatt | 1380 |
| tcgtctttct | tttgcatggt | ttcctggaag | ccggtgtaca | tgcggtttag | atcagtcatg | 1440 |
| acgcgcgtga | cctgcaaatc | tttggcctcg | atctgcttgt | ccttgatggc | aacgatgcgt | 1500 |
| tcaataaact | cttgtttttt | aacaagttcc | tcggtttttt | gcgccaccac | cgcttgcagc | 1560 |
| gcgtttgtgt | gctcggtgaa | tgtcgcaatc | agcttagtca | ccaactgttt | gctctcctcc | 1620 |
| tcccgttgtt | tgatcgcggg | atcgtacttg | ccggtgcaga | gcacttgagg | aattacttct | 1680 |
| tctaaaagcc | attcttgtaa | ttctatggcg | taaggcaatt | ggacttcat | aatcagctga | 1740 |
| atcacgccgg | atttagtaat | gagcactgta | tgccggctga | aatacagcgg | gtcgccccctt | 1800 |
| ttcacgacgc | tgttagaggt | agggccccca | ttttggatgg | tctgctcaaa | taacgatttg | 1860 |

-continued

```
tatttattgt ctacatgaac acgtatagct ttatcacaaa ctgtatattt taaactgtta    1920
gcgacgtcct tggccacgaa ccggacctgt tggtcgcgct ctagcacgta ccgcaggttg    1980
aacgtatctt ctccaaattt aaattctcca attttaacgc gagccatttt gatacacgtg    2040
tgtcgatttt gcaacaacta ttgtttttta acgcaaacta aacttattgt ggtaagcaat    2100
aattaaatat gggggaacat gcgccgctac aacactcgtc gttatgaacg cagacggcgc    2160
cggtctcggc gcaagcggct aaaacgtgtt gcgcgttcaa cgcggcaaac atcgcaaaag    2220
ccaatagtac agttttgatt tgcatattaa cggcgatttt ttaaattatc ttatttaata    2280
aatagttatg acgcctacaa ctccccgccc gcgttgactc gctgcacctc gagcagttcg    2340
ttgacgcctt cctccgtgtg gccgaacacg tcgagcgggt ggtcgatgac cagcggcgtg    2400
ccgcacgcga cgcacaagta tctgtacacc gaatgatcgt cgggcgaagg cacgtcggcc    2460
tccaagtggc aatattggca aattcgaaaa tatatacagt tgggttgttt gcgcatatct    2520
atcgtggcgt tgggcatgta cgtccgaacg ttgatttgca tgcaagccga aattaaatca    2580
ttgcgattag tgcgattaaa acgttgtaca tcctcgcttt taatcatgcc gtcgattaaa    2640
tcgcgcaatc gagtcaagtg atcaaagtgt ggaataatgt tttctttgta ttcccgagtc    2700
aagcgcagcg cgtattttaa caaactagcc atcttgtaag ttagtttcat ttaatgcaac    2760
tttatccaat aatatattat gtatcgcacg tcaagaatta acaatgcgcc cgttgtcgca    2820
tctcaacacg actatgatag agatcaaata aagcgcgaat taaatagctt gcgacgcaac    2880
gtgcacgatc tgtgcacgcg ttccggcacg agctttgatt gtaataagtt tttacgaagc    2940
gatgacatga cccccgtagt gacaacgatc acgcccaaaa gaactgccga ctacaaaatt    3000
accgagtatg tcggtgacgt taaaactatt aagccatcca atcgaccgtt agtcgaatca    3060
ggaccgctgg tgcgagaagc cgcgaagtat ggcgaatgca tcgtataacg tgtggagtcc    3120
gctcattaga gcgtcatgtt tagacaagaa agctacatat ttaattgatc ccgatgattt    3180
tattgataaa ttgaccctaa ctccatacac ggtattctac aatggcgggg ttttggtcaa    3240
aatttccgga ctgcgattgt acatgctgtt aacggctccg cccactatta atgaaattaa    3300
aaattccaat tttaaaaaac gcagcaagag aaacatttgt atgaaagaat gcgtagaagg    3360
aaagaaaaat gtcgtcgaca tgctgaacaa caagattaat atgcctccgt gtataaaaaa    3420
aatattgaac gatttgaaag aaaacaatgt accgcgcggc ggtatgtaca ggaagaggtt    3480
tatactaaac tgttacattg caaacgtggt ttcgtgtgcc aagtgtgaaa accgatgttt    3540
aatcaaggct ctgacgcatt tctacaacca cgactccaag tgtgtgggtg aagtcatgca    3600
tcttttaatc aaatcccaag atgtgtataa accaccaaac tgccaaaaaa tgaaaactgt    3660
cgacaagctc tgtccgtttg ctggcaactg caagggtctc aatcctatttt gtaattattg    3720
aataataaaa caattataaa tgctaaattt gttttttatt aacgatacaa accaaacgca    3780
acaagaacat ttgtagtatt atctataatt gaaaacgcgt agttataatc gctgaggtaa    3840
tatttaaaat cattttcaaa tgattcacag ttaatttgcg acaatataat tttattttca    3900
cataaactag acgccttgtc gtcttcttct tcgtattcct tctctttttc attttctcc     3960
tcataaaaat taacatagtt attatcgtat ccatatatgt atctatcgta tagagtaaat    4020
ttttgttgt cataaatata tatgtctttt ttaatggggt gtatagtacc gctgcgcata    4080
gtttttctgt aatttacaac agtgctattt tctggtagtt cttcggagtg tgttgctttta    4140
attattaaat ttatataatc aatgaatttg ggatcgtcgg ttttgtacaa tatgttgccg    4200
```

-continued

```
gcatagtacg cagcttcttc tagttcaatt acaccatttt ttagcagcac cggattaaca      4260
taactttcca aaatgttgta cgaaccgtta aacaaaaaca gttcacctcc cttttctata      4320
ctattgtctg cgagcagttg tttgttgtta aaaataacag ccattgtaat gagacgcaca      4380
aactaatatc acaaactgga aatgtctatc aatatatagt tgctgatatc atggagataa      4440
ttaaaatgat aaccatctcg caaataaata agtattttac tgttttcgta acagttttgt      4500
aataaaaaaa cctataaata cggatcccgg ggtaccacaa gtttgtacaa aaaagctgaa      4560
cgagaaacgt aaaatgatat aaatatcaat atattaaatt agattttgca taaaaaacag      4620
actacataat actgtaaaac acaacatatc cagtcactat ggcggccgca ttaggcaccc      4680
cttaggaatt cgcttactaa aagccagata acagtatgcg tatttgcgcg ctgattttg       4740 cggtataaga atatatactg atatgtatac ccgaagtatg tcaaaaagag gtgtgcttct      4800
agaatgcagt ttaaggttta cacctataaa agagagagcc gttatcgtct gtttgtggat      4860
gtacagagtg atattattga cacgcccggg cgacggatgg tgatcccct ggccagtgca       4920 cgtctgctgt cagataaagt ctcccgtgaa ctttacccgg tggtgcatat cggggatgaa      4980
agctggcgca tgatgaccac cgatatggcc agtgtgccgg tctccgttat cggggaagaa      5040
gtggctgatc tcagccaccg cgaaaatgac atcaaaaacg ccattaacct gatgttctgg      5100
ggaatataga attcctcagg tcgaccatag tgactggata tgttgtgttt acagtatta      5160 tgtagtctgt tttttatgca aaatctaatt taatatattg atatttatat cattttacgt      5220
ttctcgttca gctttcttgt acaaagtggt ctcgagttaa ttaattgatc cgggttatta     5280
gtacatttat taagcgctag attctgtgcg ttgttgattt acagacaatt gttgtacgta      5340
ttttaataat tcattaaatt tataatcttt agggtggtat gttagagcga aaatcaaatg      5400
attttcagcg tctttatatc tgaatttaaa tattaaatcc tcaatagatt tgtaaaatag      5460
gtttcgatta gtttcaaaca agggttgttt ttccgaaccg atggctggac tatctaatgg      5520
attttcgctc aacgccacaa aacttgccaa atcttgtagc agcaatctag ctttgtcgat      5580
attcgtttgt gttttgtttt gtaataaagg ttcgacgtcg ttcaaaatat tatgcgcttt      5640
tgtatttctt tcatcactgt cgttagtgta caattgactc gacgtaaaca cgttaaataa      5700
agcttggaca tatttaacat cgggcgtgtt agctttatta ggccgattat cgtcgtcgtc      5760
ccaaccctcg tcgttagaag ttgcttccga agacgatttt gccatagcca cacgacgcct      5820
attaattgtg tcggctaaca cgtccgcgat caaatttgta gttgagcttt ttggaattat      5880
ttctgattgc gggcgttttt gggcgggttt caatctaact gtgcccgatt ttaattcaga      5940
caacacgtta gaaagcgatg gtgcaggcgg tggtaacatt tcagacggca aatctactaa      6000
tggcggcggt ggtggagctg atgataaatc taccatcggt ggaggcgcag gcggggctgg      6060
cggcggaggc ggaggcggag gtggtggcgg tgatgcagac ggcggtttag gctcaaatgt      6120
ctctttaggc aacacagtcg gcacctcaac tattgtactg gtttcgggcg ccgttttgg       6180 tttgaccggt ctgagacgag tgcgattttt ttcgtttcta atagcttcca acaattgttg      6240
tctgtcgtct aaaggtgcag cggggttgagg ttccgtcggc attggtggag cgggcggcaa      6300
ttcagacatc gatggtggtg gtggtggtgg aggcgctgga atgttaggca cgggagaagg      6360 tggtggcgg ggtgccgccg gtataatttg ttctggttta gtttgttcgc gcacgattgt       6420
gggcaccggc gcaggcgccg ctggctgcac aacggaaggt cgtctgcttc gaggcagcgc      6480 ttgggggtggt ggcaattcaa tattataatt ggaatacaaa tcgtaaaaat ctgctataag      6540
cattgtaatt tcgctatcgt ttaccgtgcc gatatttaac aaccgctcaa tgtaagcaat      6600
```

```
tgtattgtaa agagattgtc tcaagctcgg atcccgcacg ccgataacaa gccttttcat    6660
ttttactaca gcattgtagt ggcgagacac ttcgctgtcg tcgacgtaca tgtatgcttt    6720
gttgtcaaaa acgtcgttgg caagctttaa aatatttaaa agaacatctc tgttcagcac    6780
cactgtgttg tcgtaaatgt tgttttgat aatttgcgct tccgcagtat cgacacgttc    6840
aaaaaattga tgcgcatcaa ttttgttgtt cctattattg aataaataag attgtacaga    6900
ttcatatcta cgattcgtca tggccaccac aaatgctacg ctgcaaacgc tggtacaatt    6960
ttacgaaaac tgcaaaaacg tcaaaactcg gtataaaata tcaacgggc gctttggcaa    7020 aatatctatt ttatcgcaca agcccactag caaattgtat ttgcagaaaa caatttcggc    7080
gcacaatttt aacgctgacg aaataaaagt tcaccagtta atgagcgacc acccaaattt    7140
tataaaaatc tattttaatc acggttccat caacaaccaa gtgatcgtga tggactacat    7200
tgactgtccc gatttatttg aaacactaca aattaaaggc gagctttcgt accaacttgt    7260
tagcaatatt attagacagc tgtgtgaagc gctcaacgat ttgcacaagc acaatttcat    7320
acacaacgac ataaaactcg aaaatgtctt atatttcgaa gcacttgatc gcgtgtatgt    7380
ttgcgattac ggattgtgca aacacgaaaa ctcacttagc gtgcacgacg gcacgttgga    7440
gtattttagt ccggaaaaaa ttcgacacac aactatgcac gtttcgtttg actggtacgc    7500
cgtcggcgtg ttaacataca agttgctaac cggcggccga cacccatttg aaaaaagcga    7560
agacgaaatg ttggacttga atagcatgaa gcgtcgtcag caatacaatg acattggcgt    7620
tttaaaacac gttcgtaacg ttaacgctcg tgactttgtg tactgcctaa caagatacaa    7680
catagattgt agactcacaa attacaaaca aattataaaa catgagtttt tgtcgtaaaa    7740
atgccacttg ttttacgagt agaattctac gtgtaacaca cgatctaaaa gatgatgtca    7800 tttttttatca atgactcatt tgttttaaaa cagacttgtt ttacgagtag aattctacgt    7860
gtaaagcatg atcgtgagtg gtgttaataa aatcataaaa attattgtaa atgtttatta    7920
tttaaaaacg attcaaatat ataataaaaa caatctacat ctatttcttc acaatccata    7980
acacacaaca ggtccatcaa tgagtttttg tctttatccg acatactatg tgcatgtaac    8040
aaatcaaata catcttttaa attttatac acatctttac attgtctacc aaaatcttta    8100 ataccctat aacaaggaaa agacttttct tcttgcgtgg ttttgccgcg cagatattga    8160
aataaaatgt gcatgcacga caacttgtgt ttactaaaat gctccttgcc tataccgcaa    8220
aaccggccat acatttcggc gattacacgc ggacaattgt acgattcgtc tacgtgtaaa    8280
cgatcatcat aatcactctt gcgcaaacga ataaattttt tcaccgcttc cgacaaacga    8340
ggcaccaatt cggcgggcac gcttcgatac attattctgt gcacataagt taccacacaa    8400
aatttattgt accaccatcc gacaacgtcg ttattagggt tgaacacgtt ggcgatgcgc    8460
agcagtttcc cgtttctcat gaaatattca aagcggccca aaataatttg caagcaatcc    8520
aacatgtctt gagaaatttc tcgttcaaaa ttgttcaaag agaatatctg ccatccgttt    8580
tgaacgcgca cgctgacggg aaccaccgca tcgatttgct ccaacacttc acggacgtta    8640
tcgtcgatgc ccatcgtttc gctggtgctg aaccaatggg aaaggctctt gatggaatcg    8700
cccgcgtcta tcatcttgac cgcttcgtca aaggtgcaac tgccgctctt caaacgccgc    8760
atagcggtca cgtcccgctc tatgcacgac ataccgttta cgtacgattc tgataggtat    8820
tcctgaacta tacggtaatg gtgatacgac tcgccataca cgtcgtgcac ctcattgtat    8880
ttagcataat aattgtaaat tattaacttt gcagcgagag acatgttgtc agtaaagcgg    8940
```

```
tgctaggctc aataatactg atgtacaggc acgcgtgcta tttatatata atttcgcaag    9000 gagggagct gttatcggtt gctattatta aagaatggcc gtctgttttt atcacaagct    9060
tggcagcctc aaccatgaag cgtcgtcatt gtaaattaaa ttctctgcct caagaattat    9120
ttgacaagat tgtcgagtat ttatctttat ctgattactg caatttggtg cttgtctgta    9180
aaagaccttc tagtaaatat aacgtgatat ttgatagtac taatcaccaa catttgaaag    9240
gcgtgtacaa aaagacagac gtgcaaataa caagctacaa cgaatacatc aactgtattt    9300
gcaacgaact gagacaagac gaattctatg ccaaatcatc atggattgcg agtatttgcg    9360
gtcaccagag agcgacaatt tttagtgtaa caaataaaca gtagaaatg aaatatcatt    9420 tgtataatat agcaattgtg gaaagtgaag attgcaacgg attttaccca tttgagccaa    9480
cgcgcgattg tttaatatgc aaacaaaaaa accaatgtcc tcgtaattca tttattgttt    9540
cgttgtgtaa atatttagaa aaacaaaatg tacaatcaaa ctttatatat tatttatacg    9600
aaataaatac ataataataa ctattataca tgttttattt ttacaatact tcctgtataa    9660
cctctctaac tacattagga gtacaatcca cgtcaattac acgtttagct atttttctaa    9720
ttttgtaatg tttatcgtag agtttttcgt taatacattg aatagccaac aagggatttg    9780
ggtgcacacc gtcatagagt acttccatgt cgtcttcaaa gcgcattttt cgcttgcgaa    9840
aatgccgctc ttggcccaaa acaaaagcga gtttgatgcg gtcgtcgatg cgttccgaaa    9900
atacggccaa atgctggtgt tggtgatgt cgcgcggaaa cgtcaccgtg ccattttgc     9960 tttccgccac gacggcggtt ttcaatttt cggccgactg                         10000

<210> SEQ ID NO 2
<211> LENGTH: 10000
<212> TYPE: DNA
<213> ORGANISM: Artificial Sequence
<220> FEATURE:
<223> OTHER INFORMATION: Polyhedrin locus of vBacHTS_His
<220> FEATURE:
<221> NAME/KEY: source
<222> LOCATION: (4523)..(4553)
<223> OTHER INFORMATION: F 6His
<220> FEATURE:
<221> NAME/KEY: misc_feature
<222> LOCATION: (4831)..(5136)
<223> OTHER INFORMATION: F ccdB
<220> FEATURE:
<221> NAME/KEY: promoter
<222> LOCATION: (4428)..(4520)
<223> OTHER INFORMATION: F pPolyhedrin
<220> FEATURE:
<221> NAME/KEY: misc_feature
<222> LOCATION: (5153)..(5277)
<223> OTHER INFORMATION: R attR2
<220> FEATURE:
<221> NAME/KEY: misc_feature
<222> LOCATION: (4564)..(4688)
<223> OTHER INFORMATION: F attR1

<400> SEQUENCE: 2
gaattctacc cgtaaagcga gtttagtttt gaaaacaaa tgacatcatt tgtataatga      60
catcatcccc tgattgtgtt ttacaagtag aattctatcc gtaaagcgag ttcagttttg    120
aaaacaaatg agtcatacct aaacacgtta ataatcttct gatatcagct tatgactcaa    180
gttatgagcc gtgtgcaaaa catgagataa gtttatgaca tcatccactg atcgtgcgtt    240
acaagtagaa ttctactcgt aaagccagtt cggttatgag ccgtgtgcaa acatgacat    300 cagcttatga ctcatacttg attgtgtttt acgcgtagaa ttctactcgt aaagcgagtt    360
cggttatgag ccgtgtgcaa acatgacat cagcttatga gtcataatta atcgtgcgtt    420
```

-continued

```
acaagtagaa ttctactcgt aaagcgagtt gaaggatcat atttagttgc gtttatgaga    480
taagattgaa agcacgtgta aaatgtttcc cgcgcgttgg cacaactatt tacaatgcgg    540
ccaagttata aagattcta atctgatatg ttttaaaaca cctttgcggc ccgagttgtt     600
tgcgtacgtg actagcgaag aagatgtgtg gaccgcagaa cagatagtaa aacaaaaccc    660
tagtattgga gcaataatcg atttaaccaa cacgtctaaa tattatgatg gtgtgcattt    720
tttgcgggcg ggcctgttat acaaaaaaat tcaagtacct ggccagactt tgccgcctga    780
aagcatagtt caagaattta ttgacacggt aaaagaattt acagaaaagt gtcccggcat    840
gttggtgggc gtgcactgca cacacggtat taatcgcacc ggttacatgg tgtgcagata    900
tttaatgcac accctgggta ttgcgccgca ggaagccata gatagattcg aaaaagccag    960
aggtcacaaa attgaaagac aaaattacgt tcaagattta ttaatttaat taatattatt   1020
tgcattcttt aacaaatact ttatcctatt ttcaaattgt tgcgcttctt ccagcgaacc   1080
aaaactatgc ttcgcttgct ccgtttagct tgtagccgat cagtggcgtt gttccaatcg   1140
acggtaggat taggccggat attctccacc acaatgttgg caacgttgat gttacgttta   1200
tgcttttggt tttccacgta cgtctttttgg ccggtaatag ccgtaaacgt agtgccgtcg   1260
cgcgtcacgc acaacaccgg atgtttcgc ttgtccgcgg ggtattgaac cgcgcgatcc    1320
gacaaatcca ccactttggc aactaaatcg gtgacctgcg cgtctttttt ctgcattatt   1380
tcgtctttct tttgcatggt ttcctggaag ccggtgtaca tgcggtttag atcagtcatg   1440
acgcgcgtga cctgcaaatc tttggcctcg atctgcttgt ccttgatggc aacgatgcgt   1500
tcaataaact cttgtttttt aacaagttcc tcggttttttt gcgccaccac cgcttgcagc   1560
gcgtttgtgt gctcggtgaa tgtcgcaatc agcttagtca ccaactgttt gctctcctcc   1620
tcccgttgtt tgatcgcggg atcgtacttg ccggtgcaga gcacttgagg aattacttct   1680
tctaaaagcc attcttgtaa ttctatggcg taaggcaatt tggacttcat aatcagctga   1740
atcacgccgg atttagtaat gagcactgta tgcggctgca aatacagcgg gtcgcccctt   1800
ttcacgacgt tgttagaggt agggccccca ttttggatgg tctgctcaaa taacgatttg   1860
tatttattgt ctacatgaac acgtatagct ttatcacaaa ctgtatattt taaactgtta   1920
gcgacgtcct tggccacgaa ccggaccttg tggtcgcgct ctagcacgta ccgcaggttg    1980
aacgtatctt ctccaaattt aaattctcca attttaacgc gagccatttt gatacacgtg   2040
tgtcgatttt gcaacaacta ttgttttta acgcaaacta aacttattgt ggtaagcaat    2100
aattaaatat gggggaacat gcgccgctac aacactcgtc gttatgaacg cagacggcgc   2160
cggtctcggc gcaagcggct aaaacgtgtt gcgcgttcaa cgcggcaaac atcgcaaaag   2220
ccaatagtac agttttgatt tgcatattaa cggcgatttt ttaaattatc ttatttaata   2280
aatagttatg acgcctacaa ctccccgccc gcgttgactc gctgcacctc gagcagttcg   2340
ttgacgcctt cctccgtgtg gccgaacacg tcgagcgggt ggtcgatgac cagcggcgtg   2400
ccgcacgcga cgcacaagta tctgtacacc gaatgatcgt cgggcgaagg cacgtcggcc   2460
tccaagtggc aatattggca aattcgaaaa tatatacagt tgggttgttt gcgcatatct   2520
atcgtggcgt tgggcatgta cgtccgaacg ttgatttgca tgcaagccga aattaaatca   2580
ttgcgattag tgcgattaaa acgttgtaca tcctcgcttt aatcatgcc gtcgattaaa    2640 tcgcgcaatc gagtcaagtg atcaaagtgt ggaataatgt tttctttgta ttcccgagtc   2700
aagcgcagcg cgtattttaa caaactagcc atcttgtaag ttagtttcat ttaatgcaac   2760
```

-continued

```
tttatccaat aatatattat gtatcgcacg tcaagaatta acaatgcgcc cgttgtcgca      2820
tctcaacacg actatgatag agatcaaata aagcgcgaat aaatagcttt gcgacgcaac      2880
gtgcacgatc tgtgcacgcg ttccggcacg agctttgatt gtaataagtt tttacgaagc      2940
gatgacatga cccccgtagt gacaacgatc acgcccaaaa gaactgccga ctacaaaatt      3000
accgagtatg tcggtgacgt taaaactatt aagccatcca atcgaccgtt agtcgaatca      3060
ggaccgctgg tgcgagaagc cgcgaagtat ggcgaatgca tcgtataacg tgtggagtcc      3120
gctcattaga gcgtcatgtt tagacaagaa agctacatat ttaattgatc ccgatgattt      3180
tattgataaa ttgaccctaa ctccatacac ggtattctac aatggcgggg ttttggtcaa      3240
aatttccgga ctgcgattgt acatgctgtt aacggctccg cccactatta atgaaattaa      3300
aaattccaat tttaaaaaac gcagcaagag aaacatttgt atgaaagaat gcgtagaagg      3360
aaagaaaaat gtcgtcgaca tgctgaacaa caagattaat atgcctccgt gtataaaaaa      3420
aatattgaac gatttgaaag aaaacaatgt accgcgcggc ggtatgtaca ggaagagg tt      3480 tatactaaac tgttacattg caaacgtggt ttcgtgtgcc aagtgtgaaa accgatgttt      3540
aatcaaggct ctgacgcatt tctacaacca cgactccaag tgtgtgggtg aagtcatgca      3600
tcttttaatc aaatcccaag atgtgtataa accaccaaac tgccaaaaaa tgaaaactgt      3660
cgacaagctc tgtccgtttg ctggcaactg caagggtctc aatcctattt gtaattattg      3720
aataataaaa caattataaa tgctaaatt t gttttttatt aacgatacaa accaaacgca      3780
acaagaacat ttgtagtatt atctataatt gaaaacgcgt agtttataatc gctgaggtaa      3840 tatttaaaat cattttcaaa tgattcacag ttaatttgcg acaatataat tttatttcca      3900
cataaactag acgccttgtc gtcttcttct tcgtattcct tctcttttt c attttctcc      3960 tcataaaaat taacatagtt attatcgtat ccatatatgt atctatcgta tagagtaaat      4020 ttttttgttgt cataaatata tatgtctttt ttaatgggt gtatagtacc gctgcgcata      4080 gttttt ctgt aatttacaac agtgctattt tctggtagtt cttcggagtg tgttgcttta      4140
attattaaat ttatataatc aatgaatttg ggatcgtcgg ttttgtacaa tatgttgccg      4200
gcatagtacg cagcttcttc tagttcaatt acaccatttt ttagcagcac cggattaaca      4260
taactttcca aaatgttgta cgaaccgtta acaaaaaca gttcacctcc ctttt ctata      4320 ctattgtctg cgagcagttg tttgttgtta aaaataacag ccattgtaat gagacgcaca      4380
aactaatatc acaaactgga aatgtctatc aatatatagt tgctgatatc atggagataa      4440
ttaaaatgat aaccatctcg caaataaata agtatttta c tgttttcgta acagttttgt      4500
aataaaaaaa cctataaata cggatctatg catcatcacc atcatcacgg atcccgggt      4560 accacaagtt tgtacaaaaa agctgaacga gaaacgtaaa atgatataaa tatcaatata      4620
ttaaattaga ttttgcataa aaaacagact acataatact gtaaaacaca acatatccag      4680
tcactatggc ggccgcatta ggcaccccct aggaattcgc ttactaaaag ccagataaca      4740
gtatgcgtat ttgcgcgctg attttttgcgg tataagaata tatactgata tgtatacccg      4800
aagtatgtca aaaagaggtg tgcttctaga atgcagttta aggtttacac ctataaaaga      4860
gagagccgtt atcgtctgtt tgtggatgta cagagtgata ttattgacac gcccgggcga      4920
cggatggtga tccccctggc cagtgcacgt ctgctgtcag ataaagtctc ccgtgaactt      4980
tacccggtgg tgcatatcgg ggatgaaagc tggcgcatga tgaccaccga tatggccagt      5040
gtgccggtct ccgttatcgg ggaagaagtg gctgatctca gccaccgcga aaatgacatc      5100
aaaaacgcca ttaacctgat gttctgggga atatagaatt cctcaggtcg accatagtga      5160
```

```
ctggatatgt tgtgttttac agtattatgt agtctgtttt ttatgcaaaa tctaatttaa      5220
tatattgata tttatatcat tttacgtttc tcgttcagct ttcttgtaca aagtggtctc      5280
gagttaatta attgatccgg gttattagta catttattaa gcgctagatt ctgtgcgttg      5340
ttgatttaca gacaattgtt gtacgtattt taataattca ttaaatttat aatctttagg      5400
gtggtatgtt agagcgaaaa tcaaatgatt ttcagcgtct ttatatctga atttaaatat      5460
taaatcctca atagatttgt aaaataggtt tcgattagtt tcaaacaagg gttgtttttc      5520
cgaaccgatg gctggactat ctaatggatt ttcgctcaac gccacaaaac ttgccaaatc      5580
ttgtagcagc aatctagctt tgtcgatatt cgtttgtgtt ttgttttgta ataaaggttc      5640
gacgtcgttc aaaatattat gcgcttttgt atttctttca tcactgtcgt tagtgtacaa      5700
ttgactcgac gtaaacacgt taaataaagc ttggacatat ttaacatcgg gcgtgttagc      5760
tttattaggc cgattatcgt cgtcgtccca accctcgtcg ttagaagttg cttccgaaga      5820
cgattttgcc atagccacac gacgcctatt aattgtgtcg gctaacacgt ccgcgatcaa      5880
atttgtagtt gagcttttg gaattatttc tgattgcggg cgttttggg cgggtttcaa       5940 tctaactgtg cccgatttta attcagacaa cacgttagaa agcgatggtg caggcggtgg      6000
taacatttca gacggcaaat ctactaatgg cggcggtggt ggagctgatg ataaatctac      6060
catcggtgga ggcgcaggcg gggctggcgg cggaggcgga ggcggaggtg gtggcggtga      6120
tgcagacggc ggtttaggct caaatgtctc tttaggcaac acagtcggca cctcaactat      6180
tgtactggtt tcgggcgccg ttttttggttt gaccggtctg agacgagtgc gatttttttc      6240
gtttctaata gcttccaaca attgttgtct gtcgtctaaa ggtgcagcgg gttgaggttc      6300
cgtcggcatt ggtggagcgg gcggcaattc agacatcgat ggtggtggtg gtggtggagg      6360
cgctggaatg ttaggcacgg gagaaggtgg tggcggcggt gccgccggta taatttgttc      6420
tggtttagtt tgttcgcgca cgattgtggg caccggcgca ggcgccgctg gctgcacaac      6480
ggaaggtcgt ctgcttcgag gcagcgcttg gggtggtggc aattcaatat tataattgga      6540
atacaaatcg taaaaatctg ctataagcat tgtaatttcg ctatcgttta ccgtgccgat      6600
atttaacaac cgctcaatgt aagcaattgt attgtaaaga gattgtctca agctcggatc      6660
ccgcacgccg ataacaagcc ttttcatttt tactacagca ttgtagtggc gagacacttc      6720
gctgtcgtcg acgtacatgt atgctttgtt gtcaaaaacg tcgttggcaa gctttaaaat      6780
atttaaaaga acatctctgt tcagcaccac tgtgttgtcg taaatgttgt ttttgataat      6840
ttgcgcttcc gcagtatcga cacgttcaaa aaattgatgc gcatcaattt tgttgttcct      6900
attattgaat aaataagatt gtacagattc atatctacga ttcgtcatgg ccaccacaaa      6960
tgctacgctg caaacgctgg tacaatttta cgaaaactgc aaaaacgtca aaactcggta      7020
taaaataatc aacgggcgct ttggcaaaat atctatttta tcgcacaagc ccactagcaa      7080
attgtatttg cagaaaacaa tttcggcgca caattttaac gctgacgaaa taaaagttca      7140
ccagttaatg agcgaccacc caatttttat aaaaatctat tttaatcacg gttccatcaa      7200
caaccaagtg atcgtgatgg actacattga ctgtcccgat ttatttgaaa cactacaaat      7260
taaaggcgag ctttcgtacc aacttgttag caatattatt agacagctgt gtgaagcgct      7320
caacgatttg cacaagcaca atttcataca caacgacata aaactcgaaa atgtcttata      7380
tttcgaagca cttgatcgcg tgtatgtttt cgattacgga ttgtgcaaac acgaaaactc      7440
acttagcgtg cacgacggca cgttggagta tttttagtccg gaaaaaattc gacacacaac      7500
```

```
tatgcacgtt tcgtttgact ggtacgccgt cggcgtgtta acatacaagt tgctaaccgg    7560
cggccgacac ccatttgaaa aaagcgaaga cgaaatgttg gacttgaata gcatgaagcg    7620
tcgtcagcaa tacaatgaca ttggcgtttt aaaacacgtt cgtaacgtta acgctcgtga    7680
ctttgtgtac tgcctaacaa gatacaacat agattgtaga ctcacaaatt acaaacaaat    7740
tataaaacat gagttttgt cgtaaaaatg ccacttgttt tacgagtaga attctacgtg    7800
taacacacga tctaaaagat gatgtcattt tttatcaatg actcatttgt tttaaaacag    7860
acttgtttta cgagtagaat ctacgtgta aagcatgatc gtgagtggtg ttaataaaat    7920
cataaaaatt attgtaaatg tttattattt aaaaacgatt caaatatata ataaaaacaa    7980
tctacatcta tttcttcaca atccataaca cacaacaggt ccatcaatga gttttttgtct   8040 ttatccgaca tactatgtgc atgtaacaaa tcaaatacat cttttaaatt tttatacaca    8100
tctttacatt gtctaccaaa atctttaata accctataac aaggaaaaga cttttcttct    8160
tgcgtggttt tgccgcgcag atattgaaat aaaatgtgca tgcacgacaa cttgtgttta    8220
ctaaaatgct ccttgcctat accgcaaaac cggccataca tttcggcgat tacacgcgga    8280
caattgtacg attcgtctac gtgtaaacga tcatcataat cactcttgcg caaacgaata    8340
aattttttca ccgcttccga caaacgaggc accaattcgg cgggcacgct tcgatacatt    8400
attctgtgca cataagttac cacacaaaat ttattgtacc accatccgac aacgtcgtta    8460
ttagggttga acacgttggc gatgcgcagc agtttcccgt ttctcatgaa atattcaaag    8520
cggcccaaaa taatttgcaa gcaatccaac atgtcttgag aaatttctcg ttcaaaattg    8580
ttcaaagaga atatctgcca tccgttttga acgcgcacgc tgacgggaac caccgcatcg    8640
atttgctcca acacttcacg gacgttatcg tcgatgccca tcgtttcgct ggtgctgaac    8700
caatgggaaa ggctcttgat ggaatcgccc gcgtctatca tcttgaccgc ttcgtcaaag    8760
gtgcaactgc cgctcttcaa acgccgcata gcggtcacgt cccgctctat gcacgacata    8820
ccgtttacgt acgattctga taggtattcc tgaactatac ggtaatggtg atacgactcg    8880
ccatacacgt cgtgcacctc attgtattta gcataataat tgtaaattat taactttgca    8940
gcgagagaca tgttgtcagt aaagcggtgc taggctcaat aatactgatg tacaggcacg    9000
cgtgctattt atatataatt tcgcaaggag gggagctgtt atcggttgct attattaaag    9060
aatggccgtc tgtttttatc acaagcttgg cagcctcaac catgaagcgt cgtcattgta    9120
aattaaattc tctgcctcaa gaattatttg acaagattgt cgagtattta tctttatctg    9180
attactgcaa tttggtgctt gtctgtaaaa gaccttctag taaatataac gtgatatttg    9240
atagtactaa tcaccaacat ttgaaaggcg tgtacaaaaa gacagacgtg caaataacaa    9300
gctacaacga atacatcaac tgtatttgca acgaactgag acaagacgaa ttctatgcca    9360
aatcatcatg gattgcgagt atttgcggtc accagagagc gacaatttt agtgtaacaa    9420 ataaacaagt agaaatgaaa tatcatttgt ataatatagc aattgtggaa agtgaagatt    9480
gcaacggatt ttacccattt gagccaacgc gcgattgttt aatatgcaaa caaaaaaacc    9540
aatgtcctcg taattcattt attgtttcgt tgtgtaaata tttagaaaaa caaaatgtac    9600
aatcaaactt tatatattat ttatacgaaa taaatacata ataataacta ttatacatgt    9660 ttttattttta caatacttcc tgtataaacct ctctaactac attaggagta caatccacgt    9720
caattacacg tttagctatt tttctaattt tgtaatgttt atcgtagagt ttttcgttaa    9780
tacattgaat agccaacaag ggatttgggt gcacaccgtc atagagtact tccatgtcgt    9840
cttcaaagcg cattttttcgc ttgcgaaaat gccgctcttg gcccaaaaca aaagcgagtt    9900
```

| gatgcggtc gtcgatgcgt tccgaaaata cggccaaatg ctggtgtttg gtgatgtcgc | 9960 |
| cggaaacgt caccgtgcca ttttgctttt ccgccacgac | 10000 |

<210> SEQ ID NO 3
<211> LENGTH: 10000
<212> TYPE: DNA
<213> ORGANISM: Artificial Sequence
<220> FEATURE:
<223> OTHER INFORMATION: Polyhedrin locus of vBacHTS_HisGst
<220> FEATURE:
<221> NAME/KEY: source
<222> LOCATION: (4523)..(4553)
<223> OTHER INFORMATION: F 6His
<220> FEATURE:
<221> NAME/KEY: source
<222> LOCATION: (4523)..(5231)
<223> OTHER INFORMATION: F HGst
<220> FEATURE:
<221> NAME/KEY: promoter
<222> LOCATION: (4428)..(4520)
<223> OTHER INFORMATION: F pPolyhedrin
<220> FEATURE:
<221> NAME/KEY: misc_feature
<222> LOCATION: (5831)..(5955)
<223> OTHER INFORMATION: R attR2
<220> FEATURE:
<221> NAME/KEY: misc_feature
<222> LOCATION: (5242)..(5366)
<223> OTHER INFORMATION: F attR1

<400> SEQUENCE: 3

| gaattctacc cgtaaagcga gtttagtttt gaaaaacaaa tgacatcatt tgtataatga | 60 |
| catcatcccc tgattgtgtt ttacaagtag aattctatcc gtaaagcgag ttcagttttg | 120 |
| aaaacaaatg agtcatacct aaacacgtta ataatcttct gatatcagct tatgactcaa | 180 |
| gttatgagcc gtgtgcaaaa catgagataa gtttatgaca tcatccactg atcgtgcgtt | 240 |
| acaagtagaa ttctactcgt aaagccagtt cggttatgag ccgtgtgcaa acatgacat | 300 |
| cagcttatga ctcatacttg attgtgtttt acgcgtagaa ttctactcgt aaagcgagtt | 360 |
| cggttatgag ccgtgtgcaa acatgacat cagcttatga gtcataatta atcgtgcgtt | 420 |
| acaagtagaa ttctactcgt aaagcgagtt gaaggatcat atttagttgc gtttatgaga | 480 |
| taagattgaa agcacgtgta aaatgtttcc cgcgcgttgg cacaactatt tacaatgcgg | 540 |
| ccaagttata aaagattcta atctgatatg ttttaaaaca cctttgcggc ccgagttgtt | 600 |
| tgcgtacgtg actagcgaag aagatgtgtg gaccgcagaa cagatagtaa aacaaaaccc | 660 |
| tagtattgga gcaataatcg atttaaccaa cacgtctaaa tattatgatg gtgtgcattt | 720 |
| tttgcgggcg ggcctgttat acaaaaaaat tcaagtacct ggccagactt tgccgcctga | 780 |
| aagcatagtt caagaattta ttgacacggt aaaagaattt acagaaaagt gtcccggcat | 840 |
| gttggtgggc gtgcactgca cacacggtat taatcgcacc ggttacatgg tgtgcagata | 900 |
| tttaatgcac accctgggta ttgcgccgca ggaagccata gatagattcg aaaaagccag | 960 |
| aggtcacaaa attgaaagac aaaattacgt tcaagattta ttaatttaat taatattatt | 1020 |
| tgcattcttt aacaaatact ttatcctatt ttcaaattgt tgcgcttctt ccagcgaacc | 1080 |
| aaaactatgc ttcgcttgct ccgtttagct tgtagccgat cagtggcgtt gttccaatcg | 1140 |
| acggtaggat taggccggat attctccacc acaatgttgg caacgttgat gttacgttta | 1200 |
| tgcttttggt tttccacgta cgtcttttgg ccggtaatag ccgtaaacgt agtgccgtcg | 1260 |
| cgcgtcacgc acaacaccgg atgtttgcgc ttgtccgcgg ggtattgaac cgcgcgatcc | 1320 |

-continued

```
gacaaatcca ccactttggc aactaaatcg gtgacctgcg cgtctttttt ctgcattatt   1380
tcgtctttct tttgcatggt ttcctggaag ccggtgtaca tgcggtttag atcagtcatg   1440
acgcgcgtga cctgcaaatc tttggcctcg atctgcttgt ccttgatggc aacgatgcgt   1500
tcaataaact cttgtttttt aacaagttcc tcggtttttt gcgccaccac cgcttgcagc   1560
gcgtttgtgt gctcggtgaa tgtcgcaatc agcttagtca ccaactgttt gctctcctcc   1620
tcccgttgtt tgatcgcggg atcgtacttg ccggtgcaga gcacttgagg aattacttct   1680
tctaaaagcc attcttgtaa ttctatggcg taaggcaatt tggacttcat aatcagctga   1740
atcacgccgg atttagtaat gagcactgta tgcggctgca aatacagcgg gtcgcccctt   1800
ttcacgacgc tgttagaggt agggccccca ttttggatgg tctgctcaaa taacgatttg   1860
tatttattgt ctacatgaac acgtatagct ttatcacaaa ctgtatattt taaactgtta   1920
gcgacgtcct tggccacgaa ccggacctgt tggtcgcgct ctagcacgta ccgcaggttg   1980
aacgtatctt ctccaaattt aaattctcca atttttaacgc gagccatttt gatacacgtg   2040
tgtcgatttt gcaacaacta ttgttttta acgcaaacta aacttattgt ggtaagcaat   2100
aattaaatat gggggaacat cgccgctac aacactcgtc gttatgaacg cagacggcgc   2160
cggtctcggc gcaagcggct aaaacgtgtt gcgcgttcaa cgcggcaaac atcgcaaaag   2220
ccaatagtac agttttgatt tgcatattaa cggcgatttt ttaaattatc ttatttaata   2280
aatagttatg acgcctacaa ctccccgccc gcgttgactc gctgcacctc gagcagttcg   2340
ttgacgcctt cctccgtgtg gccgaacacg tcgagcgggt ggtcgatgac cagcggcgtg   2400
ccgcacgcga cgcacaagta tctgtacacc gaatgatcgt cgggcgaagg cacgtcggcc   2460
tccaagtggc aatattggca aattcgaaaa tatatacagt tgggttgttt gcgcatatct   2520
atcgtggcgt tgggcatgta cgtccgaacg ttgatttgca tgcaagccga aattaaatca   2580
ttgcgattag tgcgattaaa acgttgtaca tcctcgcttt taatcatgcc gtcgattaaa   2640
tcgcgcaatc gagtcaagtg atcaaagtgt ggaataatgt tttctttgta ttcccgagtc   2700
aagcgcagcg cgtattttaa caaactagcc atcttgtaag ttagtttcat ttaatgcaac   2760
tttatccaat aatatattat gtatcgcacg tcaagaatta acaatgcgcc cgttgtcgca   2820
tctcaacacg actatgatag agatcaaata aagcgcgaat taaatagctt gcgacgcaac   2880
gtgcacgatc tgtgcacgcg ttccggcacg agctttgatt gtaataagtt tttacgaagc   2940
gatgacatga cccccgtagt gacaacgatc acgcccaaaa gaactgccga ctacaaaatt   3000
accgagtatg tcggtgacgt taaaactatt aagccatcca atcgaccgtt agtcgaatca   3060
ggaccgctgg tgcagaagc cgcgaagtat ggcgaatgca tcgtataacg tgtggagtcc   3120
gctcattaga gcgtcatgtt tagacaagaa agctacatat ttaattgatc ccgatgattt   3180
tattgataaa ttgaccctaa ctccatacac ggtattctac aatggcgggg ttttggtcaa   3240
aatttccgga ctgcgattgt acatgctgtt aacggctccg cccactatta atgaaattaa   3300
aaattccaat tttaaaaaac gcagcaagag aaacatttgt atgaaagaat gcgtagaagg   3360
aaagaaaaat gtcgtcgaca tgctgaacaa caagattaat atgcctccgt gtataaaaaa   3420 atatattgaac gatttgaaag aaaacaatgt accgcgcggc ggtatgtaca ggaagaggtt   3480
tatactaaac tgttacattg caaacgtggt ttcgtgtgcc aagtgtgaaa accgatgttt   3540
aatcaaggct ctgacgcatt tctacaacca cgactccaag tgtgtgggtg aagtcatgca   3600
tcttttaatc aaatcccaag atgtgtataa accaccaaac tgccaaaaaa tgaaaactgt   3660
cgacaagctc tgtccgtttg ctggcaactg caagggtctc aatcctattt gtaattattg   3720
```

-continued

```
aataataaaa caattataaa tgctaaatttt gtttttatt aacgatacaa accaaacgca    3780
acaagaacat tgtagtatt atctataatt gaaaacgcgt agttataatc gctgaggtaa    3840
tatttaaaat cattttcaaa tgattcacag ttaatttgcg acaatataat tttatttca    3900 cataaactag acgccttgtc gtcttcttct tcgtattcct tctctttttc attttctcc    3960 tcataaaat taacatagtt attatcgtat ccatatatgt atctatcgta tagagtaaat    4020 ttttgttgt cataaatata tatgtctttt ttaatggggt gtatagtacc gctgcgcata    4080 gttttctgt aatttacaac agtgctattt tctggtagtt cttcgagtg tgttgcttta    4140 attattaaat ttatataatc aatgaatttg ggatcgtcgg ttttgtacaa tatgttgccg    4200
gcatagtacg cagcttcttc tagttcaatt acaccatttt ttagcagcac cggattaaca    4260
taactttcca aaatgttgta cgaaccgtta acaaaaaca gttcacctcc cttttctata    4320
ctattgtctg cgagcagttg tttgttgtta aaaataacag ccattgtaat gagacgcaca    4380
aactaatatc acaaactgga aatgtctatc aatatatagt tgctgatatc atggagataa    4440
ttaaaatgat aaccatctcg caaataaata agtattttac tgttttcgta acagttttgt    4500 aataaaaaa cctataaata cggatctatg catcatcacc atcatcacgg atctatgtcc    4560
cctatactag gttattggaa aattaagggc cttgtgcaac ccactcgact tcttttggaa    4620
tatcttgaag aaaaatatga agagcatttg tatgagcgcg atgaaggtga taatggcga    4680 aacaaaagt ttgaattggg tttggagttt cccaatcttc cttattatat tgatggtgat    4740
gttaaattaa cacagtctat ggccatcata cgttatatag ctgacaagca caacatgttg    4800
ggtggttgtc caaagagcg tgcagagatt tcaatgcttg aaggagcggt tttggatatt    4860
agatacggtt tttcgagaat tgcatatagt aaagactttg aaactctcaa agttgatttt    4920
cttagcaagc tacctgaaat gctgaaaatg ttcgaagatc gtttatgtca taaacatat    4980 ttaaatggta atcatgtaac ccatcctgac ttcatgttgt atgacgctct tgatgttgtt    5040
ttatacatgg acccaatgtg cctggatgcg ttcccaaaat tagtttgttt taaaaaacgt    5100
attgaagcta tcccacaaat tgataagtac ttgaaatcca gcaagtatat agcatggcct    5160
ttgcagggct ggcaagccac gtttggtggt ggcgaccatc ctccaaaatc ggatctggtt    5220
ccgcgtggat cccggggtac cacaagtttg tacaaaaaag ctgaacgaga aacgtaaaat    5280
gatataaata tcaatatatt aaattagatt ttgcataaaa aacagactac ataatactgt    5340
aaaacacaac atatccagtc actatggcgg ccgcattagg cacccctag gaattcgctt    5400 actaaaagcc agataacagt atgcgtattt gcgcgctgat ttttgcggta taagaatata    5460
tactgatatg tatacccgaa gtatgtcaaa aagaggtgtg cttctagaat gcagtttaag    5520
gtttacacct ataaagaga gagccgttat cgtctgtttg tggatgtaca gagtgatatt    5580
attgacacgc ccgggcgacg gatggtgatc cccctggcca gtgcacgtct gctgtcagat    5640
aaagtctccc gtgaacttta cccggtggtg catatcgggg atgaaagctg gcgcatgatg    5700
accaccgata tggccagtgt gccggtctcc gttatcgggg aagaagtggc tgatctcagc    5760
caccgcgaaa atgacatcaa aaacgccatt aacctgatgt tctggggaat atagaattcc    5820
tcaggtcgac catagtgact ggatatgttg tgttttacag tattatgtag tctgtttttt    5880
atgcaaaatc taatttaata tattgatatt tatatcattt tacgtttctc gttcagcttt    5940
cttgtacaaa gtggtctcga gttaattaat tgatccgggt tattagtaca tttattaagc    6000
gctagattct gtgcgttgtt gatttacaga caattgttgt acgtattta ataattcatt    6060
```

```
aaatttataa tctttagggt ggtatgttag agcgaaaatc aaatgattt  cagcgtcttt  6120
atatctgaat ttaaatatta aatcctcaat agatttgtaa aataggtttc gattagtttc  6180
aaacaagggt tgtttttccg aaccgatggc tggactatct aatggattt  cgctcaacgc  6240
cacaaaactt gccaaatctt gtagcagcaa tctagctttg tcgatattcg tttgtgtttt  6300
gttttgtaat aaaggttcga cgtcgttcaa aatattatgc gcttttgtat ttctttcatc  6360
actgtcgtta gtgtacaatt gactcgacgt aaacacgtta aataaagctt ggacatattt  6420
aacatcggc  gtgttagctt tattaggccg attatcgtcg tcgtcccaac cctcgtcgtt  6480
agaagttgct tccgaagacg attttgccat agccacacga cgcctattaa ttgtgtcggc  6540
taacacgtcc gcgatcaaat ttgtagttga gcttttgga  attatttctg attgcgggcg  6600
tttttgggcg ggtttcaatc taactgtgcc cgatttaat  tcagacaaca cgttagaaag  6660
cgatggtgca ggcggtggta acatttcaga cggcaaatct actaatggcg gcggtggtgg  6720
agctgatgat aaatctacca tcggtggagg cgcaggcggg gctggcggcg gaggcggagg  6780
cggaggtggt ggcggtgatg cagacggcgg tttaggctca aatgtctctt taggcaacac  6840
agtcggcacc tcaactattg tactggtttc gggcgccgtt tttggtttga ccggtctgag  6900
acgagtgcga ttttttttcgt ttctaatagc ttccaacaat tgttgtctgt cgtctaaagg  6960
tgcagcgggt tgaggttccg tcggcattgg tggagcgggc ggcaattcag acatcgatgg  7020
tggtggtggt ggtggaggcg ctggaatgtt aggcacggga gaaggtggtg gcggcggtgc  7080
cgccggtata atttgttctg gtttagtttg ttcgcgcacg attgtgggca ccggcgcagg  7140
cgccgctggc tgcacaacgg aaggtcgtct gcttcgaggc agcgcttggg gtggtggcaa  7200
ttcaatatta taattggaat acaaatcgta aaaatctgct ataagcattg taatttcgct  7260
atcgtttacc gtgccgatat ttaacaaccg ctcaatgtaa gcaattgtat tgtaaagaga  7320
ttgtctcaag ctcggatccc gcacgccgat aacaagcctt tcatttttta ctacagcatt  7380
gtagtggcga gacacttcgc tgtcgtcgac gtacatgtat gctttgttgt caaaaacgtc  7440
gttggcaagc tttaaaatat ttaaaagaac atctctgttc agcaccactg tgttgtcgta  7500
aatgttgttt ttgataattt gcgcttccgc agtatcgaca cgttcaaaaa attgatgcgc  7560
atcaattttg ttgttcctat tattgaataa ataagattgt acagattcat atctacgatt  7620
cgtcatggcc accacaaatg ctacgctgca aacgctggta caattttacg aaaactgcaa  7680
aaacgtcaaa actcggtata aaataatcaa cgggcgcttt ggcaaaatat ctattttatc  7740
gcacaagccc actagcaaat tgtatttgca gaaaacaatt tcggcgcaca attttaacgc  7800
tgacgaaata aaagttcacc agttaatgag cgaccaccca aatttataa  aaatctattt  7860
taatcacggt tccatcaaca accaagtgat cgtgatggac tacattgact gtcccgattt  7920
atttgaaaca ctacaaatta aaggcgagct ttcgtaccaa cttgttagca atattattag  7980
acagctgtgt gaagcgctca acgatttgca caagcacaat ttcatacaca acgacataaa  8040
actcgaaaat gtcttatatt tcgaagcact tgatcgcgtg tatgtttgcg attacggatt  8100
gtgcaaacac gaaaactcac ttagcgtgca cgacggcacg ttggagtatt ttagtccgga  8160
aaaaattcga cacacaacta tgcacgtttc gtttgactgg tacgccgtcg cgtgttaac   8220
atacaagttg ctaaccggcg gccgacaccc atttgaaaaa agcgaagacg aaatgttgga  8280
cttgaatagc atgaagcgtc gtcagcaata caatgacatt ggcgttttaa aacacgttcg  8340
taacgttaac gctcgtgact ttgtgtactg cctaacaaga tacaacatag attgtagact  8400
cacaaattac aaacaaatta taaaacatga gttttttgtcg taaaaatgcc acttgttta   8460
```

```
cgagtagaat tctacgtgta acacacgatc taaaagatga tgtcattttt tatcaatgac    8520
tcatttgttt taaaacagac ttgttttacg agtagaattc tacgtgtaaa gcatgatcgt    8580
gagtggtgtt aataaaatca taaaaattat tgtaaatgtt tattatttaa aaacgattca    8640
aatatataat aaaaacaatc tacatctatt tcttcacaat ccataacaca caacaggtcc    8700
atcaatgagt ttttgtcttt atccgacata ctatgtgcat gtaacaaatc aaatacatct    8760
tttaaatttt tatacacatc tttacattgt ctaccaaaat ctttaataac cctataacaa    8820
ggaaaagact tttcttcttg cgtggttttg ccgcgcagat attgaaataa aatgtgcatg    8880
cacgacaact tgtgtttact aaaatgctcc ttgcctatac cgcaaaaccg gccatacatt    8940
tcggcgatta cacgcggaca attgtacgat tcgtctacgt gtaaacgatc atcataatca    9000
ctcttgcgca aacgaataaa ttttttcacc gcttccgaca acgaggcac caattcggcg    9060 ggcacgcttc gatacattat tctgtgcaca taagttacca cacaaaattt attgtaccac    9120
catccgacaa cgtcgttatt agggttgaac acgttggcga tgcgcagcag tttcccgttt    9180
ctcatgaaat attcaaagcg gcccaaaata atttgcaagc aatccaacat gtcttgagaa    9240
atttctcgtt caaaattgtt caaagagaat atctgccatc cgttttgaac gcgcacgctg    9300
acgggaacca ccgcatcgat ttgctccaac acttcacgga cgttatcgtc gatgcccatc    9360
gtttcgctgg tgctgaacca atgggaaagg ctcttgatgg aatcgcccgc gtctatcatc    9420
ttgaccgctt cgtcaaaggt gcaactgccg ctcttcaaac gccgcatagc ggtcacgtcc    9480
cgctctatgc acgacatacc gtttacgtac gattctgata ggtattcctg aactatacgg    9540
taatggtgat acgactcgcc atacacgtcg tgcacctcat tgtatttagc ataataattg    9600
taaattatta actttgcagc gagagacatg ttgtcagtaa agcggtgcta ggctcaataa    9660
tactgatgta caggcacgcg tgctatttat atataatttc gcaaggaggg gagctgttat    9720
cggttgctat tattaaagaa tggccgtctg tttttatcac aagcttggca gcctcaacca    9780
tgaagcgtcg tcattgtaaa ttaaattctc tgcctcaaga attatttgac aagattgtcg    9840
agtatttatc tttatctgat tactgcaatt tggtgcttgt ctgtaaaaga ccttctagta    9900
aatataacgt gatatttgat agtactaatc accaacattt gaaaggcgtg tacaaaaaga    9960
cagacgtgca aataacaagc tacaacgaat acatcaactg                         10000
```

```
<210> SEQ ID NO 4
<211> LENGTH: 10000
<212> TYPE: DNA
<213> ORGANISM: Artificial Sequence
<220> FEATURE:
<223> OTHER INFORMATION: Polyhedrin locus of vBacHTS_GST
<220> FEATURE:
<221> NAME/KEY: CDS
<222> LOCATION: (4528)..(5181)
<223> OTHER INFORMATION: F GST
<220> FEATURE:
<221> NAME/KEY: misc_feature
<222> LOCATION: (5482)..(5787)
<223> OTHER INFORMATION: F ccdB
<220> FEATURE:
<221> NAME/KEY: promoter
<222> LOCATION: (4428)..(4520)
<223> OTHER INFORMATION: F pPolyhedrin
<220> FEATURE:
<221> NAME/KEY: misc_feature
<222> LOCATION: (5215)..(5339)
<223> OTHER INFORMATION: F attR1
<220> FEATURE:
<221> NAME/KEY: misc_feature
<222> LOCATION: (5804)..(5928)
```

<223> OTHER INFORMATION: R attR2

<400> SEQUENCE: 4

```
gaattctacc cgtaaagcga gtttagtttt gaaaaacaaa tgacatcatt tgtataatga    60
catcatcccc tgattgtgtt ttacaagtag aattctatcc gtaaagcgag ttcagttttg   120
aaaacaaatg agtcatacct aaacacgtta ataatcttct gatatcagct tatgactcaa   180
gttatgagcc gtgtgcaaaa catgagataa gtttatgaca tcatccactg atcgtgcgtt   240
acaagtagaa ttctactcgt aaagccagtt cggttatgag ccgtgtgcaa acatgacat    300
cagcttatga ctcatacttg attgtgtttt acgcgtagaa ttctactcgt aaagcgagtt   360
cggttatgag ccgtgtgcaa acatgacat cagcttatga gtcataatta atcgtgcgtt   420
acaagtagaa ttctactcgt aaagcgagtt gaaggatcat atttagttgc gtttatgaga   480
taagattgaa agcacgtgta aaatgtttcc cgcgcgttgg cacaactatt tacaatgcgg   540
ccaagttata aaagattcta atctgatatg ttttaaaaca cctttgcggc ccgagttgtt   600
tgcgtacgtg actagcgaag aagatgtgtg gaccgcagaa cagatagtaa aacaaaaccc   660
tagtattgga gcaataatcg atttaaccaa cacgtctaaa tattatgatg gtgtgcattt   720
tttgcgggcg ggcctgttat acaaaaaaat tcaagtacct ggccagactt tgccgcctga   780
aagcatagtt caagaattta ttgacacggt aaaagaattt acagaaaagt gtcccggcat   840
gttggtgggc gtgcactgca cacacggtat taatcgcacc ggttacatgg tgtgcagata   900
tttaatgcac accctgggta ttgcgccgca ggaagccata gatagattcg aaaaagccag   960
aggtcacaaa attgaaagac aaaattacgt tcaagattta ttaatttaat taatattatt  1020
tgcattcttt aacaaatact ttatcctatt ttcaaattgt tgcgcttctt ccagcgaacc  1080
aaaactatgc ttcgcttgct ccgtttagct tgtagccgat cagtggcgtt gttccaatcg  1140
acggtaggat taggccggat attctccacc acaatgttgg caacgttgat gttacgttta  1200
tgcttttggt tttccacgta cgtctttttgg ccggtaatag ccgtaaacgt agtgccgtcg  1260
cgcgtcacgc acaacaccgg atgtttcgc ttgtccgcgg ggtattgaac cgcgcgatcc  1320
gacaaatcca ccactttggc aactaaatcg gtgacctgcg cgtctttttt ctgcattatt  1380
tcgtctttct tttgcatggt ttcctggaag ccggtgtaca tgcggtttag atcagtcatg  1440
acgcgcgtga cctgcaaatc tttggcctcg atctgcttgt ccttgatggc aacgatgcgt  1500
tcaataaact cttgtttttt aacaagttcc tcggtttttt gcgccaccac cgcttgcagc  1560
gcgtttgtgt gctcggtgaa tgtcgcaatc agcttagtca ccaactgttt gctctcctcc  1620
tcccgttgtt tgatcgcggg atcgtacttg ccggtgcaga gcacttgagg aattacttct  1680
tctaaaagcc attcttgtaa ttctatggcg taaggcaatt tggacttcat aatcagctga  1740
atcacgccgg atttagtaat gagcactgta tgcggctgca aatacagcgg gtcgcccctt  1800
ttcacgacgc tgttagaggt agggcccca ttttggatgg tctgctcaaa taacgatttg  1860
tatttattgt ctacatgaac acgtatagct ttatcacaaa ctgtatattt taaactgtta  1920
gcgacgtcct tggccacgaa ccggaccctgt tggtcgcgct ctagcacgta ccgcaggttg  1980
aacgtatctt ctccaaattt aaattctcca attttaacgc gagccatttt gatacacgtg  2040
tgtcgatttt gcaacaacta ttgttttta acgcaaacta aacttattgt ggtaagcaat  2100
aattaaatat gggggaacat gcgccgctac aacactcgtc gttatgaacg cagacggcgc  2160
cggtctcggc gcaagcggct aaaacgtgtt gcgcgttcaa cgcggcaaac atcgcaaaag  2220
ccaatagtac agttttgatt tgcatattaa cggcgatttt ttaaattatc ttatttaata  2280
```

-continued

```
aatagttatg acgcctacaa ctccccgccc gcgttgactc gctgcacctc gagcagttcg    2340
ttgacgcctt cctccgtgtg gccgaacacg tcgagcgggt ggtcgatgac cagcggcgtg    2400
ccgcacgcga cgcacaagta tctgtacacc gaatgatcgt cgggcgaagg cacgtcggcc    2460
tccaagtggc aatattggca aattcgaaaa tatatacagt tgggttgttt gcgcatatct    2520
atcgtggcgt tgggcatgta cgtccgaacg ttgatttgca tgcaagccga aattaaatca    2580
ttgcgattag tgcgattaaa acgttgtaca tcctcgcttt taatcatgcc gtcgattaaa    2640
tcgcgcaatc gagtcaagtg atcaaagtgt ggaataatgt tttctttgta ttcccgagtc    2700
aagcgcagcg cgtattttaa caaactagcc atcttgtaag ttagtttcat ttaatgcaac    2760
tttatccaat aatatattat gtatcgcacg tcaagaatta acaatgcgcc cgttgtcgca    2820
tctcaacacg actatgatag agatcaaata aagcgcgaat aaatagctt gcgacgcaac    2880 gtgcacgatc tgtgcacgcg ttccggcacg agctttgatt gtaataagtt tttacgaagc    2940
gatgacatga cccccgtagt gacaacgatc acgcccaaaa gaactgccga ctacaaaatt    3000
accgagtatg tcggtgacgt taaaactatt aagccatcca atcgaccgtt agtcgaatca    3060
ggaccgctgg tgcgagaagc cgcgaagtat ggcgaatgca tcgtataacg tgtggagtcc    3120
gctcattaga gcgtcatgtt tagacaagaa agctacatat ttaattgatc ccgatgattt    3180
tattgataaa ttgaccctaa ctccatacac ggtattctac aatggcgggg ttttggtcaa    3240
aatttccgga ctgcgattgt acatgctgtt aacggctccg cccactatta atgaaattaa    3300
aaattccaat tttaaaaaac gcagcaagag aaacatttgt atgaaagaat gcgtagaagg    3360
aaagaaaaat gtcgtcgaca tgctgaacaa caagattaat atgcctccgt gtataaaaaa    3420
aatattgaac gatttgaaag aaaacaatgt accgcgcggc ggtatgtaca ggaagaggtt    3480
tatactaaac tgttacattg caaacgtggt ttcgtgtgcc aagtgtgaaa accgatgttt    3540
aatcaaggct ctgacgcatt tctacaacca cgactccaag tgtgtgggtg aagtcatgca    3600
tcttttaatc aaatcccaag atgtgtataa accaccaaac tgccaaaaaa tgaaaactgt    3660
cgacaagctc tgtccgtttg ctggcaactg caagggtctc aatcctattt gtaattattg    3720
aataataaaa caattataaa tgctaaattt gttttttatt aacgatacaa accaaacgca    3780
acaagaacat ttgtagtatt atctataatt gaaaacgcgt agtttataatc gctgaggtaa    3840 tatttaaaat cattttcaaa tgattcacag ttaatttgcg acaatataat tttattttca    3900
cataaactag acgccttgtc gtcttcttct tcgtattcct tctctttttc attttttctcc    3960 tcataaaaat taacatagtt attatcgtat ccatatatgt atctatcgta tagagtaaat    4020
tttttgttgt cataaatata tatgtctttt ttaatgggt gtatagtacc gctgcgcata    4080 gttttttctgt aatttacaac agtgctatt tctggtagtt cttcggagtg tgttgcttta    4140
attattaaat ttatataatc aatgaatttg ggatcgtcgg ttttgtacaa tatgttgccg    4200
gcatagtacg cagcttcttc tagttcaatt acaccatttt ttagcagcac cggattaaca    4260
taactttcca aaatgttgta cgaaccgtta aacaaaaaca gttcacctcc cttttctata    4320
ctattgtctg cgagcagttg tttgttgtta aaaataacag ccattgtaat gagacgcaca    4380
aactaatatc acaaactgga aatgtctatc aatatatagt tgctgatatc atggagataa    4440
ttaaaatgat aaccatctcg caaataaata agtatttac tgttttcgta acagttttgt    4500
aataaaaaaa cctataaaata cggatct     atg tcc cct ata cta ggt tat tgg    4551
                                   Met Ser Pro Ile Leu Gly Tyr Trp
                                    1               5
```

```
aaa att aag ggc ctt gtg caa ccc act cga ctt ctt ttg gaa tat ctt          4599
Lys Ile Lys Gly Leu Val Gln Pro Thr Arg Leu Leu Leu Glu Tyr Leu
     10                  15                  20 gaa gaa aaa tat gaa gag cat ttg tat gag cgc gat gaa ggt gat aaa          4647
Glu Glu Lys Tyr Glu Glu His Leu Tyr Glu Arg Asp Glu Gly Asp Lys
 25                  30                  35                  40 tgg cga aac aaa aag ttt gaa ttg ggt ttg gag ttt ccc aat ctt cct          4695
Trp Arg Asn Lys Lys Phe Glu Leu Gly Leu Glu Phe Pro Asn Leu Pro
                 45                  50                  55 tat tat att gat ggt gat gtt aaa tta aca cag tct atg gcc atc ata          4743
Tyr Tyr Ile Asp Gly Asp Val Lys Leu Thr Gln Ser Met Ala Ile Ile
             60                  65                  70 cgt tat ata gct gac aag cac aac atg ttg ggt ggt tgt cca aaa gag          4791
Arg Tyr Ile Ala Asp Lys His Asn Met Leu Gly Gly Cys Pro Lys Glu
         75                  80                  85 cgt gca gag att tca atg ctt gaa gga gcg gtt ttg gat att aga tac          4839
Arg Ala Glu Ile Ser Met Leu Glu Gly Ala Val Leu Asp Ile Arg Tyr
     90                  95                 100 ggt gtt tcg aga att gca tat agt aaa gac ttt gaa act ctc aaa gtt          4887
Gly Val Ser Arg Ile Ala Tyr Ser Lys Asp Phe Glu Thr Leu Lys Val
105                 110                 115                 120 gat ttt ctt agc aag cta cct gaa atg ctg aaa atg ttc gaa gat cgt          4935
Asp Phe Leu Ser Lys Leu Pro Glu Met Leu Lys Met Phe Glu Asp Arg
                125                 130                 135 tta tgt cat aaa aca tat tta aat ggt gat cat gta acc cat cct gac          4983
Leu Cys His Lys Thr Tyr Leu Asn Gly Asp His Val Thr His Pro Asp
            140                 145                 150 ttc atg ttg tat gac gct ctt gat gtt gtt tta tac atg gac cca atg          5031
Phe Met Leu Tyr Asp Ala Leu Asp Val Val Leu Tyr Met Asp Pro Met
        155                 160                 165 tgc ctg gat gcg ttc cca aaa tta gtt tgt ttt aaa aaa cgt att gaa          5079
Cys Leu Asp Ala Phe Pro Lys Leu Val Cys Phe Lys Lys Arg Ile Glu
    170                 175                 180 gct atc cca caa att gat aag tac ttg aaa tcc agc aag tat ata gca          5127
Ala Ile Pro Gln Ile Asp Lys Tyr Leu Lys Ser Ser Lys Tyr Ile Ala
185                 190                 195                 200 tgg cct ttg cag ggc tgg caa gcc acg ttt ggt ggt ggc gac cat cct          5175
Trp Pro Leu Gln Gly Trp Gln Ala Thr Phe Gly Gly Gly Asp His Pro
                205                 210                 215 cca aaa      tcggatctg gttccgcgtg atcccgggg taccacaagt ttgtacaaaa       5230
Pro Lys aagctgaacg agaaacgtaa aatgatataa atatcaatat attaaattag attttgcata       5290
aaaaacagac tacataatac tgtaaaacac aacatatcca gtcactatgg cggccgcatt       5350
aggcacccct taggaattcg cttactaaaa gccagataac agtatgcgta tttgcgcgct       5410
gatttttgcg gtataagaat atatactgat atgtataccc gaagtatgtc aaaaagaggt       5470
gtgcttctag aatgcagttt aaggtttaca cctataaaag agagagccgt tatcgtctgt       5530
ttgtggatgt acagagtgat attattgaca cgcccgggcg acggatggtg atcccctgg       5590 ccagtgcacg tctgctgtca gataaagtct cccgtgaact ttaccggtg gtgcatatcg       5650 gggatgaaag ctggcgcatg atgaccaccg atatggccag tgtgccggtc tccgttatcg       5710
gggaagaagt ggctgatctc agccaccgcg aaaatgacat caaaaacgcc attaacctga       5770
tgttctgggg aatatagaat tcctcaggtc gaccatagtg actggatatg ttgtgtttta       5830
cagtattatg tagtctgttt tttatgcaaa atcaattta atatattgat atttatatca       5890
ttttacgttt ctcgttcagc tttcttgtac aaagtggtct cgagttaatt aattgatccg       5950
```

-continued

```
ggttattagt acatttatta agcgctagat tctgtgcgtt gttgatttac agacaattgt    6010
tgtacgtatt ttaataattc attaaattta taatctttag ggtggtatgt tagagcgaaa    6070
atcaaatgat tttcagcgtc tttatatctg aatttaaata ttaaatcctc aatagatttg    6130
taaaataggt ttcgattagt ttcaaacaag ggttgttttt ccgaaccgat ggctggacta    6190
tctaatggat tttcgctcaa cgccacaaaa cttgccaaat cttgtagcag caatctagct    6250
ttgtcgatat tcgtttgtgt tttgttttgt aataaaggtt cgacgtcgtt caaaatatta    6310
tgcgcttttg tatttctttc atcactgtcg ttagtgtaca attgactcga cgtaaacacg    6370
ttaaataaag cttggacata tttaacatcg ggcgtgttag cttttattag ccgattatcg    6430
tcgtcgtccc aaccctcgtc gttagaagtt gcttccgaag acgattttgc catagccaca    6490
cgacgcctat taattgtgtc ggctaacacg tccgcgatca aatttgtagt tgagcttttt    6550
ggaattattt ctgattgcgg gcgttttttgg gcgggtttca atctaactgt gcccgatttt    6610
aattcagaca acacgttaga aagcgatggt gcaggcggtg gtaacatttc agacggcaaa    6670
tctactaatg gcggcggtgg tggagctgat gataaatcta ccatcggtgg aggcgcaggc    6730
ggggctggcg gcggaggcgg aggcggaggt ggtggcggtg atgcagacgg cggtttaggc    6790
tcaaatgtct ctttaggcaa cacagtcggc acctcaacta ttgtactggt ttcgggcgcc    6850
gttttttggtt tgaccggtct gagacgagtg cgatttttttt cgtttctaat agcttccaac    6910
aattgttgtc tgtcgtctaa aggtgcagcg ggttgaggtt ccgtcggcat tggtggagcg    6970
ggcggcaatt cagacatcga tggtggtggt ggtggtggag gcgctggaat gttaggcacg    7030
ggagaaggtg gtggcggcgg tgccgccggt ataatttgtt ctggtttagt ttgttcgcgc    7090
acgattgtgg gcaccggcgc aggcgccgct ggctgcacaa cggaaggtcg tctgcttcga    7150
ggcagcgctt ggggtggtgg caattcaata ttataattgg aatacaaatc gtaaaaatct    7210
gctataagca ttgtaattttc gctatcgttt accgtgccga tatttaacaa ccgctcaatg    7270
taagcaattg tattgtaaag agattgtctc aagctcggat cccgcacgcc gataacaagc    7330
cttttcattt ttactacagc attgtagtgg cgagacactt cgctgtcgtc gacgtacatg    7390
tatgctttgt tgtcaaaaac gtcgttggca agctttaaaa tatttaaaag aacatctctg    7450
ttcagcacca ctgtgttgtc gtaaatgttg ttttttgataa tttttgcgcttc cgcagtatcg    7510
acacgttcaa aaaattgatg cgcatcaatt ttgttgttcc tattattgaa taaataagat    7570
tgtacagatt catatctacg attcgtcatg gccaccacaa atgctacgct gcaaacgctg    7630
gtacaattttt acgaaaactg caaaaacgtc aaaactcggt ataaaataat caacgggcgc    7690
tttggcaaaa tatctatttt atcgcacaag cccactagca aattgtattt gcagaaaaca    7750
atttcggcgc acaattttaa cgctgacgaa ataaagttcc accagttaat gagcgaccac    7810
ccaaattttta taaaaatcta tttttaatcac ggttccatca acaaccaagt gatcgtgatg    7870
gactacattg actgtcccga tttatttgaa acactacaaa ttaaaggcga gctttcgtac    7930
caacttgtta gcaatattat tagacagctg tgtgaagcgc tcaacgattt gcacaagcac    7990
aatttcatac acaacgacat aaaactcgaa aatgtcttat atttcgaagc acttgatcgc    8050
gtgtatgttt gcgattacgg attgtgcaaa cacgaaaact cacttagcgt gcacgacggc    8110
acgttggagt atttagtcc ggaaaaaatt cgacacacaa ctatgcacgt ttcgtttgac    8170
tggtacgccg tcggcgtgtt aacatacaag ttgctaaccg gcggccgaca cccatttgaa    8230
aaaagcgaag acgaaatgtt ggacttgaat agcatgaagc gtcgtcagca atacaatgac    8290
attggcgttt taaaacacgt tcgtaacgtt aacgctcgtg actttgtgta ctgcctaaca    8350
```

```
agatacaaca tagattgtag actcacaaat tacaaacaaa ttataaaaca tgagtttttg    8410
tcgtaaaaat gccacttgtt ttacgagtag aattctacgt gtaacacacg atctaaaaga    8470
tgatgtcatt ttttatcaat gactcatttg ttttaaaaca gacttgtttt acgagtagaa    8530
ttctacgtgt aaagcatgat cgtgagtggt gttaataaaa tcataaaaat tattgtaaat    8590
gtttattatt taaaaacgat tcaaatatat aataaaaaca atctcatctc atttcttcac    8650
aatccataac acacaacagg tccatcaatg agttttttgtc tttatccgac atactatgtg    8710
catgtaacaa atcaaataca tcttttaaat tttatacac atctttacat tgtctaccaa     8770
aatctttaat aaccctataa caaggaaaag acttttcttc ttgcgtggtt ttgccgcgca    8830
gatattgaaa taaatgtgc atgcacgaca acttgtgttt actaaaatgc tccttgccta    8890
taccgcaaaa ccggccatac atttcggcga ttacacgcgg acaattgtac gattcgtcta    8950
cgtgtaaacg atcatcataa tcactcttgc gcaaacgaat aaatttttc accgcttccg     9010 acaaacgagg caccaattcg gcgggcacgc ttcgatacat tattctgtgc acataagtta    9070
ccacacaaaa tttattgtac caccatccga caacgtcgtt attagggttg aacacgttgg    9130
cgatgcgcag cagtttcccg tttctcatga aatattcaaa gcggcccaaa ataatttgca    9190
agcaatccaa catgtcttga gaaatttctc gttcaaaatt gttcaaagag aatatctgcc    9250
atccgttttg aacgcgcacg ctgacgggaa ccaccgcatc gatttgctcc aacacttcac    9310
ggacgttatc gtcgatgccc atcgtttcgc tggtgctgaa ccaatgggaa aggctcttga    9370
tggaatcgcc cgcgtctatc atcttgaccg cttcgtcaaa ggtgcaactg ccgctcttca    9430
aacgccgcat agcggtcacg tcccgctcta tgcacgacat accgtttacg tacgattctg    9490
ataggtattc ctgaactata cggtaatggt gatacgactc gccatacacg tcgtgcacct    9550
cattgtattt agcataataa ttgtaaatta ttaactttgc agcgagagac atgttgtcag    9610
taaagcggtc ctaggctcaa taatactgat gtacaggcac gcgtgctatt tatatataat    9670
ttcgcaagga ggggagctgt tatcggttgc tattattaaa gaatggccgt ctgtttttat    9730
cacaagcttg gcagcctcaa ccatgaagcg tcgtcattgt aaattaaatt ctctgcctca    9790
agaattattt gacaagattg tcgagtattt atctttatct gattactgca atttggtgct    9850
tgtctgtaaa agaccttcta gtaaatataa cgtgatattt gatagtacta atcaccaaca    9910
tttgaaaggc gtgtacaaaa agacagacgt gcaaataaca agctacaacg aatacatcaa    9970
ctgtatttgc aacgaactga gacaagacga                                     10000
```

<210> SEQ ID NO 5
<211> LENGTH: 10000
<212> TYPE: DNA
<213> ORGANISM: Artificial Sequence
<220> FEATURE:
<223> OTHER INFORMATION: Polyhedrin locus of vBacHTS_GFP virus
<220> FEATURE:
<221> NAME/KEY: CDS
<222> LOCATION: (4531)..(5247)
<223> OTHER INFORMATION: F EGFP
<220> FEATURE:
<221> NAME/KEY: misc_feature
<222> LOCATION: (5521)..(5826)
<223> OTHER INFORMATION: F ccdB
<220> FEATURE:
<221> NAME/KEY: promoter
<222> LOCATION: (4428)..(4520)
<223> OTHER INFORMATION: F pPolyhedrin
<220> FEATURE:
<221> NAME/KEY: misc_feature
<222> LOCATION: (5843)..(5967)

<223> OTHER INFORMATION: R attR2
<220> FEATURE:
<221> NAME/KEY: misc_feature
<222> LOCATION: (5254)..(5378)
<223> OTHER INFORMATION: F attR1

<400> SEQUENCE: 5

```
gaattctacc cgtaaagcga gtttagtttt gaaaaacaaa tgacatcatt tgtataatga      60
catcatcccc tgattgtgtt ttacaagtag aattctatcc gtaaagcgag ttcagttttg     120
aaaacaaatg agtcatacct aaacacgtta ataatcttct gatatcagct tatgactcaa     180
gttatgagcc gtgtgcaaaa catgagataa gtttatgaca tcatccactg atcgtgcgtt    240
acaagtagaa ttctactcgt aaagccagtt cggttatgag ccgtgtgcaa acatgacat     300
cagcttatga ctcatacttg attgtgtttt acgcgtagaa ttctactcgt aaagcgagtt    360
cggttatgag ccgtgtgcaa acatgacat cagcttatga gtcataatta atcgtgcgtt     420
acaagtagaa ttctactcgt aaagcgagtt gaaggatcat atttagttgc gtttatgaga    480
taagattgaa agcacgtgta aaatgtttcc cgcgcgttgg cacaactatt tacaatgcgg    540
ccaagttata aaagattcta atctgatatg ttttaaaaca cctttgcggc ccgagttgtt    600
tgcgtacgtg actagcgaag aagatgtgtg gaccgcagaa cagatagtaa aacaaaaccc    660
tagtattgga gcaataatcg atttaaccaa cacgtctaaa tattatgatg gtgtgcatt     720
tttgcgggcg ggcctgttat acaaaaaaat tcaagtacct ggccagactt tgccgcctga    780
aagcatagtt caagaattta ttgacacggt aaaagaattt acagaaaagt gtcccggcat    840
gttggtgggc gtgcactgca cacgggtat taatcgcacc ggttacatgg tgtgcagata    900
tttaatgcac accctgggta ttgcgccgca ggaagccata gatagattcg aaaaagccag    960
aggtcacaaa attgaaagac aaaattacgt tcaagattta ttaatttaat taatatatt    1020
tgcattcttt aacaaatact ttatcctatt ttcaaattgt tgcgcttctt ccagcgaacc   1080
aaaactatgc ttcgcttgct ccgtttagct tgtagccgat cagtggcgtt gttccaatcg   1140
acggtaggat taggccggat attctccacc acaatgttgg caacgttgat gttacgttta   1200
tgcttttggt tttccacgta cgtcttttgg ccggtaatag ccgtaaacgt agtgccgtcg   1260
cgcgtcacgc acaacaccgg atgtttcgcg ttgtccgcgg ggtattgaac cgcgcgatcc   1320
gacaaatcca ccactttggc aactaaatcg gtgacctgcg cgtcttttt ctgcattatt   1380
tcgtctttct tttgcatggt ttcctggaag ccggtgtaca tgcggtttag atcagtcatg   1440
acgcgcgtga cctgcaaatc tttggcctcg atctgcttgt ccttgatggc aacgatgcgt   1500
tcaataaact cttgtttttt aacaagttcc tcggtttttt gcgccaccac cgcttgcagc   1560
gcgtttgtgt gctcggtgaa tgtcgcaatc agcttagtca ccaactgttt gctctcctcc   1620
tcccgttgtt tgatcgcggg atcgtacttg ccggtgcaga gcacttgagg aattacttct   1680
tctaaaagcc attcttgtaa ttctatggcg taaggcaatt tggacttcat aatcagctga   1740
atcacgccgg atttagtaat gagcactgta tgcggctgca atacagcgg tcgcccctt     1800
ttcacgacgc tgttagaggt agggccccca ttttggatgg tctgctcaaa taacgatttg   1860
tatttattgt ctacatgaac acgtatagct ttatcacaaa ctgtatattt taaactgtta   1920
gcgacgtcct tggccacgaa ccggaccgt tggtcgcgct ctagcacgta ccgcaggttg   1980
aacgtatctt ctccaaattt aaattctcca attttaacgc gagccatttt gatacacgtg   2040
tgtcgatttt gcaacaacta ttgtttttta acgcaaacta aacttattgt ggtaagcaat   2100
aattaaatat gggggaacat gcgccgctac aacactcgtc gttatgaacg cagacggcgc   2160
```

-continued

```
cggtctcggc gcaagcggct aaaacgtgtt gcgcgttcaa cgcggcaaac atcgcaaaag    2220
ccaatagtac agttttgatt tgcatattaa cggcgatttt ttaaattatc ttatttaata    2280
aatagttatg acgcctacaa ctccccgccc gcgttgactc gctgcacctc gagcagttcg    2340
ttgacgcctt cctccgtgtg gccgaacacg tcgagcgggt ggtcgatgac cagcggcgtg    2400
ccgcacgcga cgcacaagta tctgtacacc gaatgatcgt cgggcgaagg cacgtcggcc    2460
tccaagtggc aatattggca aattcgaaaa tatatacagt tgggttgttt gcgcatatct    2520
atcgtggcgt tgggcatgta cgtccgaacg ttgatttgca tgcaagccga aattaaatca    2580
ttgcgattag tgcgattaaa acgttgtaca tcctcgcttt taatcatgcc gtcgattaaa    2640
tcgcgcaatc gagtcaagtg atcaaagtgt ggaataatgt tttctttgta ttcccgagtc    2700
aagcgcagcg cgtattttaa caaactagcc atcttgtaag ttagtttcat ttaatgcaac    2760
tttatccaat aatatattat gtatcgcacg tcaagaatta acaatgcgcc cgttgtcgca    2820
tctcaacacg actatgatag agatcaaata aagcgcgaat aaatagctt gcgacgcaac    2880 gtgcacgatc tgtgcacgcg ttccggcacg agctttgatt gtaataagtt tttacgaagc    2940
gatgacatga cccccgtagt gacaacgatc acgcccaaaa gaactgccga ctacaaaatt    3000
accgagtatg tcggtgacgt taaaactatt aagccatcca atcgaccgtt agtcgaatca    3060
ggaccgctgg tgcgagaagc cgcgaagtat ggcgaatgca tcgtataacg tgtggagtcc    3120
gctcattaga gcgtcatgtt tagacaagaa agctacatat ttaattgatc ccgatgattt    3180
tattgataaa ttgaccctaa ctccatacac ggtattctac aatggcgggg ttttggtcaa    3240
aatttccgga ctgcgattgt acatgctgtt aacggctccg cccactatta atgaaattaa    3300
aaattccaat tttaaaaaac gcagcaagag aaacatttgt atgaaagaat gcgtagaagg    3360
aaagaaaaat gtcgtcgaca tgctgaacaa caagattaat atgcctccgt gtataaaaaa    3420
aatattgaac gatttgaaag aaaacaatgt accgcgcggc ggtatgtaca ggaagaggtt    3480
tatactaaac tgttacattg caaacgtggt ttcgtgtgcc aagtgtgaaa accgatgttt    3540
aatcaaggct ctgacgcatt tctacaacca cgactccaag tgtgtgggtg aagtcatgca    3600
tcttttaatc aaatcccaag atgtgtataa accaccaaac tgccaaaaaa tgaaaactgt    3660
cgacaagctc tgtccgtttg ctggcaactg caagggtctc aatcctatt gtaattattg     3720 aataataaaa caattataaa tgctaaattt gttttttatt aacgatacaa accaaacgca    3780
acaagaacat ttgtagtatt atctataatt gaaaacgcgt agttataatc gctgaggtaa    3840
tatttaaaat cattttcaaa tgattcacag ttaatttgcg acaatataat tttattttca    3900
cataaactag acgccttgtc gtcttcttct tcgtattcct tctctttttc attttctcc     3960 tcataaaaat taacatagtt attatcgtat ccatatatgt atctatcgta tagagtaaat    4020
tttttgttgt cataaatata tatgtctttt ttaatgggt gtatagtacc gctgcgcata    4080
gtttttctgt aatttacaac agtgctattt tctggtagtt cttcggagtg tgttgcttta    4140
attattaaat ttatataatc aatgaatttg ggatcgtcgg ttttgtacaa tatgttgccg    4200
gcatagtacg cagcttcttc tagttcaatt acaccatttt ttagcagcac cggattaaca    4260
taactttcca aaatgttgta cgaaccgtta aacaaaaaca gttcacctcc cttttctata    4320
ctattgtctg cgagcagttg tttgttgtta aaaataacag ccattgtaat gagacgcaca    4380
aactaatatc acaaactgga aatgtctatc aatatatagt tgctgatatc atggagataa    4440
ttaaaatgat aaccatctcg caaataaata agtatttac tgttttcgta acagttttgt     4500
```

-continued

| | | |
|---|---|---|
| aataaaaaaa cctataaata cggatccacc atg gtg agc aag ggc gag gag ctg<br>                                                  Met Val Ser Lys Gly Glu Glu Leu<br>                                                     1             5 | 4554 |
| ttc acc ggg gtg gtg ccc atc ctg gtc gag ctg gac ggc gac gta aac<br>Phe Thr Gly Val Val Pro Ile Leu Val Glu Leu Asp Gly Asp Val Asn<br>      10                        15                        20 | 4602 |
| ggc cac aag ttc agc gtg tcc ggc gag ggc gag ggc gat gcc acc tac<br>Gly His Lys Phe Ser Val Ser Gly Glu Gly Glu Gly Asp Ala Thr Tyr<br>25                       30                        35                        40 | 4650 |
| ggc aag ctg acc ctg aag ttc atc tgc acc acc ggc aag ctg ccc gtg<br>Gly Lys Leu Thr Leu Lys Phe Ile Cys Thr Thr Gly Lys Leu Pro Val<br>                 45                        50                        55 | 4698 |
| ccc tgg ccc acc ctc gtg acc acc ctg acc tac ggc gtg cag tgc ttc<br>Pro Trp Pro Thr Leu Val Thr Thr Leu Thr Tyr Gly Val Gln Cys Phe<br>                       60                        65                        70 | 4746 |
| agc cgc tac ccc gac cac atg aag cag cac gac ttc ttc aag tcc gcc<br>Ser Arg Tyr Pro Asp His Met Lys Gln His Asp Phe Phe Lys Ser Ala<br>          75                        80                        85 | 4794 |
| atg ccc gaa ggc tac gtc cag gag cgc acc atc ttc ttc aag gac gac<br>Met Pro Glu Gly Tyr Val Gln Glu Arg Thr Ile Phe Phe Lys Asp Asp<br>         90                        95                       100 | 4842 |
| ggc aac tac aag acc cgc gcc gag gtg aag ttc gag ggc gac acc ctg<br>Gly Asn Tyr Lys Thr Arg Ala Glu Val Lys Phe Glu Gly Asp Thr Leu<br>105                     110                     115                   120 | 4890 |
| gtg aac cgc atc gag ctg aag ggc atc gac ttc aag gag gac ggc aac<br>Val Asn Arg Ile Glu Leu Lys Gly Ile Asp Phe Lys Glu Asp Gly Asn<br>                 125                     130                   135 | 4938 |
| atc ctg ggg cac aag ctg gag tac aac tac aac agc cac aac gtc tat<br>Ile Leu Gly His Lys Leu Glu Tyr Asn Tyr Asn Ser His Asn Val Tyr<br>               140                     145                   150 | 4986 |
| atc atg gcc gac aag cag aag aac ggc atc aag gtg aac ttc aag atc<br>Ile Met Ala Asp Lys Gln Lys Asn Gly Ile Lys Val Asn Phe Lys Ile<br>         155                       160                      165 | 5034 |
| cgc cac aac atc gag gac ggc agc gtg cag ctc gcc gac cac tac cag<br>Arg His Asn Ile Glu Asp Gly Ser Val Gln Leu Ala Asp His Tyr Gln<br>     170                       175                     180 | 5082 |
| cag aac acc ccc atc ggc gac ggc ccc gtg ctg ctg ccc gac aac cac<br>Gln Asn Thr Pro Ile Gly Asp Gly Pro Val Leu Leu Pro Asp Asn His<br>185                     190                     195                   200 | 5130 |
| tac ctg agc acc cag tcc gcc ctg agc aaa gac ccc aac gag aag cgc<br>Tyr Leu Ser Thr Gln Ser Ala Leu Ser Lys Asp Pro Asn Glu Lys Arg<br>               205                     210                   215 | 5178 |
| gat cac atg gtc ctg ctg gag ttc gtg acc gcc gcc ggg atc act ctc<br>Asp His Met Val Leu Leu Glu Phe Val Thr Ala Ala Gly Ile Thr Leu<br>         220                       225                     230 | 5226 |
| ggc atg gac gag ctg tac aag ggt accacaagtt tgtacaaaaa agctgaacga<br>Gly Met Asp Glu Leu Tyr Lys<br>         235 | 5280 |
| gaaacgtaaa atgatataaa tatcaatata ttaaattaga ttttgcataa aaaacagact | 5340 |
| acataatact gtaaaacaca acatatccag tcactatggc ggccgcatta ggcacccctt | 5400 |
| aggaattcgc ttactaaaag ccagataaca gtatgcgtat ttgcgcgctg attttttgcgg | 5460 |
| tataagaata tatactgata tgtatacccg aagtatgtca aaaagaggtg tgcttctaga | 5520 |
| atgcagttta aggtttacac ctataaaaga gagagccgtt atcgtctgtt tgtggatgta | 5580 |
| cagagtgata ttattgacac gcccgggcga cggatggtga tccccctggc cagtgcacgt | 5640 |
| ctgctgtcag ataaagtctc ccgtgaactt tacccggtgg tgcatatcgg ggatgaaagc | 5700 |
| tggcgcatga tgaccaccga tatggccagt gtgccggtct ccgttatcgg ggaagaagtg | 5760 |

```
gctgatctca gccaccgcga aaatgacatc aaaaacgcca ttaacctgat gttctgggga    5820
atatagaatt cctcaggtcg accatagtga ctggatatgt tgtgttttac agtattatgt    5880
agtctgtttt ttatgcaaaa tctaatttaa tatattgata tttatatcat tttacgtttc    5940
tcgttcagct ttcttgtaca aagtggtctc gagttaatta attgatccgg ttattagta    6000
catttattaa gcgctagatt ctgtgcgttg ttgatttaca gacaattgtt gtacgtattt    6060
taataattca ttaaatttat aatctttagg gtggtatgtt agagcgaaaa tcaaatgatt    6120
ttcagcgtct ttatatctga atttaaatat taaatcctca atagatttgt aaaataggtt    6180
tcgattagtt tcaaacaagg gttgtttttc cgaaccgatg gctggactat ctaatggatt    6240
ttcgctcaac gccacaaaac ttgccaaatc ttgtagcagc aatctagctt tgtcgatatt    6300
cgtttgtgtt ttgttttgta ataaaggttc gacgtcgttc aaaatattat gcgcttttgt    6360
atttctttca tcactgtcgt tagtgtacaa ttgactcgac gtaaacacgt taaataaagc    6420
ttggacatat ttaacatcgg gcgtgttagc tttattaggc cgattatcgt cgtcgtccca    6480
accctcgtcg ttagaagttg cttccgaaga cgattttgcc atagccacac gacgcctatt    6540
aattgtgtcg gctaacacgt ccgcgatcaa atttgtagtt gagcttttg gaattatttc    6600
tgattgcggg cgttttggg cgggtttcaa tctaactgtg cccgatttta attcagacaa    6660
cacgttagaa agcgatggtg caggcggtgg taacatttca gacggcaaat ctactaatgg    6720
cggcggtggt ggagctgatg ataaatctac catcggtgga ggcgcaggcg gggctggcgg    6780
cggaggcgga ggcggaggtg gtggcggtga tgcagacggc ggtttaggct caaatgtctc    6840
tttaggcaac acagtcggca cctcaactat tgtactggtt tcgggcgccg tttttggttt    6900
gaccggtctg agacgagtgc gattttttc gtttctaata gcttccaaca attgttgtct    6960
gtcgtctaaa ggtgcagcgg gttgaggttc cgtcggcatt ggtggagcgg gcggcaattc    7020
agacatcgat ggtggtggtg gtggtggagg cgctggaatg ttaggcacgg gagaaggtgg    7080
tggcggcggt gccgccggta aatttgttc tggtttagtt tgttcgcgca cgattgtggg    7140
caccggcgca ggcgccgctg gctgcacaac ggaaggtcgt ctgcttcgag gcagcgcttg    7200
gggtggtggc aattcaatat tataattgga atacaaatcg taaaaatctg ctataagcat    7260
tgtaatttcg ctatcgttta ccgtgccgat atttaacaac cgctcaatgt aagcaattgt    7320
attgtaaaga gattgtctca agctcggatc ccgcacgccg ataacaagcc ttttcatttt    7380
tactacagca ttgtagtggc gagacacttc gctgtcgtcg acgtacatgt atgctttgtt    7440
gtcaaaaacg tcgttggcaa gctttaaaat atttaaaaga acatctctgt tcagcaccac    7500
tgtgttgtcg taaatgttgt ttttgataat ttgcgcttcc gcagtatcga cacgttcaaa    7560
aaattgatgc gcatcaattt tgttgttcct attattgaat aaataagatt gtacagattc    7620
atatctacga ttcgtcatgg ccaccacaaa tgctacgctg caaacgctgg tacaatttta    7680
cgaaaactgc aaaaacgtca aaactcggta taaaataatc aacgggcgct ttggcaaaat    7740
atctatttta tcgcacaagc ccactagcaa attgtatttg cagaaaacaa tttcggcgca    7800
caatttaac gctgacgaaa taaagttca ccagttaatg agcgaccacc caatttat    7860
aaaaatctat tttaatcacg gttccatcaa caaccaagtg atcgtgatgg actacattga    7920
ctgtcccgat ttatttgaaa cactacaaat taaaggcgag ctttcgtacc aacttgttag    7980
caatattatt agacagctgt gtgaagcgct caacgatttg cacaagcaca atttcataca    8040
caacgacata aaactcgaaa atgtcttata tttcgaagca cttgatcgcg tgtatgtttg    8100
```

-continued

```
cgattacgga ttgtgcaaac acgaaaactc acttagcgtg cacgacggca cgttggagta    8160
ttttagtccg gaaaaaattc gacacacaac tatgcacgtt tcgtttgact ggtacgccgt    8220
cggcgtgtta acatacaagt tgctaaccgg cggccgacac ccatttgaaa aaagcgaaga    8280
cgaaatgttg gacttgaata gcatgaagcg tcgtcagcaa tacaatgaca ttggcgtttt    8340
aaaacacgtt cgtaacgtta acgctcgtga ctttgtgtac tgcctaacaa gatcaaacat    8400
agattgtaga ctcacaaatt acaaacaaat tataaaacat gagtttttgt cgtaaaaatg    8460
ccacttgttt tacgagtaga attctacgtg taacacacga tctaaaagat gatgtcattt    8520
tttatcaatg actcatttgt tttaaaacag acttgtttta cgagtagaat tctacgtgta    8580
aagcatgatc gtgagtggtg ttaataaaat cataaaaatt attgtaaatg tttattattt    8640
aaaaacgatt caaatatata ataaaaacaa tctacatcta tttcttcaca atccataaca    8700
cacaacaggt ccatcaatga gttttgtct ttatccgaca tactatgtgc atgtaacaaa     8760
tcaaatacat cttttaaatt tttatacaca tctttacatt gtctaccaaa atctttaata    8820
accctataac aaggaaaaga cttttcttct tgcgtggttt tgccgcgcag atattgaaat    8880
aaaatgtgca tgcacgacaa cttgtgttta ctaaaatgct ccttgcctat accgcaaaac    8940
cggccataca tttcggcgat tacacgcgga caattgtacg attcgtctac gtgtaaacga    9000
tcatcataat cactcttgcg caaacgaata aattttttca ccgcttccga caacgaggc    9060
accaattcgg cgggcacgct tcgatacatt attctgtgca cataagttac cacacaaaat    9120
ttattgtacc accatccgac aacgtcgtta ttagggttga acacgttggc gatgcgcagc    9180
agtttcccgt ttctcatgaa atattcaaag cggcccaaaa taatttgcaa gcaatccaac    9240
atgtcttgag aaatttctcg ttcaaaattg ttcaaagaga atatctgcca tccgttttga    9300
acgcgcacgc tgacgggaac caccgcatcg atttgctcca cacttcacg gacgttatcg      9360
tcgatgccca tcgtttcgct ggtgctgaac caatgggaaa ggctcttgat ggaatcgccc    9420
gcgtctatca tcttgaccgc ttcgtcaaag gtgcaactgc cgctcttcaa acgccgcata    9480
gcggtcacgt cccgctctat gcacgacata ccgtttacgt acgattctga taggtattcc    9540
tgaactatac ggtaatggtg atacgactcg ccatacacgt cgtgcacctc attgtatta     9600
gcataataat tgtaaattat aactttgca gcgagagaca tgttgtcagt aaagcggtgc     9660
taggctcaat aatactgatg tacaggcacg cgtgctattt atatataatt tcgcaaggag    9720
gggagctgtt atcggttgct attattaaag aatggccgtc tgtttttatc acaagcttgg    9780
cagcctcaac catgaagcgt cgtcattgta aattaaattc tctgcctcaa gaattatttg    9840
acaagattgt cgagtattta tctttatctg attactgcaa tttggtgctt gtctgtaaaa    9900
gaccttctag taaatataac gtgatatttg atagtactaa tcaccaacat ttgaaaggcg    9960
tgtacaaaaa gacagacgtg caaataacaa gctacaacga                          10000
```

<210> SEQ ID NO 6
<211> LENGTH: 21
<212> TYPE: DNA
<213> ORGANISM: Artificial Sequence
<220> FEATURE:
<223> OTHER INFORMATION: Baculo-Forward primer

<400> SEQUENCE: 6
actgttttcg taacagtttt g                                               21

<210> SEQ ID NO 7
<211> LENGTH: 19

```
<212> TYPE: DNA
<213> ORGANISM: Artificial Sequence
<220> FEATURE:
<223> OTHER INFORMATION: Baculo-Reverse primer

<400> SEQUENCE: 7
acaacgcaca gaatctagc                                                  19

<210> SEQ ID NO 8
<211> LENGTH: 14000
<212> TYPE: DNA
<213> ORGANISM: Artificial Sequence
<220> FEATURE:
<223> OTHER INFORMATION: Polyhedrin locus of vBacHTS2
<220> FEATURE:
<221> NAME/KEY: source
<222> LOCATION: (4687)..(11207)
<223> OTHER INFORMATION: F pBACe3.6
<220> FEATURE:
<221> NAME/KEY: misc_feature
<222> LOCATION: (10307)..(10966)
<223> OTHER INFORMATION: F CmR
<220> FEATURE:
<221> NAME/KEY: promoter
<222> LOCATION: (4428)..(4520)
<223> OTHER INFORMATION: F pPolyhedrin
<220> FEATURE:
<221> NAME/KEY: misc_feature
<222> LOCATION: (11220)..(11344)
<223> OTHER INFORMATION: R attR2
<220> FEATURE:
<221> NAME/KEY: misc_feature
<222> LOCATION: (4537)..(4661)
<223> OTHER INFORMATION: F attR1

<400> SEQUENCE: 8
gaattctacc cgtaaagcga gtttagtttt gaaaaacaaa tgacatcatt tgtataatga      60
catcatcccc tgattgtgtt ttacaagtag aattctatcc gtaaagcgag ttcagttttg     120
aaaacaaatg agtcatacct aaacacgtta ataatcttct gatatcagct tatgactcaa     180
gttatgagcc gtgtgcaaaa catgagataa gtttatgaca tcatccactg atcgtgcgtt     240
acaagtagaa ttctactcgt aaagccagtt cggttatgag ccgtgtgcaa acatgacat     300 cagcttatga ctcatacttg attgtgtttt acgcgtagaa ttctactcgt aaagcgagtt     360
cggttatgag ccgtgtgcaa acatgacat cagcttatga gtcataatta atcgtgcgtt     420
acaagtagaa ttctactcgt aaagcgagtt gaaggatcat atttagttgc gtttatgaga     480
taagattgaa agcacgtgta aaatgtttcc cgcgcgttgg cacaactatt tacaatgcgg     540
ccaagttata aaagattcta atctgatatg ttttaaaaca cctttgcggc ccgagttgtt     600
tgcgtacgtg actagcgaag aagatgtgtg gaccgcagaa cagatagtaa aacaaaaccc     660
tagtattgga gcaataatcg atttaaccaa cacgtctaaa tattatgatg gtgtgcattt     720
tttgcgggcg ggcctgttat acaaaaaaat tcaagtacct ggccagactt tgccgcctga     780
aagcatagtt caagaattta ttgacacggt aaaagaattt acagaaaagt gtcccggcat     840
gttggtgggc gtgcactgca cacacggtat taatcgcacc ggttacatgg tgtgcagata     900
tttaatgcac accctgggta ttgcgccgca ggaagccata gatagattcg aaaaagccag     960
aggtcacaaa attgaaagac aaaattacgt tcaagattta ttaatttaat taatattatt    1020
tgcattcttt aacaaatact ttatcctatt ttcaaattgt tgcgcttctt ccagcgaacc    1080
aaaactatgc ttcgcttgct ccgtttagct tgtagccgat cagtggcgtt gttccaatcg    1140
acggtaggat taggccggat attctccacc acaatgttgg caacgttgat gttacgttta    1200
```

-continued

```
tgcttttggt tttccacgta cgtcttttgg ccggtaatag ccgtaaacgt agtgccgtcg    1260
cgcgtcacgc acaacaccgg atgtttgcgc ttgtccgcgg ggtattgaac cgcgcgatcc    1320
gacaaatcca ccactttggc aactaaatcg gtgacctgcg cgtctttttt ctgcattatt    1380
tcgtctttct tttgcatggt ttcctggaag ccggtgtaca tgcggtttag atcagtcatg    1440
acgcgcgtga cctgcaaatc tttggcctcg atctgcttgt ccttgatggc aacgatgcgt    1500
tcaataaact cttgtttttt aacaagttcc tcggtttttt gcgccaccac cgcttgcagc    1560
gcgtttgtgt gctcggtgaa tgtcgcaatc agcttagtca ccaactgttt gctctcctcc    1620
tcccgttgtt tgatcgcggg atcgtacttg ccggtgcaga gcacttgagg aattacttct    1680
tctaaaagcc attcttgtaa ttctatggcg taaggcaatt tggacttcat aatcagctga    1740
atcacgccgg atttagtaat gagcactgta tgcggctgca aatacagcgg gtcgcccctt    1800
ttcacgacgc tgttagaggt agggcccccca ttttggatgg tctgctcaaa taacgatttg    1860
tatttattgt ctacatgaac acgtatagct ttatcacaaa ctgtatattt taaactgtta    1920
gcgacgtcct tggccacgaa cggacctgt tggtcgcgct ctagcacgta ccgcaggttg    1980
aacgtatctt ctccaaattt aaattctcca attttaacgc gagccatttt gatacacgtg    2040
tgtcgatttt gcaacaacta ttgtttttta acgcaaacta aacttattgt ggtaagcaat    2100
aattaaatat gggggaacat gcgccgctac aacactcgtc gttatgaacg cagacggcgc    2160
cggtctcggc gcaagcggct aaaacgtgtt gcgcgttcaa cgcggcaaac atcgcaaaag    2220
ccaatagtac agttttgatt tgcatattaa cggcgatttt ttaaattatc ttatttaata    2280
aatagttatg acgcctacaa ctccccgccc gcgttgactc gctgcacctc gagcagttcg    2340
ttgacgcctt cctccgtgtg gccgaacacg tcgagcgggt ggtcgatgac cagcggcgtg    2400
ccgcacgcga cgcacaagta tctgtacacc gaatgatcgt cgggcgaagg cacgtcggcc    2460
tccaagtggc aatattggca aattcgaaaa tatatacagt tgggttgttt gcgcatatct    2520
atcgtggcgt tgggcatgta cgtccgaacg ttgatttgca tgcaagccga aattaaatca    2580
ttgcgattag tgcgattaaa acgttgtaca tcctcgcttt taatcatgcc gtcgattaaa    2640
tcgcgcaatc gagtcaagtg atcaaagtgt ggaataatgt tttctttgta ttcccgagtc    2700
aagcgcagcg cgtattttaa caaactagcc atcttgtaag ttagtttcat ttaatgcaac    2760
tttatccaat aatatattat gtatcgcacg tcaagaatta acaatgcgcc cgttgtcgca    2820
tctcaacacg actatgatag agatcaaata aagcgcgaat taaatagctt gcgacgcaac    2880
gtgcacgatc tgtgcacgcg ttccggcacg agctttgatt gtaataagtt tttacgaagc    2940
gatgacatga cccccgtagt gacaacgatc acgcccaaaa gaactgccga ctacaaaatt    3000
accgagtatg tcggtgacgt taaaactatt aagccatcca atcgaccgtt agtcgaatca    3060
ggaccgctgg tgcgagaagc cgcgaagtat ggcgaatgca tcgtataacg tgtggagtcc    3120
gctcattaga gcgtcatgtt tagacaagaa agctacatat ttaattgatc ccgatgattt    3180
tattgataaa ttgaccctaa ctccatacac ggtattctac aatggcgggg ttttggtcaa    3240
aatttccgga ctgcgattgt acatgctgtt aacggctccg cccactatta atgaaattaa    3300
aaattccaat tttaaaaaac gcagcaagag aaacatttgt atgaaagaat gcgtagaagg    3360
aaagaaaaat gtcgtcgaca tgctgaacaa caagattaat atgcctccgt gtataaaaaa    3420
aatattgaac gatttgaaag aaaacaatgt accgcgcggc ggtatgtaca ggaagaggtt    3480
tatactaaac tgttacattg caaacgtggt ttcgtgtgcc aagtgtgaaa accgatgttt    3540
aatcaaggct ctgacgcatt tctacaacca cgactccaag tgtgtgggtg aagtcatgca    3600
```

```
tcttttaatc aaatcccaag atgtgtataa accaccaaac tgccaaaaaa tgaaaactgt    3660
cgacaagctc tgtccgtttg ctggcaactg caagggtctc aatcctattt gtaattattg    3720
aataataaaa caattataaa tgctaaattt gttttttatt aacgatacaa accaaacgca    3780
acaagaacat tgtagtatt atctataatt gaaaacgcgt agttataatc gctgaggtaa    3840
tatttaaaat cattttcaaa tgattcacag ttaatttgcg acaatataat tttattttca    3900
cataaactag acgccttgtc gtcttcttct tcgtattcct tctctttttc attttctcc    3960 tcataaaaat taacatagtt attatcgtat ccatatatgt atctatcgta tagagtaaat    4020
tttttgttgt cataaatata tatgtctttt ttaatgggt gtatagtacc gctgcgcata    4080 gttttttctgt aatttacaac agtgctattt tctggtagtt cttcggagtg tgttgcttta    4140
attattaaat ttatataatc aatgaatttg ggatcgtcgg ttttgtacaa tatgttgccg    4200
gcatagtacg cagcttcttc tagttcaatt acaccatttt ttagcagcac cggattaaca    4260
taactttcca aaatgttgta cgaaccgtta acaaaaaca gttcacctcc cttttctata    4320
ctattgtctg cgagcagttg tttgttgtta aaaataacag ccattgtaat gagacgcaca    4380
aactaatatc acaaactgga aatgtctatc aatatatagt tgctgatatc atggagataa    4440
ttaaaatgat aaccatctcg caaataaata agtattttac tgttttcgta acagttttgt    4500 aataaaaaa cctataaata cggatcccgg ggtaccacaa gtttgtacaa aaaagctgaa    4560
cgagaaacgt aaaatgatat aaatatcaat atattaaatt agattttgca taaaaaacag    4620
actacataat actgtaaaac acaacatatc cagtcactat ggcggccgca ttaggcaccc    4680
cttaggtagg gtcaccgtcg acagcgacac acttgcatcg gatgcagccc ggttaacgtg    4740
ccggcacggc ctgggtaacc aggtattttg tccacataac cgtgcgcaaa atgttgtgga    4800
taagcaggac acagcagcaa tccacagcag gcatacaacc gcacaccgag gttactccgt    4860
tctacaggtt acgacgacat gtcaatactt gcccttgaca ggcattgatg gaatcgtagt    4920
ctcacgctga tagtctgatc gacaatacaa gtgggaccgt ggtcccagac cgataatcag    4980
accgacaaca cgagtgggat cgtggtccca gactaataat cagaccgacg atacgagtgg    5040
gaccgtggtc ccagactaat aatcagaccg acgatacgag tgggaccgtg gttccagact    5100
aataatcaga ccgacgatac gagtgggacc gtggtcccag actaataatc agaccgacga    5160
tacgagtggg accatggtcc cagactaata atcagaccga cgatacgagt gggaccgtgg    5220
tcccagtctg attatcagac cgacgatacg agtgggaccg tggtcccaga ctaataatca    5280
gaccgacgat acgagtggga ccgtggtccc agactaataa tcagaccgac gatacgagtg    5340
ggaccgtggt cccagtctga ttatcagacc gacgatacaa gtggaacagt gggcccagag    5400
agaatattca ggccagttat gctttctggc ctgtaacaaa ggacattaag taaagacaga    5460
taaacgtaga ctaaacgtg gtcgcatcag ggtgctggct tttcaagttc cttaagaatg    5520
gcctcaattt tctctataca ctcagttgga acacgagacc tgtccaggtt aagcaccatt    5580
ttatcgccct tatacaatac tgtcgctcca ggagcaaact gatgtcgtga gcttaaacta    5640
gttcttgatg cagatgacgt tttaagcaca gaagttaaaa gagtgataac ttcttcagct    5700
tcaaatatca ccccagcttt tttctgctca tgaaggttag atgcctgctg cttaagtaat    5760
tcctctttat ctgtaaaggc ttttttgaagt gcatcacctg accgggcaga tagttcaccg    5820
gggtgagaaa aaagagcaac aactgattta ggcaatttgg cggtgttgat acagcgggta    5880
ataatcttac gtgaaatatt ttccgcatca gccagcgcag aaatatttcc agcaaattca    5940
```

```
ttctgcaatc ggcttgcata acgctgacca cgttcataag cacttgttgg gcgataatcg    6000
ttacccaatc tggataatgc agccatctgc tcatcatcca gctcgccaac cagaacacga    6060
taatcacttt cggtaagtgc agcagcttta cgacggcgac tcccatcggc aatttctatg    6120
acaccagata ctcttcgacc gaacgccggt gtctgttgac cagtcagtag aaaagaaggg    6180
atgagatcat ccagtgcgtc ctcagtaagc agctcctggt cacgttcatt acctgaccat    6240
acccgagagg tcttctcaac actatcaccc cggagcactt caagagtaaa cttcacatcc    6300
cgaccacata caggcaaagt aatggcatta ccgcgagcca ttactcctac gcgcgcaatt    6360
aacgaatcca ccatcggggc agctggtgtc gataacgaag tatcttcaac cggttgagta    6420
ttgagcgtat gttttggaat aacaggcgca cgcttcatta tctaatctcc cagcgtggtt    6480
taatcagacg atcgaaaatt tcattgcaga caggttccca aatagaaaga gcatttctcc    6540
aggcaccagt tgaagagcgt tgatcaatgg cctgttcaaa acagttctc atccggatct    6600
gacctttacc aacttcatcc gtttcacgta caacattttt tagaaccatg cttccccagg    6660
catcccgaat ttgctcctcc atccacgggg actgagagcc attactattg ctgtatttgg    6720
taagcaaaat acgtacatca ggctcgaacc ctttaagatc aacgttcttg agcagatcac    6780
gaagcatatc gaaaaactgc agtgcggagg tgtagtcaaa caactcagca ggcgtgggaa    6840
caatcagcac atcagcagca catacgacat taatcgtgcc gatacccagg ttaggcgcgc    6900
tgtcaataac tatgacatca tagtcatgag caacagtttc aatggccagt cggagcatca    6960
ggtgtggatc ggtgggcagt ttaccttcat caaatttgcc cattaactca gtttcaatac    7020
ggtgcagagc cagacaggaa ggaataatgt caagccccgg ccagcaagtg ggctttattg    7080
cataagtgac atcgtccttt tccccaagat agaaaggcag gagagtgtct tctgcatgaa    7140
tatgaagatc tggtacccat ccgtgataca ttgaggctgt tccctggggg tcgttacctt    7200
ccacgagcaa aacacgtagc cccttcagag ccagatcctg agcaagatga acagaaactg    7260
aggttttgta acgccacct ttatgggcag caaccccgat caccggtgga aatacgtctt    7320
cagcacgtcg caatcgcgta ccaaacacat cacgcatatg attaatttgt tcaattgtat    7380
aaccaacacg ttgctcaacc cgtcctcgaa tttccatatc cgggtgcggt agtcgccctg    7440
ctttctcggc atctctgata gcctgagaag aaacccaac taaatccgct gcttcaccta    7500
ttctccagcg ccgggttatt ttcctcgctt ccgggctgtc atcattaaac tgtgcaatgg    7560
cgatagcctt cgtcatttca tgaccagcgt ttatgcactg gttaagtgtt tccatgagtt    7620
tcattctgaa catcctttaa tcattgcttt gcgttttttt attaaatctt gcaatttact    7680
gcaaagcaac aacaaaatcg caaagtcatc aaaaaaccgc aaagttgttt aaaataagag    7740
caacactaca aaggagata agaagagcac ataccctcagt cacttattat cactagcgct    7800
cgccgcagcc gtgtaaccga gcatagcgag cgaactggcg aggaagcaaa gaagaactgt    7860
tctgtcagat agctcttacg ctcagcgcaa gaagaaatat ccaccgtggg aaaaactcca    7920
ggtagaggta cacacgcgga tagccaattc agagtaataa actgtgataa tcaaccctca    7980
tcaatgatga cgaactaacc cccgatatca ggtcacatga cgaagggaaa gagaaggaaa    8040
tcaactgtga caaactgccc tcaaatttgg cttccttaaa aattacagtt caaaagtat    8100
gagaaaatcc atgcaggctg aaggaaacag caaaactgtg acaaattacc ctcagtaggt    8160
cagaacaaat gtgacgaacc accctcaaat ctgtgacaga taaccctcag actatcctgt    8220
cgtcatggaa gtgatatcgc ggaaggaaaa tacgatatga gtcgtctggc ggcctttctt    8280
tttctcaatg tatgagaggc gcattggagt tctgctgttg atctcattaa cacagacctg    8340
```

-continued

```
caggaagcgg cggcggaagt caggcatacg ctggtaactt tgaggcagct ggtaacgctc      8400
tatgatccag tcgattttca gagagacgat gcctgagcca tccggcttac gatactgaca      8460
cagggattcg tataaacgca tggcatacgg attggtgatt tcttttgttt cactaagccg      8520
aaactgcgta aaccggttct gtaacccgat aaagaaggga atgagatatg ggttgatatg      8580
tacactgtaa agccctctgg atggactgtg cgcacgtttg ataaaccaag gaaaagattc      8640
atagcctttt tcatcgccgg catcctcttc agggcgataa aaaccactt ccttccccgc       8700 gaaactcttc aatgcctgcc gtatatcctt actggcttcc gcagaggtca atccgaatat      8760
ttcagcatat ttagcaacat ggatctcgca gataccgtca tgttcctgta gggtgccatc      8820
agattttctg atctggtcaa cgaacagata cagcatacgt ttttgatccc gggagagact      8880
atatgccgcc tcagtgaggt cgtttgactg gacgattcgc gggctatttt tacgtttctt      8940
gtgattgata accgctgttt ccgccatgac agatccatgt gaagtgtgac aagtttttag      9000
attgtcacac taaataaaaa agagtcaata agcagggata actttgtgaa aaaacagctt      9060
cttctgaggg caatttgtca cagggttaag ggcaatttgt cacagacagg actgtcattt      9120
gagggtgatt tgtcacactg aaagggcaat ttgtcacaac accttctcta gaaccagcat      9180
ggataaaggc ctacaaggcg ctctaaaaaa gaagatctaa aaactataaa aaaataatt       9240 ataaaaatat ccccgtggat aagtggataa ccccaaggga agttttttca ggcatcgtgt      9300
gtaagcagaa tatataagtg ctgttccctg gtgcttcctc gctcactcga gggcttcgcc      9360
ctgtcgctca actgcggcga gcactactgg ctgtaaaagg acagaccaca tcatggttct      9420
gtgttcatta ggttgttctg tccattgctg acataatccg ctccacttca acgtaacacc      9480
gcacgaagat ttctattgtt cctgaaggca tattcaaatc gttttcgtta ccgcttgcag      9540
gcatcatgac agaacactac ttcctataaa cgctacacag gctcctgaga ttaataatgc      9600
ggatctctac gataatggga gattttcccg actgtttcgt tcgcttctca gtggataaca      9660
gccagcttct ctgtttaaca gacaaaaaca gcatatccac tcagttccac atttccatat      9720
aaaggccaag gcatttattc tcaggataat tgtttcagca tcgcaaccgc atcagactcc      9780
ggcatcgcaa actgcacccg gtgccgggca gccacatcca gcgcaaaaac cttcgtgtag      9840
acttccgttg aactgatgga cttatgtccc atcaggcttt gcagaacttt cagcggtata      9900
ccggcataca gcatgtgcat cgcataggaa tggcggaacg tatgtggtgt gaccggaaca      9960
gagaacgtca caccgtcagc agcagcggcg gcaaccgcct ccccaatcca ggtcctgacc      10020
gttctgtccg tcacttccca gatccgcgct ttctctgtcc ttcctgtgcg acggttacgc      10080
cgctccatga gcttatcgcg aataaatacc tgtgacggaa gatcacttcg cagaataaat      10140
aaatcctggt gtccctgttg ataccgggaa gccctgggcc aacttttggc gaaaatgaga      10200
cgttgatcgg cacgtaagag gttccaactt tcaccataat gaaataagat cactaccggg      10260
cgtatttttt gagttatcga gattttcagg agctaaggaa gctaaaatgg agaaaaaaat      10320
cactggatat accaccgttg atatatccca atggcatcgt aaagaacatt ttgaggcatt      10380
tcagtcagtt gctcaatgta cctataacca gaccgttcag ctggatatta cggcctttttt     10440 aaagaccgta agaaaaata agcacaagtt ttatccggcc tttattcaca ttcttgcccg       10500
cctgatgaat gctcatccgg agttccgtat ggcaatgaaa gacggtgagc tggtgatatg      10560
ggatagtgtt cacccttgtt acaccgtttt ccatgagcaa actgaaacgt tttcatcgct      10620
ctggagtgaa taccacgacg atttccggca gtttctacac atatattcgc aagatgtggc      10680
```

-continued

```
gtgttacggt gaaaacctgg cctatttccc taaagggttt attgagaata tgttttcgt    10740
ctcagccaat ccctgggtga gtttcaccag ttttgattta aacgtggcca atatggacaa   10800
cttcttcgcc cccgttttca ccatgggcaa atattatacg caaggcgaca aggtgctgat   10860
gccgctggcg attcaggttc atcatgccgt ttgtgatggc ttccatgtcg gcagaatgct   10920
taatgaatta caacagtact gcgatgagtg gcagggcggg gcgtaatttt tttaaggcag   10980
ttattggtgc ccttaaacgc ctggttgcta cgcctgaata agtgataata agcggatgaa   11040
tggcagaaat tcgatgataa gctgtcaaac atgagaattg gtcgacggcg cgccaaagct   11100
tgcatgcctg cagccgcgta acctggcaaa tcggttacg gttgagtaat aaatggatgc    11160
cctgcgtaag cggggcacat ttcattacct ctttctccgc acccgaccct caggtcgacc   11220
atagtgactg gatatgttgt gttttacagt attatgtagt ctgttttta tgcaaaatct    11280
aatttaatat attgatattt atatcatttt acgtttctcg ttcagctttc ttgtacaaag   11340
tggtctcgag ttaattaatt gatccggtt attagtacat ttattaagcg ctagattctg    11400
tgcgttgttg atttacagac aattgttgta cgtattttaa taattcatta aatttataat   11460
ctttaggtg gtatgttaga gcgaaaatca aatgattttc agcgtcttta tatctgaatt    11520
taaatattaa atcctcaata gatttgtaaa ataggtttcg attagtttca aacaagggtt   11580
gtttttccga accgatggct ggactatcta atggattttc gctcaacgcc acaaaacttg   11640
ccaaatcttg tagcagcaat ctagctttgt cgatattcgt ttgtgttttg ttttgtaata   11700
aaggttcgac gtcgttcaaa atattatgcg cttttgtatt tctttcatca ctgtcgttag   11760
tgtacaattg actcgacgta aacacgttaa ataaagcttg gacatattta acatcgggcg   11820
tgttagcttt attaggccga ttatcgtcgt cgtcccaacc ctcgtcgtta gaagttgctt   11880
ccgaagacga ttttgccata gccacacgac gcctattaat tgtgtcggct aacacgtccg   11940
cgatcaaatt tgtagttgag ctttttggaa ttatttctga ttgcgggcgt ttttgggcgg   12000
gtttcaatct aactgtgccc gattttaatt cagacaacac gttagaaagc gatggtgcag   12060
gcggtggtaa catttcagac ggcaaatcta ctaatggcgg cggtggtgga gctgatgata   12120
aatctaccat cggtggaggc gcaggcgggg ctggcggcgg aggcggaggc ggaggtggtg   12180
gcggtgatgc agacggcggt ttaggctcaa atgtctcttt aggcaacaca gtcggcacct   12240
caactattgt actggtttcg ggcgccgttt ttggtttgac cggtctgaga cgagtgcgat   12300
ttttttcgtt tctaatagct tccaacaatt gttgtctgtc gtctaaaggt gcagcgggtt   12360
gaggttccgt cggcattggt ggagcgggcg gcaattcaga catcgatggt ggtggtggtg   12420
gtggaggcgc tggaatgtta ggcacggag aaggtggtgg cggcggtgcc gccggtataa    12480
tttgttctgg tttagtttgt tcgcgcacga ttgtgggcac cggcgcaggc gccgctggct   12540
gcacaacgga aggtcgtctg cttcgaggca gcgcttgggg tggtggcaat tcaatattat   12600
aattggaata caaatcgtaa aaatctgcta taagcattgt aatttcgcta tcgtttaccg   12660
tgccgatatt taacaaccgc tcaatgtaag caattgtatt gtaaagagat tgtctcaagc   12720
tcggatcccg cacgccgata acaagccttt tcatttttac tacagcattg tagtggcgag   12780
acacttcgct gtcgtcgacg tacatgtatg ctttgttgtc aaaaacgtcg ttggcaagct   12840
ttaaaatatt taaagaaca tctctgttca gcaccactgt gttgtcgtaa atgttgtttt    12900
tgataatttg cgcttccgca gtatcgacac gttcaaaaaa ttgatgcgca tcaatttgt    12960
tgttcctatt attgaataaa taagattgta cagattcata tctacgattc gtcatggcca   13020
ccacaaatgc tacgctgcaa acgctggtac aattttacga aaactgcaaa aacgtcaaaa   13080
```

-continued

```
ctcggtataa aataatcaac gggcgctttg gcaaaatatc tattttatcg cacaagccca    13140
ctagcaaatt gtatttgcag aaaacaattt cggcgcacaa ttttaacgct gacgaaataa    13200
aagttcacca gttaatgagc gaccacccaa attttataaa aatctatttt aatcacggtt    13260
ccatcaacaa ccaagtgatc gtgatggact acattgactg tcccgattta tttgaaacac    13320
tacaaattaa aggcgagctt tcgtaccaac ttgttagcaa tattattaga cagctgtgtg    13380
aagcgctcaa cgatttgcac aagcacaatt tcatacacaa cgacataaaa ctcgaaaatg    13440
tcttatattt cgaagcactt gatcgcgtgt atgtttgcga ttacggattg tgcaaacacg    13500
aaaactcact tagcgtgcac gacggcacgt tggagtattt tagtccggaa aaaattcgac    13560
acacaactat gcacgtttcg tttgactggt acgccgtcgg cgtgttaaca tacaagttgc    13620
taaccggcgg ccgacaccca tttgaaaaaa gcgaagacga aatgttggac ttgaatagca    13680
tgaagcgtcg tcagcaatac aatgacattg gcgttttaaa acacgttcgt aacgttaacg    13740
ctcgtgactt tgtgtactgc ctaacaagat acaacataga ttgtagactc acaaattaca    13800
aacaaattat aaaacatgag ttttttgtcgt aaaaatgcca cttgttttac gagtagaatt    13860
ctacgtgtaa cacacgatct aaaagatgat gtcattttttt atcaatgact catttgtttt    13920 aaacagact tgttttacga gtagaattct acgtgtaaag catgatcgtg agtggtgtta    13980 taaaatcat aaaaattatt                                                 14000
```

<210> SEQ ID NO 9
<211> LENGTH: 13100
<212> TYPE: DNA
<213> ORGANISM: Artificial Sequence
<220> FEATURE:
<223> OTHER INFORMATION: Polyhedrin locus of vBacHTS2_GFP
<220> FEATURE:
<221> NAME/KEY: source
<222> LOCATION: (4523)..(5252)
<223> OTHER INFORMATION: F EGFP
<220> FEATURE:
<221> NAME/KEY: source
<222> LOCATION: (5404)..(11924)
<223> OTHER INFORMATION: F pBACe3.6
<220> FEATURE:
<221> NAME/KEY: CDS
<222> LOCATION: (4531)..(5247)
<223> OTHER INFORMATION: F EGFP
<220> FEATURE:
<221> NAME/KEY: misc_feature
<222> LOCATION: (11024)..(11683)
<223> OTHER INFORMATION: F CmR
<220> FEATURE:
<221> NAME/KEY: promoter
<222> LOCATION: (4428)..(4520)
<223> OTHER INFORMATION: F pPolyhedrin
<220> FEATURE:
<221> NAME/KEY: misc_feature
<222> LOCATION: (11937)..(12061)
<223> OTHER INFORMATION: R attR2
<220> FEATURE:
<221> NAME/KEY: misc_feature
<222> LOCATION: (5254)..(5378)
<223> OTHER INFORMATION: F attR1

<400> SEQUENCE: 9

```
gaattctacc cgtaaagcga gtttagtttt gaaaaacaaa tgacatcatt tgtataatga      60
catcatcccc tgattgtgtt ttacaagtag aattctatcc gtaaagcgag ttcagttttg     120
aaaacaaatg agtcataccct aaacacgtta ataatcttct gatatcagct tatgactcaa    180
gttatgagcc gtgtgcaaaa catgagataa gtttatgaca tcatccactg atcgtgcgtt    240
```

-continued

```
acaagtagaa ttctactcgt aaagccagtt cggttatgag ccgtgtgcaa aacatgacat    300
cagcttatga ctcatacttg attgtgtttt acgcgtagaa ttctactcgt aaagcgagtt    360
cggttatgag ccgtgtgcaa aacatgacat cagcttatga gtcataatta atcgtgcgtt    420
acaagtagaa ttctactcgt aaagcgagtt gaaggatcat atttagttgc gtttatgaga    480
taagattgaa agcacgtgta aaatgtttcc cgcgcgttgg cacaactatt tacaatgcgg    540
ccaagttata aagattcta atctgatatg ttttaaaaca cctttgcggc ccgagttgtt    600
tgcgtacgtg actagcgaag aagatgtgtg gaccgcagaa cagatagtaa aacaaaaccc    660
tagtattgga gcaataatcg atttaaccaa cacgtctaaa tattatgatg gtgtgcattt    720
tttgcgggcg ggcctgttat acaaaaaaat tcaagtacct ggccagactt tgccgcctga    780
aagcatagtt caagaattta ttgacacggt aaaagaattt acagaaaagt gtcccggcat    840
gttggtgggc gtgcactgca cacacggtat taatcgcacc ggttacatgg tgtgcagata    900
tttaatgcac accctgggta ttgcgccgca ggaagccata gatagattcg aaaaagccag    960
aggtcacaaa attgaaagac aaaattacgt tcaagattta ttaatttaat taatattatt   1020
tgcattcttt aacaaatact ttatcctatt ttcaaattgt tgcgcttctt ccagcgaacc   1080
aaaactatgc ttcgcttgct ccgtttagct tgtagccgat cagtggcgtt gttccaatcg   1140
acggtaggat taggccggat attctccacc acaatgttgg caacgttgat gttacgttta   1200
tgcttttggt tttccacgta cgtcttttgg ccggtaatag ccgtaaacgt agtgccgtcg   1260
cgcgtcacgc acaacaccgg atgtttgcgc ttgtccgcgg ggtattgaac cgcgcgatcc   1320
gacaaatcca ccactttggc aactaaatcg gtgacctgcg cgtctttttt ctgcattatt   1380
tcgtctttct tttgcatggt ttcctggaag ccggtgtaca tgcggtttag atcagtcatg   1440
acgcgcgtga cctgcaaatc tttggcctcg atctgcttgt ccttgatggc aacgatgcgt   1500
tcaataaact cttgtttttt aacaagttcc tcggtttttt gcgccaccac cgcttgcagc   1560
gcgtttgtgt gctcggtgaa tgtcgcaatc agcttagtca ccaactgttt gctctcctcc   1620
tcccgttgtt tgatcgcggg atcgtacttg ccggtgcaga gcacttgagg aattacttct   1680
tctaaaagcc attcttgtaa ttctatggcg taaggcaatt tggacttcat aatcagctga   1740
atcacgccgg atttagtaat gagcactgta tgcggctgca aatacagcgg gtcgcccctt   1800
ttcacgacgc tgttagaggt agggccccca ttttggatgg tctgctcaaa taacgatttg   1860
tatttattgt ctacatgaac acgtatagct ttatcacaaa ctgtatattt taaactgtta   1920
gcgacgtcct tggccacgaa ccggaccttgt ggtcgcgct ctagcacgta ccgcaggttg   1980
aacgtatctt ctccaaattt aaattctcca attttaacgc gagccatttt gatacacgtg   2040
tgtcgatttt gcaacaacta ttgtttttta acgcaaacta aacttattgt ggtaagcaat   2100
aattaaatat gggggaacat gcgccgctac aacactcgtc gttatgaacg cagacggcgc   2160
cggtctcggc gcaagcggct aaaacgtgtt gcgcgttcaa cgcggcaaac atcgcaaaag   2220
ccaatagtac agttttgatt tgcatattaa cggcgatttt ttaaattatc ttatttaata   2280
aatagttatg acgcctacaa ctccccgccc gcgttgactc gctgcacctc gagcagttcg   2340
ttgacgcctt cctccgtgtg gccgaacacg tcgagcgggt ggtcgatgac cagcggcgtg   2400
ccgcacgcga cgcacaagta tctgtacacc gaatgatcgt cgggcgaagg cacgtcggcc   2460
tccaagtggc aatattggca aattcgaaaa tatatacagt tgggttgttt gcgcatatct   2520
atcgtggcgt tgggcatgta cgtccgaacg ttgatttgca tgcaagccga aattaaatca   2580
ttgcgattag tgcgattaaa acgttgtaca tcctcgcttt taatcatgcc gtcgattaaa   2640
```

-continued

```
tcgcgcaatc gagtcaagtg atcaaagtgt ggaataatgt tttctttgta ttcccgagtc      2700
aagcgcagcg cgtattttaa caaactagcc atcttgtaag ttagtttcat ttaatgcaac      2760
tttatccaat aatatattat gtatcgcacg tcaagaatta acaatgcgcc cgttgtcgca      2820
tctcaacacg actatgatag agatcaaata aagcgcgaat taaatagctt gcgacgcaac      2880
gtgcacgatc tgtgcacgcg ttccggcacg agctttgatt gtaataagtt tttacgaagc      2940
gatgacatga cccccgtagt gacaacgatc acgcccaaaa gaactgccga ctacaaaatt      3000
accgagtatg tcggtgacgt taaaactatt aagccatcca atcgaccgtt agtcgaatca      3060
ggaccgctgg tgcgagaagc cgcgaagtat ggcgaatgca tcgtataacg tgtggagtcc      3120
gctcattaga gcgtcatgtt tagacaagaa agctacatat ttaattgatc ccgatgattt      3180
tattgataaa ttgaccctaa ctccatacac ggtattctac aatggcgggg ttttggtcaa      3240
aatttccgga ctgcgattgt acatgctgtt aacggctccg cccactatta atgaaattaa      3300
aaattccaat tttaaaaaac gcagcaagag aaacatttgt atgaaagaat gcgtagaagg      3360
aaagaaaaat gtcgtcgaca tgctgaacaa caagattaat atgcctccgt gtataaaaaa      3420
aatattgaac gatttgaaag aaaacaatgt accgcgcggc ggtatgtaca ggaagaggtt      3480
tatactaaac tgttacattg caaacgtggt tcgtgtgcc aagtgtgaaa accgatgttt       3540
aatcaaggct ctgacgcatt tctacaacca cgactccaag tgtgtgggtg aagtcatgca      3600
tcttttaatc aaatcccaag atgtgtataa accaccaaac tgccaaaaaa tgaaaactgt      3660
cgacaagctc tgtccgtttg ctggcaactg caagggtctc aatcctattt gtaattattg      3720
aataataaaa caattataaa tgctaaattt gtttttttatt aacgatacaa accaaacgca      3780
acaagaacat ttgtagtatt atctataatt gaaaacgcgt agttataatc gctgaggtaa      3840
tatttaaaat cattttcaaa tgattcacag ttaatttgcg acaatataat tttatttttca     3900 cataaactag acgccttgtc gtcttcttct tcgtattcct tctctttttc attttttctcc     3960 tcataaaaat taacatagtt attatcgtat ccatatatgt atctatcgta tagagtaaat      4020 ttttttgttgt cataaatata tatgtctttt ttaatggggt gtatagtacc gctgcgcata     4080
gtttttctgt aatttacaac agtgctattt tctggtagtt cttcggagtg tgttgcttta     4140
attattaaat ttatataatc aatgaatttg ggatcgtcgg ttttgtacaa tatgttgccg      4200
gcatagtacg cagcttcttc tagttcaatt acaccatttt ttagcagcac cggattaaca      4260
taactttcca aaatgttgta cgaaccgtta aacaaaaaca gttcacctcc cttttctata     4320
ctattgtctg cgagcagttg tttgttgtta aaaataacag ccattgtaat gagacgcaca      4380
aactaatatc acaaactgga aatgtctatc aatatatagt tgctgatatc atggagataa      4440
ttaaaatgat aaccatctcg caaataaata agtatttac tgttttcgta acagttttgt       4500
aataaaaaaa cctataaata cggatccacc atg gtg agc aag ggc gag gag ctg      4554
                                    Met Val Ser Lys Gly Glu Glu Leu
                                      1               5 ttc acc ggg gtg gtg ccc atc ctg gtc gag ctg gac ggc gac gta aac       4602
Phe Thr Gly Val Val Pro Ile Leu Val Glu Leu Asp Gly Asp Val Asn
         10                  15                  20 ggc cac aag ttc agc gtg tcc ggc gag ggc gag ggc gat gcc acc tac       4650
Gly His Lys Phe Ser Val Ser Gly Glu Gly Glu Gly Asp Ala Thr Tyr
 25                  30                  35                  40 ggc aag ctg acc ctg aag ttc atc tgc acc acc ggc aag ctg ccc gtg       4698
Gly Lys Leu Thr Leu Lys Phe Ile Cys Thr Thr Gly Lys Leu Pro Val
             45                  50                  55
```

-continued

| | | |
|---|---|---|
| ccc tgg ccc acc ctc gtg acc acc ctg acc tgg ggc gtg cag tgc ttc<br>Pro Trp Pro Thr Leu Val Thr Thr Leu Thr Trp Gly Val Gln Cys Phe<br>60                  65                  70 | | 4746 |
| agc cgc tac ccc gac cac atg aag cag cac gac ttc ttc aag tcc gcc<br>Ser Arg Tyr Pro Asp His Met Lys Gln His Asp Phe Phe Lys Ser Ala<br>    75                  80                  85 | | 4794 |
| atg ccc gaa ggc tac gtc cag gag cgc acc atc ttc ttc aag gac gac<br>Met Pro Glu Gly Tyr Val Gln Glu Arg Thr Ile Phe Phe Lys Asp Asp<br>90                  95                  100 | | 4842 |
| ggc aac tac aag acc cgc gcc gag gtg aag ttc gag ggc gac acc ctg<br>Gly Asn Tyr Lys Thr Arg Ala Glu Val Lys Phe Glu Gly Asp Thr Leu<br>105                 110                 115                 120 | | 4890 |
| gtg aac cgc atc gag ctg aag ggc atc gac ttc aag gag gac ggc aac<br>Val Asn Arg Ile Glu Leu Lys Gly Ile Asp Phe Lys Glu Asp Gly Asn<br>                125                 130                 135 | | 4938 |
| atc ctg ggg cac aag ctg gag tac aac tac aac agc cac aac gtc tat<br>Ile Leu Gly His Lys Leu Glu Tyr Asn Tyr Asn Ser His Asn Val Tyr<br>            140                 145                 150 | | 4986 |
| atc atg gcc gac aag cag aag aac ggc atc aag gtg aac ttc aag atc<br>Ile Met Ala Asp Lys Gln Lys Asn Gly Ile Lys Val Asn Phe Lys Ile<br>        155                 160                 165 | | 5034 |
| cgc cac aac atc gag gac ggc agc gtg cag ctc gcc gac cac tac cag<br>Arg His Asn Ile Glu Asp Gly Ser Val Gln Leu Ala Asp His Tyr Gln<br>    170                 175                 180 | | 5082 |
| cag aac acc ccc atc ggc gac ggc ccc gtg ctg ctg ccc gac aac cac<br>Gln Asn Thr Pro Ile Gly Asp Gly Pro Val Leu Leu Pro Asp Asn His<br>185                 190                 195                 200 | | 5130 |
| tac ctg agc acc cag tcc gcc ctg agc aaa gac ccc aac gag aag cgc<br>Tyr Leu Ser Thr Gln Ser Ala Leu Ser Lys Asp Pro Asn Glu Lys Arg<br>                205                 210                 215 | | 5178 |
| gat cac atg gtc ctg ctg gag ttc gtg acc gcc gcc ggg atc act ctc<br>Asp His Met Val Leu Leu Glu Phe Val Thr Ala Ala Gly Ile Thr Leu<br>            220                 225                 230 | | 5226 |
| ggc atg gac gag ctg tac aag  ggt accacaagtt tgtacaaaaa agctgaacga<br>Gly Met Asp Glu Leu Tyr Lys<br>        235 | | 5280 |
| gaaacgtaaa atgatataaa tatcaatata ttaaattaga ttttgcataa aaaacagact | | 5340 |
| acataatact gtaaaacaca acatatccag tcactatggc ggccgcatta ggcacccctt | | 5400 |
| aggtagggtc accgtcgaca gcgacacact tgcatcggat gcagcccggt taacgtgccg | | 5460 |
| gcacggcctg ggtaaccagg tattttgtcc acataaccgt gcgcaaaatg ttgtggataa | | 5520 |
| gcaggacaca gcagcaatcc acagcaggca tacaaccgca caccgaggtt actccgttct | | 5580 |
| acaggttacg acgacatgtc aatacttgcc cttgacaggc attgatggaa tcgtagtctc | | 5640 |
| acgctgatag tctgatcgac aatacaagtg ggaccgtggt cccagaccga taatcagacc | | 5700 |
| gacaacacga gtgggatcgt ggtcccagac taataatcag accgacgata cgagtgggac | | 5760 |
| cgtggtccca gactaataat cagaccgacg atacgagtgg gaccgtggtt ccagactaat | | 5820 |
| aatcagaccg acgatacgag tgggaccgtg gtcccagact aataatcaga ccgacgatac | | 5880 |
| gagtgggacc atggtcccag actaataatc agaccgacga tacgagtggg accgtggtcc | | 5940 |
| cagtctgatt atcagaccga cgatacgagt gggaccgtgg tcccagacta ataatcagac | | 6000 |
| cgacgatacg agtgggaccg tggtcccaga ctaataatca gaccgacgat acgagtggga | | 6060 |
| ccgtggtccc agtctgatta tcagaccgac gatacaagtg gaacagtggg cccagagaga | | 6120 |
| atattcaggc cagttatgct ttctggcctg taacaaagga cattaagtaa agacagtaaa | | 6180 |
| acgtagacta aaacgtggtc gcatcagggt gctggctttt caagttcctt aagaatggcc | | 6240 |

```
tcaattttct ctatacactc agttggaaca cgagacctgt ccaggttaag caccatttta    6300
tcgcccttat acaatactgt cgctccagga gcaaactgat gtcgtgagct taaactagtt    6360
cttgatgcag atgacgtttt aagcacagaa gttaaaagag tgataacttc ttcagcttca    6420
aatatcaccc cagctttttt ctgctcatga aggttagatg cctgctgctt aagtaattcc    6480
tctttatctg taaaggcttt ttgaagtgca tcacctgacc gggcagatag ttcaccgggg    6540
tgagaaaaaa gagcaacaac tgatttaggc aatttggcgg tgttgataca gcgggtaata    6600
atcttacgtg aaatattttc cgcatcagcc agcgcagaaa tatttccagc aaattcattc    6660
tgcaatcggc ttgcataacg ctgaccacgt tcataagcac ttgttgggcg ataatcgtta    6720
cccaatctgg ataatgcagc catctgctca tcatccagct cgccaaccag aacacgataa    6780
tcactttcgg taagtgcagc agctttacga cggcgactcc catcggcaat ttctatgaca    6840
ccagatactc ttcgaccgaa cgccggtgtc tgttgaccag tcagtagaaa agaagggatg    6900
agatcatcca gtgcgtcctc agtaagcagc tcctggtcac gttcattacc tgaccatacc    6960
cgagaggtct tctcaacact atcaccccgg agcacttcaa gagtaaactt cacatcccga    7020
ccacatacag gcaaagtaat ggcattaccg cgagccatta ctcctacgcg cgcaattaac    7080
gaatccacca tcggggcagc tggtgtcgat aacgaagtat cttcaaccgg ttgagtattg    7140
agcgtatgtt ttggaataac aggcgcacgc ttcattatct aatctcccag cgtggtttaa    7200
tcagacgatc gaaaatttca ttgcagacag gttcccaaat agaaagagca tttctccagg    7260
caccagttga agagcgttga tcaatggcct gttcaaaaac agttctcatc cggatctgac    7320
ctttaccaac ttcatccgtt tcacgtacaa cattttttag aaccatgctt ccccaggcat    7380
cccgaatttg ctcctccatc cacggggact gagagccatt actattgctg tatttggtaa    7440
gcaaatacg tacatcaggc tcgaacccttt taagatcaac gttcttgagc agatcacgaa    7500
gcatatcgaa aaactgcagt gcggaggtgt agtcaaacaa ctcagcaggc gtgggaacaa    7560
tcagcacatc agcagcacat acgacattaa tcgtgccgat acccaggtta ggcgcgctgt    7620
caataactat gacatcatag tcatgagcaa cagtttcaat ggccagtcgg agcatcaggt    7680
gtggatcggt gggcagttta ccttcatcaa atttgcccat taactcagtt tcaatacggt    7740
gcagagccag acaggaagga ataatgtcaa gccccggcca gcaagtgggc tttattgcat    7800
aagtgacatc gtcctttttcc ccaagataga aaggcaggag agtgtcttct gcatgaatat    7860
gaagatctgg tacccatccg tgatacattg aggctgttcc ctgggggtcg ttaccttcca    7920
cgagcaaaac acgtagcccc ttcagagcca gatcctgagc aagatgaaca gaaactgagg    7980
ttttgtaaac gccaccttta tgggcagcaa ccccgatcac cggtggaaat acgtcttcag    8040
cacgtcgcaa tcgcgtacca aacacatcac gcatatgatt aatttgttca attgtataac    8100
caacacgttg ctcaacccgt cctcgaattt ccatatccgg gtgcggtagt cgccctgctt    8160
tctcggcatc tctgatagcc tgagaagaaa ccccaactaa atccgctgct tcacctattc    8220
tccagcgccg ggttatttc ctcgcttccg ggctgtcatc attaaactgt gcaatggcga    8280
tagccttcgt catttcatga ccagcgttta tgcactggtt aagtgtttcc atgagtttca    8340
ttctgaacat cctttaatca ttgctttgcg ttttttttatt aaatcttgca atttactgca    8400
aagcaacaac aaaatcgcaa agtcatcaaa aaaccgcaaa gttgtttaaa ataagagcaa    8460
cactacaaaa ggagataaga agagcacata cctcagtcac ttattatcac tagcgctcgc    8520
cgcagccgtg taaccgagca tagcgagcga actggcgagg aagcaaagaa gaactgttct    8580
```

```
gtcagatagc tcttacgctc agcgcaagaa gaaatatcca ccgtgggaaa aactccaggt   8640
agaggtacac acgcggatag ccaattcaga gtaataaact gtgataatca accctcatca   8700
atgatgacga actaaccccc gatatcaggt cacatgacga agggaaagag aaggaaatca   8760
actgtgacaa actgccctca aatttggctt ccttaaaaat tacagttcaa aaagtatgag   8820
aaaatccatg caggctgaag gaaacagcaa aactgtgaca aattaccctc agtaggtcag   8880
aacaaatgtg acgaaccacc ctcaaatctg tgacagataa ccctcagact atcctgtcgt   8940
catggaagtg atatcgcgga aggaaaatac gatatgagtc gtctggcggc ctttcttttt   9000
ctcaatgtat gagaggcgca ttggagttct gctgttgatc tcattaacac agacctgcag   9060
gaagcggcgg cggaagtcag gcatacgctg gtaactttga ggcagctggt aacgctctat   9120
gatccagtcg attttcagag agacgatgcc tgagccatcc ggcttacgat actgacacag   9180
ggattcgtat aaacgcatgg catacggatt ggtgatttct tttgtttcac taagccgaaa   9240
ctgcgtaaac cggttctgta acccgataaa gaagggaatg agatatgggt tgatatgtac   9300
actgtaaagc cctctggatg gactgtgcgc acgtttgata aaccaaggaa aagattcata   9360 gccttttca tcgccggcat cctcttcagg gcgataaaaa accacttcct tccccgcgaa   9420
actcttcaat gcctgccgta tatccttact ggcttccgca gaggtcaatc cgaatatttc   9480
agcatattta gcaacatgga tctcgcagat accgtcatgt tcctgtaggg tgccatcaga   9540
ttttctgatc tggtcaacga acagatacag catacgtttt tgatcccggg agagactata   9600
tgccgcctca gtgaggtcgt ttgactggac gattcgcggg ctattttac gtttcttgtg   9660 attgataacc gctgtttccg ccatgacaga tccatgtgaa gtgtgacaag tttttagatt   9720
gtcacactaa ataaaaaga gtcaataagc agggataact ttgtgaaaaa acagcttctt   9780
ctgagggcaa tttgtcacag ggttaagggc aatttgtcac agacaggact gtcatttgag   9840
ggtgatttgt cacactgaaa gggcaatttg tcacaacacc ttctctagaa ccagcatgga   9900
taaaggccta caaggcgctc taaaaagaa gatctaaaaa ctataaaaaa ataattata   9960 aaatatcccc cgtggataag tggataaccc caagggaagt tttttcaggc atcgtgtgta  10020
agcagaatat ataagtgctg ttccctggtg cttcctcgct cactcgaggg cttcgccctg  10080
tcgctcaact gcggcgagca ctactggctg taaaaggaca gaccacatca tggttctgtg  10140
ttcattaggt tgttctgtcc attgctgaca taatccgctc cacttcaacg taacaccgca  10200
cgaagatttc tattgttcct gaaggcatat tcaaatcgtt ttcgttaccg cttgcaggca  10260
tcatgacaga acactacttc ctataaacgc tacacaggcc cctgagatta ataatgcgga  10320
tctctacgat aatgggagat tttcccgact gtttcgttcg cttctcagtg gataacagcc  10380
agcttctctg tttaacagac aaaaacagca tatccactca gttccacatt tccatataaa  10440
ggccaaggca tttattctca ggataattgt ttcagcatcg caaccgcatc agactccggc  10500
atcgcaaact gcacccggtg ccgggcagcc acatccagcg caaaaacctt cgtgtagact  10560
tccgttgaac tgatggactt atgtcccatc aggctttgca gaactttcag cggtataccg  10620
gcatacagca tgtgcatcgc ataggaatgg cggaacgtat gtggtgtgac cggaacagag  10680
aacgtcacac cgtcagcagc agcggcggca accgcctccc caatccaggt cctgaccgtt  10740
ctgtccgtca cttcccagat ccgcgctttc tctgtccttc ctgtgcgacg gttacgccgc  10800
tccatgagct tatcgcgaat aaatacctgt gacggaagat cacttcgcag aataaataaa  10860
tcctggtgtc cctgttgata ccggaagcc ctgggccaac ttttggcgaa aatgagacgt  10920
tgatcggcac gtaagaggtt ccaactttca ccataatgaa ataagatcac taccgggcgt  10980
```

```
atttttttgag ttatcgagat tttcaggagc taaggaagct aaaatgggaga aaaaaatcac   11040
tggatatacc accgttgata tatcccaatg gcatcgtaaa gaacattttg aggcatttca   11100
gtcagttgct caatgtacct ataaccagac cgttcagctg gatattacgg cctttttaaa   11160
gaccgtaaag aaaaataagc acaagtttta tccggccttt attcacattc ttgcccgcct   11220
gatgaatgct catccggagt tccgtatggc aatgaaagac ggtgagctgg tgatatggga   11280
tagtgttcac ccttgttaca ccgttttcca tgagcaaact gaaacgtttt catcgctctg   11340
gagtgaatac cacgacgatt tccggcagtt tctacacata tattcgcaag atgtggcgtg   11400
ttacggtgaa aacctggcct atttccctaa agggtttatt gagaatatgt ttttcgtctc   11460
agccaatccc tgggtgagtt tcaccagttt tgatttaaac gtggccaata tggacaactt   11520
cttcgccccc gttttcacca tgggcaaata ttatacgcaa ggcgacaagg tgctgatgcc   11580
gctggcgatt caggttcatc atgccgtttg tgatggcttc catgtcggca gaatgcttaa   11640
tgaattacaa cagtactgcg atgagtggca gggcggggcg taatttttt aaggcagtta   11700
ttggtgccct taaacgcctg gttgctacgc ctgaataagt gataataagc ggatgaatgg   11760
cagaaattcg atgataagct gtcaaacatg agaattggtc gacggcgcgc caaagcttgc   11820
atgcctgcag ccgcgtaacc tggcaaaatc ggttacggtt gagtaataaa tggatgccct   11880
gcgtaagcgg ggcacatttc attacctctt tctccgcacc cgaccctcag gtcgaccata   11940
gtgactggat atgttgtgtt ttacagtatt atgtagtctg ttttttatgc aaaatctaat   12000
ttaatatatt gatatttata tcattttacg tttctcgttc agctttcttg tacaaagtgg   12060
tctcgagtta attaattgat ccgggttatt agtacattta ttaagcgcta gattctgtgc   12120
gttgttgatt tacagacaat tgttgtacgt atttaataa ttcattaaat ttataatctt   12180
tagggtggta tgttagagcg aaaatcaaat gattttcagc gtctttatat ctgaatttaa   12240
atattaaatc ctcaatagat ttgtaaaata ggtttcgatt agtttcaaac aagggttgtt   12300
tttccgaacc gatggctgga ctatctaatg gattttcgct caacgccaca aaacttgcca   12360
aatcttgtag cagcaatcta gctttgtcga tattcgtttg tgttttgttt tgtaataaag   12420
gttcgacgtc gttcaaaata ttatgcgctt ttgtatttct ttcatcactg tcgttagtgt   12480
acaattgact cgacgtaaac acgttaaata aagcttggac atatttaaca tcgggcgtgt   12540
tagctttatt aggccgatta tcgtcgtcgt cccaaccctc gtcgttagaa gttgcttccg   12600
aagacgattt tgccatagcc acacgacgcc tattaattgt gtcggctaac acgtccgcga   12660
tcaaatttgt agttgagctt tttggaatta tttctgattg cgggcgtttt tgggcgggtt   12720
tcaatctaac tgtgcccgat tttaattcag acaacacgtt agaaagcgat ggtgcaggcg   12780
gtggtaacat ttcagacggc aaatctacta atggcggcgg tggtggagct gatgataaat   12840
ctaccatcgg tggaggcgca ggcggggctg gcggcggagg cggaggcgga ggtggtggcg   12900
gtgatgcaga cggcggttta ggctcaaatg tctctttagg caacacagtc ggcacctcaa   12960
ctattgtact ggtttcgggc gccgtttttg gtttgaccgg tctgagacga gtgcgatttt   13020
ttcgtttctct aatagcttcc aacaattgtt gtctgtcgtc taaaggtgca gcgggttgag   13080
ttccgtcgg cattggtgga                                                  13100
```

HIGH THROUGHPUT SYSTEM FOR PRODUCING RECOMBINANT VIRUSES USING SITE-SPECIFIC RECOMBINATION

CROSS-REFERENCE TO OTHER APPLICATIONS

Priority is claimed from Korean Patent Application No. 2002-12634, filed on Mar. 9, 2002.

BACKGROUND OF THE INVENTION

1. Field of the Invention

This invention relates to a method for producing recombinant viruses and vectors for the same. Furthermore, this invention relates to deoxyribonucleic acid (DNA) constructs for the method and the recombinant viruses produced by the method.

2. Description of the Related Art

A recombinant viral vector means a genetically engineered vector, which is used in, for example: the preparation of a vaccine; analysis of function of a gene, a group of genes, or a genomic domain; production of proteins; and gene therapy. Genomic materials, which can be integrated into a viral vector, include any genomic materials such as a gene, cDNA, genomic DNA, DNA sequences encoding peptides or proteins, ribonucleic acid (RNA), anti-sense RNA, siRNA, DNA for si RNA, a promoter, or an enhancer. A virus, which is used in the preparation of a vector, includes baculovirus, adenovirus, adeno-associated virus (AAV), retrovirus, Herpes virus, hepatitis B virus (HBV), polioma virus, sindbid virus, and vaccinia virus.

Retroviruses are known as one of the most widely used viruses in gene therapy. See Patience, C., et al., *Packaging of Endogenous Retroviral Sequences in Retroviral Vectors Produced by Murine and Human Packaging Cells*, J. Virol., April 1998, pp. 2671-2676, Vol. 72, No. 4; Marshall, E., Gene Therapy's Growing Pains, Science, Aug. 25, 1995, pp. 1050-1055, Vol. 269. Retroviral genomes have two long terminal repeats (LTRs), capsid sequences and 3 (three) coding regions (gag, pol and env), and the method of preparation and their use in vitro and in vivo have been disclosed. See WO9908692A1 and EP 453242. The clinical application of a retroviral vector, however, has the following disadvantages: it forms a replication-competent retrovirus (RCR) (see Powell, S. K., et al., *Efficacy of Antiretroviral Agents Against Murine Replication-Competent Retrovirus Infection in Human Cells*, J. Virol., October 1999, pp. 8813-8816, Vol. 73, No. 10); it has a relatively lower level of gene expression, and the level decreases continuously in vivo; and the titer of virus is low. Furthermore, the retrovirus cannot transfer a gene to a non-dividing cell. See Jaffee, E. M., et al., *High Efficiency Gene Transfer into Primary Human Tumor Explants Without Cell Selection*, Cancer Research, 1993, pp. 2221-2226, Vol. 53, Issue 10; Bender, M. A., et al., *Evidence that the Packaging Signal of Moloney Murine Leukemia Virus Extends into the gag Region*, J. Virol., May 1987, pp. 1639-1646, Vol. 61, No. 5.

An adenovirus has a linear genome (sized about 36 kb) and includes replication origin and capsid signals near to the left inverse terminal region (ITR) (103 bp). See Shenk, T., *Adenoviridae: The Viruses and Their Replication*, Fields Virology, 3rd Ed., 1996, pp. 2111-2148. Usually, adenoviral vectors have been made by deleting the E1 site of the viral genome, which is essential for viral replication. The vector includes foreign genomic material substituting the E1 site, which are transferred to packaging cells which provide E1 proteins. As a result, viral replication occurs only in the packaging cells. Representative packaging cells include, for example, HEK 293 cell, 911 cell, and PER.C6 cells. See Hitt, M. M., et al., *Human Adenovirus Vectors for Gene Transfer into Mammalian Cells*, Advances in Pharmacology, 1997, pp. 137-206, Vol. 40; Wang, Y., et al., *Adenovirus Technology for Gene Manipulation and Functional Studies*, Drug Discovery Today, January 2000, pp. 10-16, Vol. 5, No. 1. An adenoviral vector has advantages such as safety, affinity to various cells, possibility of infecting dividing cells and higher titer ($10^{11}$ pfu/ml). Thus, adenoviruses have been used in the preparation of a vector expressing heterologous genes.

Adeno-associated virus (sized about 4700 bp) has ITRs (sized about 145 bp) as replication origins at each terminus. It can be integrated into the genomic DNA of various types of host cells safely and specifically.

In order to use a recombinant virus as a vector, it should be modified not to replicate in the infected cells. Therefore, so-called "defective viruses", which have deletions of some essential regions of genome for viral replication, are usually employed in the preparation of recombinant viral vectors. In a retrovirus, for example, gag, pol and/or env genes are deleted, and the regions are replaced with desired genomic materials. See Bender, M. A., et al., *Evidence that the Packaging Signal of Moloney Murine Leukemia Virus Extends into the gag Region*, J. Virol., May 1987, pp. 1639-1646, Vol. 61, No. 5. For an adenovirus, the E1, E2 and/or E4 sites are deleted for the preparation of a viral vector. See Levrero, M., et al., *Defective and Nondefective Adenovirus Vectors for Expressing Foreign Genes It Vitro and In Vivo*, Gene, 1991, pp. 195-202, Vol. 101; Ghosh-Choudhury, G., et al., *Human Adenovirus Cloning Vectors Based on Infectious Bacterial Plasmids*, Gene, 1986, pp. 161-171, Vol. 50. Additionally, a pseudo-virus vector, which consists of only the essential regions (such as, ITR and capsid sequences) of the replication, has also been used for obtaining recombinant viruses. See WO95/02697.

In addition, baculoviruses, which are known as having circular genomic DNA, have been used for the preparation of viral vectors. Baculoviridae are infectious in invertebrates, such as insects and crustacea. *Autographa californica* nuclear polyhedrosis virus (AcNPV) is one of the most widely used baculoviruses, and it contains double-stranded circular genomic DNA (sized about 134 kb) (GenBank: NC_001623). Smith et al. developed recombinant baculoviruses by inserting β-interferon genes, and successfully obtained interferon proteins from insect cells using the recombinant baculoviruses. See Smith, G. E., et al., *Production of Human Beta Interferon in Insect Cells Infected with a Baculovirus Expression Vector*, Molecular and Cellular Biology, December 1983, pp. 2156-2165, Vol. 3, No. 12. Since then, numerous genes have been expressed and produced using a recombinant baculoviral system. The features of the methods are that: i) it is possible to produce desired recombinant baculoviruses at high efficiency by employing polyhedrin promoter; and ii) it can be used for the expression of genes that do not exhibit their activities when incubated in bacteria. This is due to that post-translational modification is carried out in insect cells. However, the size of the genome of baculovirus made it difficult to engineer the genome through the conventional restriction and ligation method. Therefore, homologous recombination has been used in insect cells generally. In order to conduct homologous recombination, carrier vectors containing desired genes and nucleic acid sequences necessary for the homologous recombination are prepared. Then, insect cells are transfected with the carrier vectors and viral genomic DNA to induce recombination. In that method, however, since the production efficiency of recombinant viruses is relatively low (0.1-2%), repetitive screening of baculoviral plaques should be performed in order to obtain the desired recombinant viruses. Thus, it is also considered as being an inefficient method.

Kitts et al. disclosed an improved method that increased production efficiency of recombinant viruses. See Kitts, P. A., *Linearization of Baculovirus DNA Enhances the Recovery of Recombinant Virus Expression Vectors*, Nucleic Acids Research, 1990, pp. 5667-5672, Vol. 18, No. 19. They made baculoviral genomic DNA to be in linear form using a restriction enzyme. In the Kitts' method, a linker, which includes Bsu36I recognition base sequences, CCTNAGG, or lacZ genes, is inserted into wild-type AcNPV genome at the polyherin locus in order to introduce Bsu36I site recognition nucleic acid sequences. Next, the viral DNA is digested with Bsu36I restriction enzyme, and then transferred to insect cells together with carrier vectors containing desired genomic materials so as to induce homologous recombination. The production efficiency of the desired recombinant viruses is from 26% to 44%. According to that method, linear digested DNA segments, which are not subjected to recombination, are excluded selectively from the production of viral vectors. Thus, the desired recombinant viruses expressing desired protein can be generated with relatively high efficiency. However, the method has disadvantages as follows: i) it is not possible to digest Bsu36I recognition sites up to 100% and ii) since the digested DNA segments are fused with each other in insect cells by ligase, selection procedures for the desired viral vectors need to be employed.

Peakman et al. provided another method using site-specific recombination of cre/loxP system in vitro. See Peakman, T. C., et al., *Highly Efficient Generation of recombinant Baculoviruses by Enzymatically Mediated Site-Specific In vitro Recombination*, Nucleic Acids Research, pp. 495-500, Vol. 20, No. 3. Briefly, they prepared baculoviruses containing loxP sites and applied them to site-specific recombination in vitro with desired genomic materials by reacting the viruses with transfer vectors having the genomic materials flanked with loxP sites, in the presence of cre recombination enzyme. In that method, the time-period for producing recombinant viruses is shortened. However, the production efficiency of desired recombinant viruses is still low (0.2% to 49%), thereby it is not suitable to be used as a high-throughput system for the preparation of recombinant viruses.

In addition, Luckow et al. reported a method of inserting a desired genomic cassette into a baculoviral genome by site-specific recombination in a cell. See Luckow, V. A., et al., *Efficient Generation of Infectious Recombinant Baculoviruses by Site-Specific Transposon-Mediated Insertion of Foreign Genes into a Baculovirus Genome Propagated in Escherichia coli*, J. Virol., August 1993, pp. 4566-4579, Vol. 67, No. 8. According to Luckow's method, a shuttle vector (sized about 130 kb) is prepared by inserting a plasmid replication origin, which replicates in bacteria, including kanamycin resistance gene and attTn7 recombination sequences, into baculoviral genome. The shuttle is named "Bacmid." DH10Bac was generated by transforming *E. coli* with Bacmid and a helper plasmid, which in turn was transformed using a plasmid containing desired genes and polyhedrin promoter to prepare recombinant Bacmid in *E coli*. The resulting recombinant Bacmid is isolated and transferred to insect cells to obtain recombinant viruses. According to that method, baculoviruses can be obtained with relatively high efficiency by using site-specific recombination of transposon. That method, however, required complex procedures, for example, cloning desired genomic materials to Tn7 Bacmid carrier vectors; transforming DH10Bac for the recombination of Tn7 baculoviruses; selecting and isolating bacteria having Bacmid that contains the desired genomic material; purifying Bacmid DNA (sized about 130 kb) from the isolated bacteria; and transferring the DNA again to insect cells to produce recombinant virues.

Thus, non of the above-mentioned methods of the prior art have provided suitable ways to overcome the problems of a relatively long time-period in preparing recombinant viruses (about 3 to 6 weeks) and low production efficiency. Therefore, there has been a demand for the development of an improved method.

In this regard, we have carried out studies to produce recombinant viruses having a desired genomic material more rapidly and efficiently. In one embodiment, we prepared recombinant viral vectors in vitro using site-specific recombination and employing the vectors to produce recombinant viruses. Since the viral vectors obtained in vitro according to this invention can be applied to animal cells directly without further procedures like selection, the present invention not only simplifies the total procedure significantly but also provides desired recombinant viruses with up to 100% production efficiency. Thus, higher virus titer can be obtained according to the present invention.

SUMMARY OF THE INVENTION

Any publications referenced herein are hereby incorporated by reference in this application in order to more fully describe the state of the art to which the present invention pertains.

To understand the present invention, it is important to note that all technical and scientific terms used herein, unless otherwise defined, are intended to have the same meaning as commonly understood by one of ordinary skill in the art. The techniques used herein are also those that are known to one of ordinary skill in the art, unless stated otherwise.

Reference to particular buffers, media, reagents, cells, culture conditions and the like, or to some subclass of same, is not intended to be limiting, but should be read to include all such related materials that one of ordinary skill in the art would recognize as being of interest or value in the particular context in which that discussion is presented. For example, it is often possible to substitute one buffer system or culture medium for another, such that a different but known way is used to achieve the same goals as those to which the use of suggested method, material or composition is directed.

It is an object of this invention to provide more rapid and efficient method for producing recombinant viruses.

In order to accomplish this object, this invention employs recombinant viral vectors that are prepared in vitro by site-specific recombination.

In the present invention, viral genomic DNA is made in linear form by restriction enzymes before being applied to site-specific recombination in vitro. Since linear viral genomic DNA, which is not subjected to the site-specific recombination, cannot replicate by itself, almost all of the expressed viruses are believed to be those from the circular viral genomic DNA. Thus, according to the present invention, it is possible to obtain recombinant viruses at high efficiencies without the procedures for selecting and isolating the desired recombinant viruses. Accordingly, the method of the present invention can be applied to a virus having circular genomic DNA, for example, polioma virus, papiloma virus and hepatitis B virus.

Site-specific recombination is an event occurring naturally in various living organisms. Enzymes for the site-specific recombination contain not only endonuclease activity, but also ligase activity, so they recognize a certain part of DNA sequences and replace it with any other corresponding DNA sequence. See Yang, W., et al., *Site-Specific Recombination in Plane View*, Structure, Nov. 15, 1997, pp. 1401-1406, Vol. 5. Int/att system from bacterio λ phage, Cre/LoxP system from P1 bacteriophage and FLP-FRT system from yeast are well developed site-specific recombination systems.

Site-specific recombination systems have been used in i) expression control of desired genomic materials cloned into recombinant viruses, ii) excising helper-virus when preparing helper-viral dependent viruses, iii) increasing the efficiency of homologous recombination in packaging cells, or iv) inducing site-specific recombination between carrier vectors and viral genome in packaging cells to prepare recombinant viruses. See Ng, P., et al., *Yeast Recombinase FLP Functions Effectively in Human Cells for Construction of Adenovirus Vectors*, BioTechniques, September 2000, pp. 524-528, Vol. 29, No. 3; Ng, P., et al., *A High-Efficiency Cre/loxP-Based System for Construction of Adenoviral Vectors*, Human Gene Therapy, Nov. 1, 1999, pp. 2667-2672, Vol. 10; Hardy, S., et al., Construction of Adenovirus Vectors Through Cre-lox Recombination, J. Virol., March 1997, pp. 1842-1849, Vol. 71, No. 3; Parks, R. J., et al., *A Helper-Dependent Adenovirus Vector System: Removal of Help Virus by Cre-mediated Excision of the Viral Packaging Signal*, Proc. Natl. Acad. Sci. USA, November 1996, pp. 13565-13570, Vol. 93. However, the said applications of the site-specific recombination disclosed in the prior art were merely indirect and supplementary uses in vivo or in a cell line, not in vitro.

In addition, applications of site-specific recombination in the preparation of recombinant viruses having circular genomic DNA were reported: i) in the preparation of recombinant baculoviruses in bacteria using Tn7 recombination, and ii) in the preparation of recombinant baculoviruses using a cre/lox-P system in vitro.

However, there have been no applications of site-specific recombination in vitro for specific insertion of desired genomic materials into viral genomic DNA in order to obtain recombinant viral vectors. In particular, there have been no applications to prevent the expression of viral genomic DNA that do not contain desired genomic materials. Thus, the present invention is characterized by employing site-specific recombination in preparing recombinant viral vectors in vitro. The present invention has unexpected advantages compared to the prior art as follows: i) it is possible to obtain recombinant viral vectors more easily and more rapidly by employing site-specific recombination in vitro; ii) it does not require any further procedure of selecting desired recombinant viruses from intermediate host cells, since the viral genomic DNA is made in linear form and thereby the linear viral DNA, which do not form in circular form by integration of the desired genomic materials, cannot be expressed; and iii) it is possible to generate the same kind of genomic materials from various types of viruses or to generate various genomic materials from the same kind of viral type multi-well (e.g., 96-well or 384-well) by employing a common transfer vector containing an expression cassette that does not have DNA from a viral genome.

Furthermore, according to the present invention, homologous recombination in the packaging cells is not required. Also a particular cell line for inducing homologous recombination is not required. Table 1 and Table 2 show the results of the comparisons between the method of the present invention (BacHTS system) and the methods of the prior art (BacPAK6 system and BacToBac system) with regard to the processes. With the results, it is clear that the desired recombinant viruses can be obtained even more rapidly by using the method of this invention in comparison to the prior art.

TABLE 1

The comparison of the number of procedures between the method of the present invention and the methods of prior art.

| | the number of procedures | Days | time-period |
|---|---|---|---|
| BacPAK6 system | 11 | 6 | 10 |
| BacToBac system | 13 | 8 | 12 |
| BacHTS system | 5 | 3 | 7 |

TABLE 2

The comparison of the processes required for preparation of baculoviruses.

| BacPAK6 system | BacToBac system | BacHTS system |
|---|---|---|
| 1. RE cut | 1. LR reaction | 1. Recombination |
| 2. Agarose gel elution | 2. Transformation | 2. Transfection |
| 3. Ligation | 3. Colony seeding | 3. Infection |
| 4. Transformation | 4. Plasmid purification | 4. Harvest and virus storage |
| 5. Colony seeding | 5. RE analysis | 5. Protein expression analysis |
| 6. Plasmid purification | 6. DH10Bac transformation | |
| 7. RE analysis | 7. Streaking | |
| 8. Transfection | 8. Seeding | |
| 9. Infection | 9. Bacmid purification | |
| 10. Harvest and virus storage | 10. Transfection | |
| 11. Protein expression analysis | 11. Infection | |
| | 12. Harvest and virus storage | |
| | 13. Protein expression analysis | |

Furthermore, according to the present invention, since the promoter for the expression of the desired genomic materials, and the fusion system and the polyadenyl sequences for the preparation of a fusion protein are provided from the parent viral genome, the gene cassette cloned to a common carrier vector can be applied to produce various types of viruses.

Thus, the present invention provides significantly useful tools for studying functions of genes, of which demand has been increasing greatly since the completion of the genome project. See Wang, Y., et al., *Adenovirus Technology for Gene Manipulation and Functional Studies*, Drug Discovery Today, January 2000, pp. 10-16, Vol. 5, No. 1.

In one embodiment, the present invention employs baculovirus having circular genomic DNA, and an Int/att system from bacteriophage λ (Genebank: NC 001416) as a site-specific recombination system. In the Int/att system, attR site-specific recombination sites within a viral genomic DNA fragment react with corresponding attL site-specific recombination sites, including desired genomic materials from a carrier vector, in the presence of λ integrase recombination enzyme, integration host factor (IHF) as a co-factor and Xis, and result in a vector DNA fragment containing attB and attP sites. See Hartley, J. L., et al., *DNA Cloning Using In Vitro Site-Specific Recombination*, Genome Research, 2000, pp. 1788-1795, Vol. 10. Other recombination systems from various organisms, for example, the cre/loxP system from bacteriophage P1, and the FLP/FRT system from the *Saccharomyces cerevisiae* 21t circle plasmid, can be employed.

When the mixture is transferred directly to suitable host cells, which are expected to express desired recombinant viruses, only the circular viral genomic DNA containing attB1-[desired genomic materials]-attB2 can replicate and form viral particles. The linear viral DNA fragment and the vector DNA itself, which do not react with each other, and the circular viral DNA having attP sites cannot replicate and cannot form viral particles. In FIG. 1, site-specific recombination between a gene cassette and vBacHTS baculoviral DNA in vitro is presented.

In another embodiment, vBacHTS viral DNA is constructed to include site-specific recombination sequences and Bsu36I recognition base sequences, which in turn are made to linear form viral DNA flanked by 2 (two) site-specific sites with treatment of Bsu36I restriction enzyme. The linear vBacHTS DNA cannot form viral particles since the vBacHTS viral DNA is digested at 2 (two) Bsu36I recognition sites having nucleic acid sequences different from each other, while the circular form DNA generated by site-specific recombination formed viral particles efficiently.

In another embodiment, the reaction mixture containing viral DNA having desired genomic materials, which is integrated by site-specific recombination, is transferred to Sf21 insect cells, and then viral packaging is detected. Thus, according to the present invention, recombinant viruses can be obtained without employing intermediate host cells, such as *E. coli* or yeast, for selecting and amplifying suitable genomic DNA. Therefore, the recombinant viruses are suitable for the purpose of expressing desired genes from host cells. The activity measurement of GFP and GUS proteins indicates that the method of the present invention is more efficient than the method of the prior art.

BRIEF DESCRIPTION OF THE DRAWINGS

FIG. 23 shows enzyme activity using X-Gluc of GUS recombinant viruses in a multi-well plate.

FIG. 24 shows the results of site-specific recombination in vitro.

FIG. 25 depicts expression of GFP-LacZ fusion proten in Sf21 cells after 4 days from the transfer of recombinant DNA to the cells.

DESCRIPTION OF THE PREFERRED EMBODIMENTS

Preferred embodiments of this invention are described in the following examples. Other embodiments within the scope of the claims herein will be apparent to those skilled in the art from consideration of the specification or practice of the invention as disclosed herein. It is intended that the specification, together with the examples, be considered exemplary only, with the scope and the spirit of the invention being indicated by the claims which follow the examples. The examples herein are meant to exemplify the various aspects of carrying out the invention and not intended to limit the scope of the invention in any way. The examples do not include detailed descriptions of conventional methods employed, such as in the performance of genomic DNA isolation, polymerase chain reaction (PCR), and sequencing procedures. Such methods are well-known to those skilled in the art and are described in numerous publications. In addition, all the publications referred herein are integrated hereto as references.

EXAMPLES

Example 1

Figure 1:
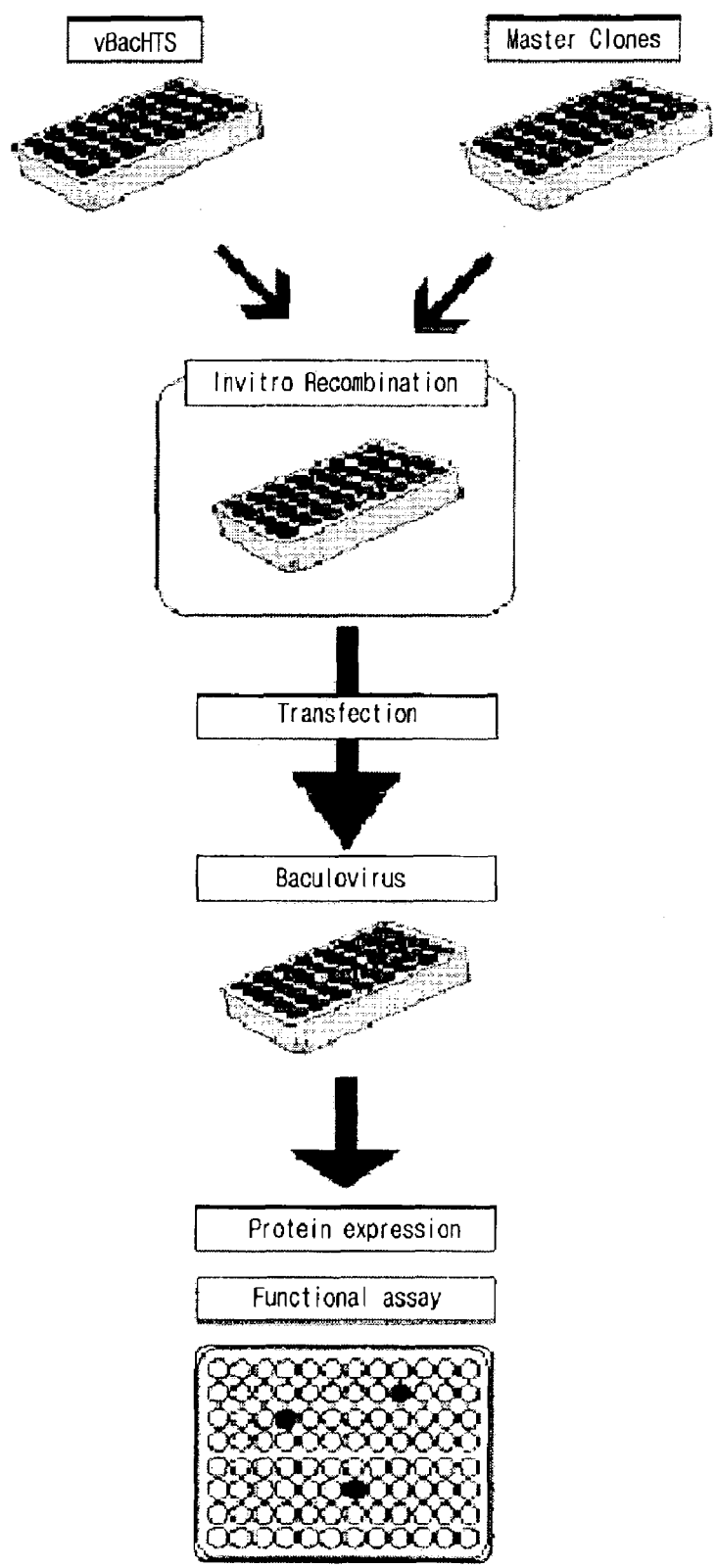
FIG. 1 illustrates gene-screening processes using BacHTS system.
Figure 2:
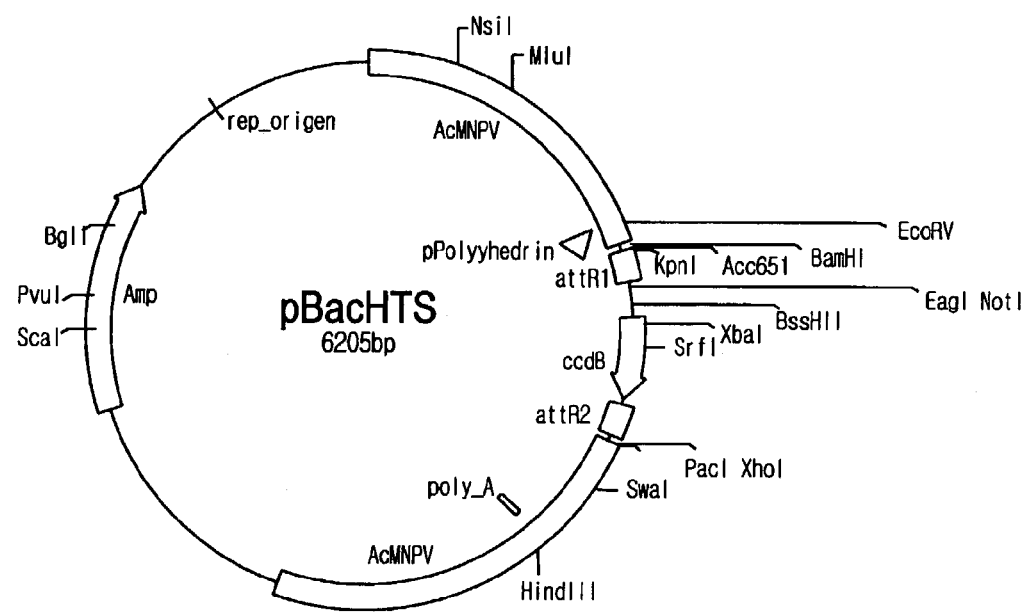
FIG. 2 depicts the cleavage map of pBacHTS.
Figure 3:
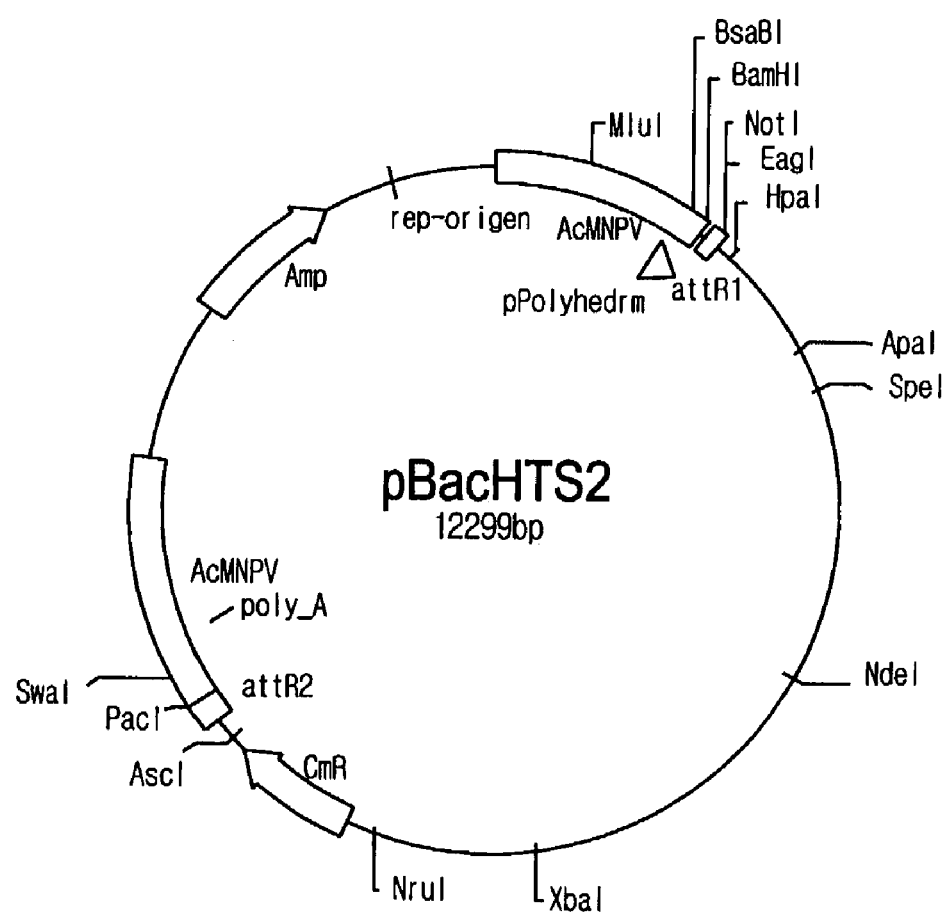
FIG. 3 depicts the cleavage map of pBacHTS2.
Figure 4:
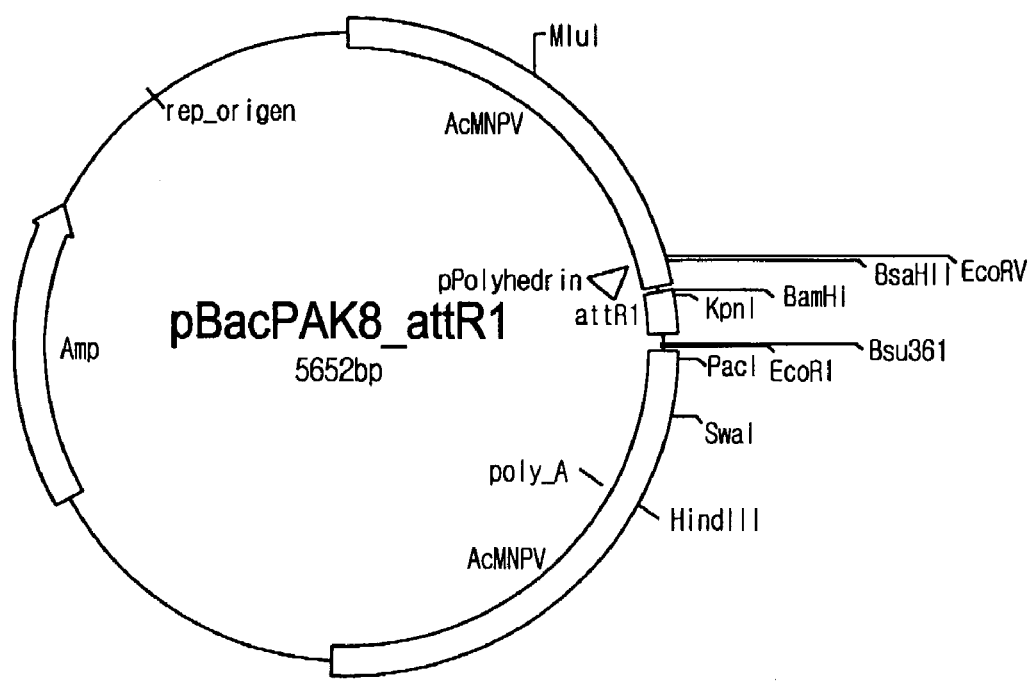
FIG. 4 depicts the cleavage map of pBacPAK8_attR1.
Figure 5:
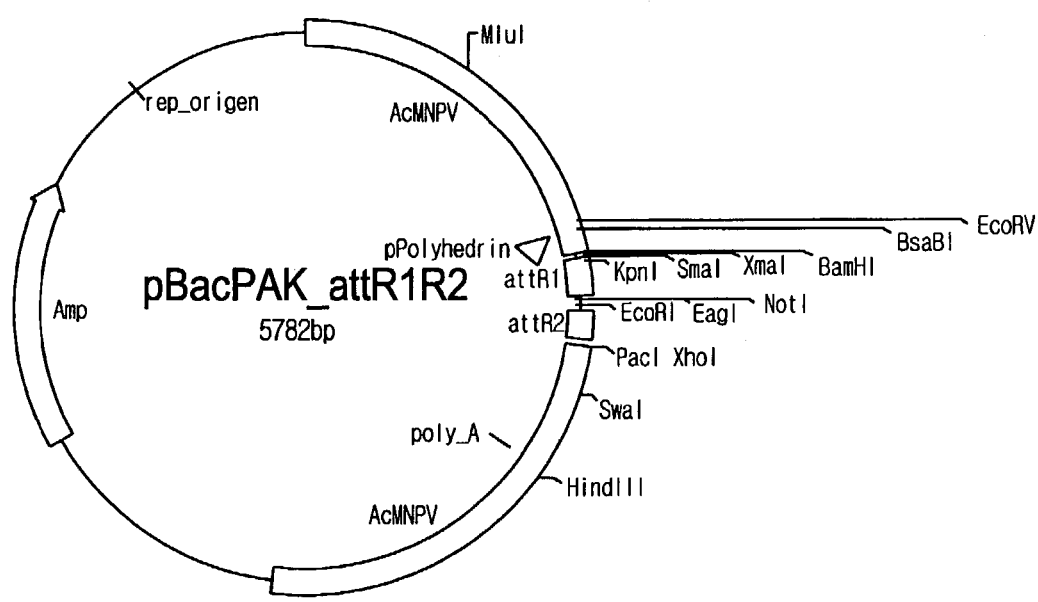
FIG. 5 depicts the cleavage map of pBacPAK_attR1R2.
Figure 6:
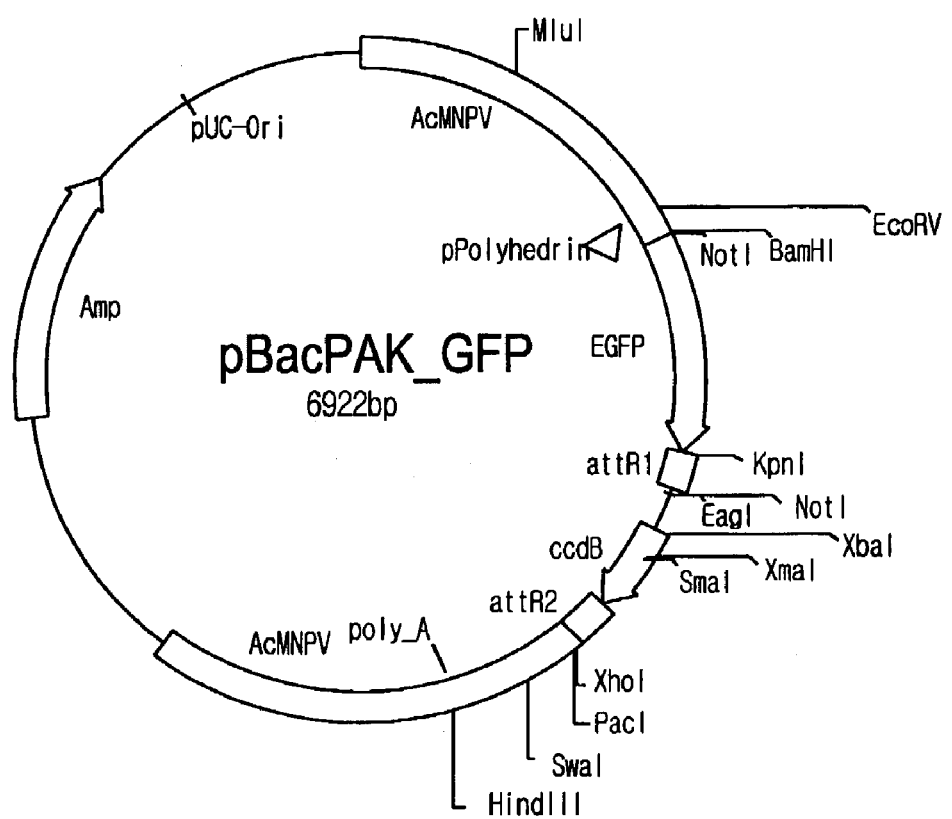
FIG. 6 depicts the cleavage map of pBacHTS_GFP.

Preparation of pBacHTS pBacHTS viral vectors were prepared. For the preparation, firstly, pBacPAK8_R1 (see FIG. 4) was provided by cloning amplified attR1 sites and Bsu36I recognition base sequences at BamHI/EcoRI sites of a shuttle vector of pBacPAK8 (Genebank: U2446, Clontech, California, U.S.A.) and transforming DH5α (Life Technologies Inc., Maryland, U.S.A.) with the cloned vector, and then by incubating and screening in agar medium including ampicillin. Likewise, pBacPAK8_R1R2 was prepared by cloning PCR amplified attR2 sites and Bsu36I recognition site sequences at EcoRI/PacI site sequences of pBacPAK8_R1 (see FIG. 5). In order to obtain pBacHTS, a DNA fragment (427 bp) including ccdB gene from EcoRI digested fragments of pEntr4 plasmid (Invitrogen, California, U.S.A.) was inserted to the pBacPAK8_R1R2, and then the resulting plasmid was transferred to DB3.1 cell (Life Technologies Inc., Maryland, U.S.A.). pBacHTS contained two different Bsu36I recognition sequences between the attR1 site and the attR2 site (FIG. 2). The attR1 sites and the attR2 sites included site-specific recombinase target sequences that reacted with attL1 and attL2 sites, respectively, in the presence of integrase from λ bacteriophage, Xis, IHF-α and IHF-β.

Example 2

Figure 7:
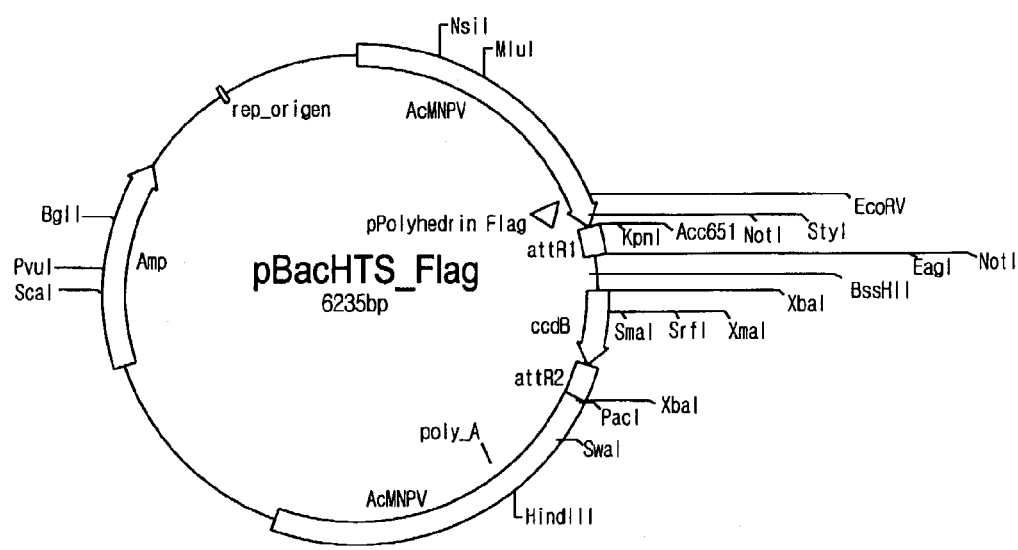
FIG. 7 depicts the cleavage map of pBacHTS Flag.

Preparation of pBacHTS 6His, pBacHTS GST, pBacHTS HisGst, pBacHTS GFP and pBacHTS Flag A fusion tag was inserted into the site in back of the polyhedrin promoter in order to prepare recombinant baculovirus expressing fusion proteins. pBacHTS_Gst was designed for the preparation of an expression vector for glutathione-s-transferase (GST) fusion protein. In order to accomplish this, pGEX-2T (Genbank: U13850) was PCR-amplified using a primer including BglII and a primer including BamHI linker, which in turn was treated with BglII and BamHI and then was inserted into pBacHTS/BamHI restriction sites. In addition, pBacHTS_His was designed for the preparation of a vector expressing His tag fusion protein by inserting 6 His linker to the BamHI site of pBacHTS. Furthermore, pBacHTS_HisGST was designed by inserting BglII-and-BamH1H-treated GST genes, which were PCR-amplified, to the BamHI site of pBacHTS_His. On the other hand, the green fluorescent protein (GFP) gene was PCR-amplified using a primer containing a BamHI linker and a primer containing a KpnI linker, which in turn was digested with BamHI/KpnI. After that, the digested gene was integrated into BamHI/KpnI restriction sites of pBacHTS to generate pBacHTS_GFP. Furthermore, pBacHTS Flag was prepared by inserting a linker expressing Flag tag at BamHI/KpnI sites of pBacHTS (see FIG. 7).

Example 3

Figure 8:
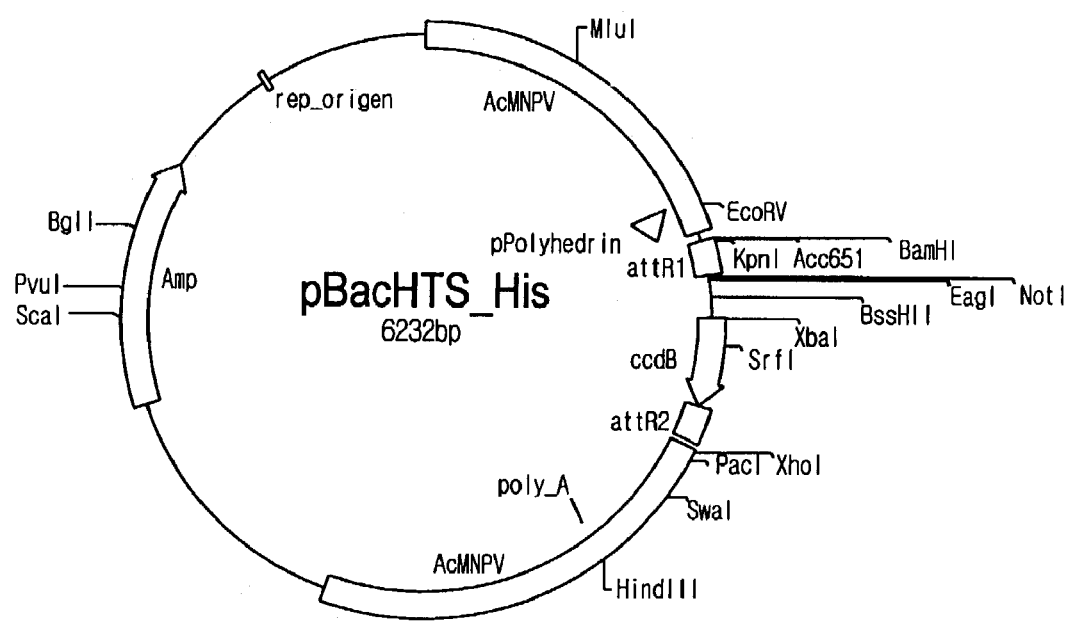
FIG. 8 depicts the cleavage map of pBacHTS_His.
Figure 9:
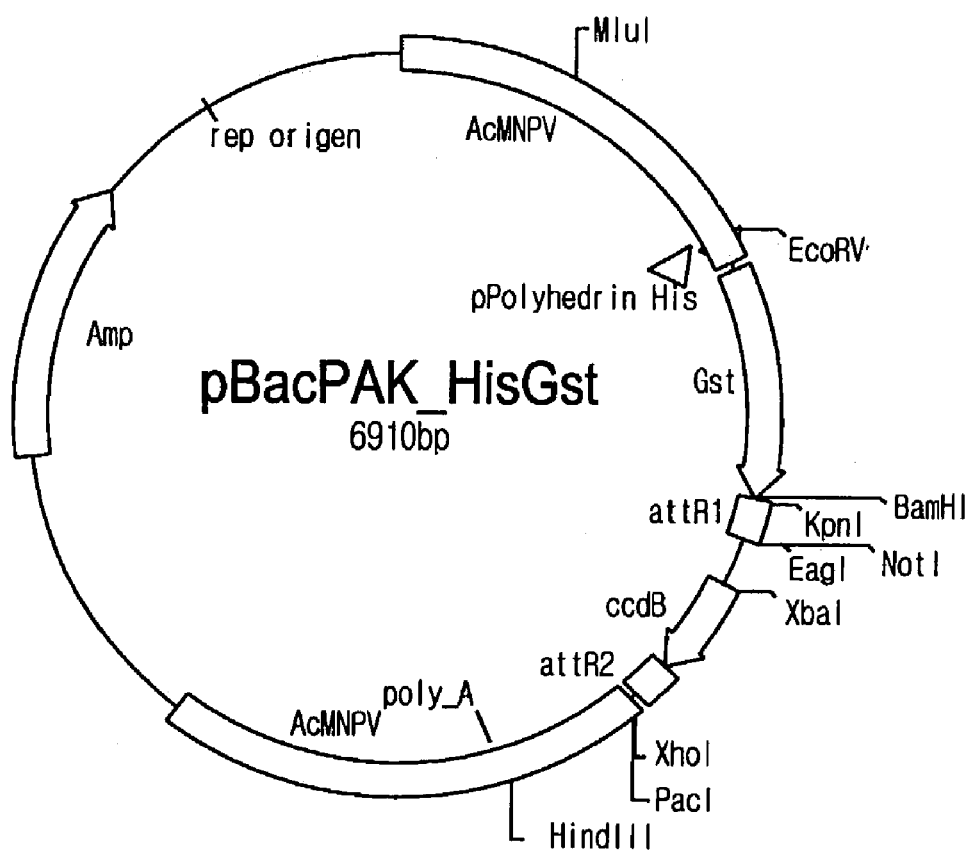
FIG. 9 depicts the cleavage map of pBacHTS_HisGst.
Figure 10:
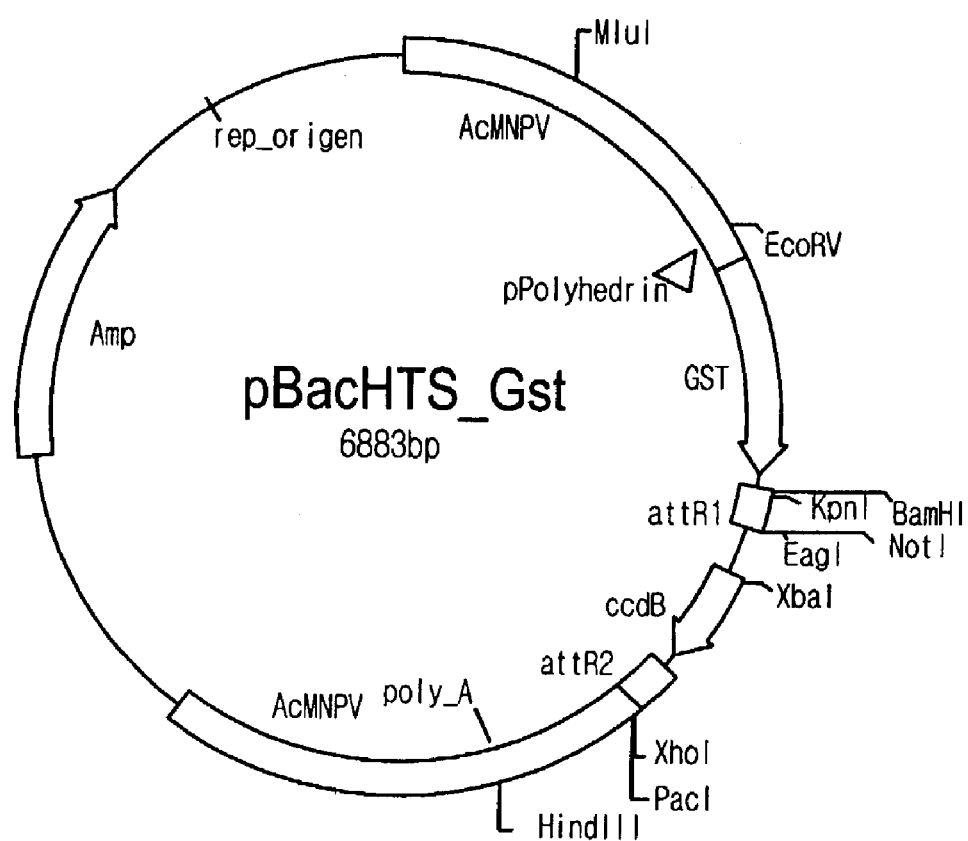
FIG. 10 depicts the cleavage map of pBacHTS_Gst.
Figure 11:
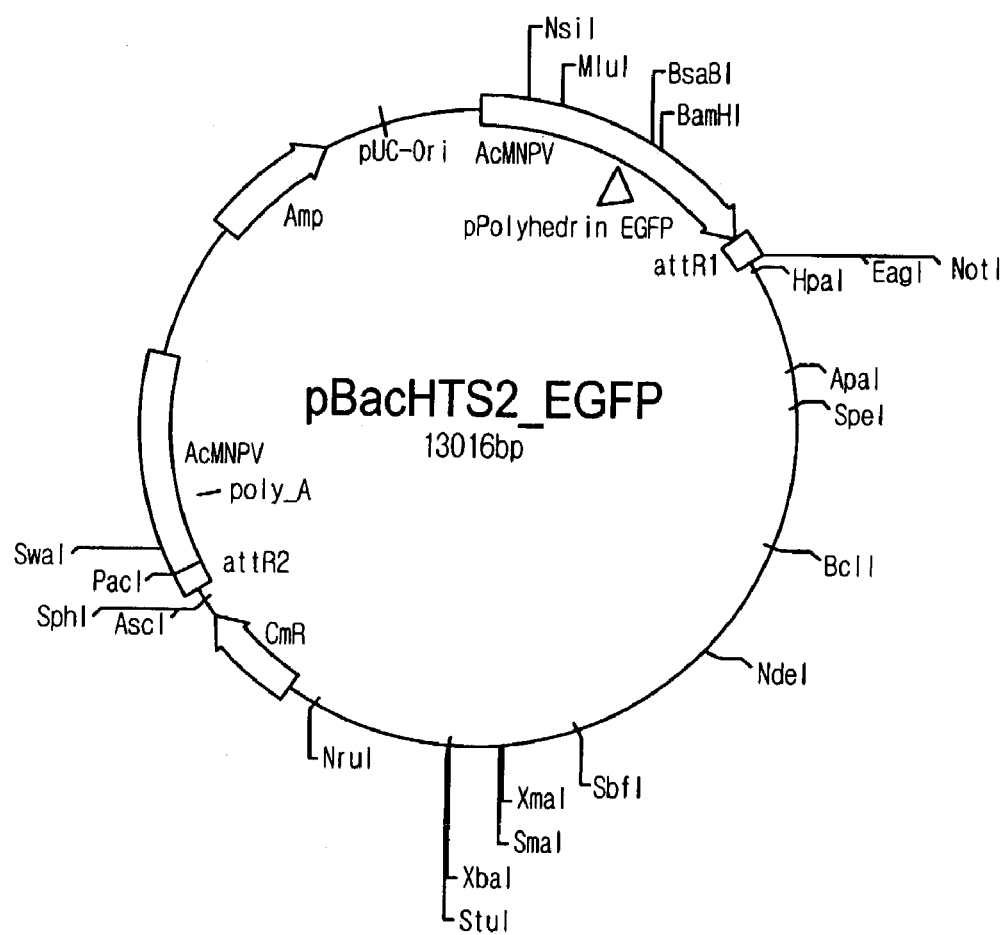
FIG. 11 depicts the cleavage map of pBacHTS2_EGFP.
Figure 12:
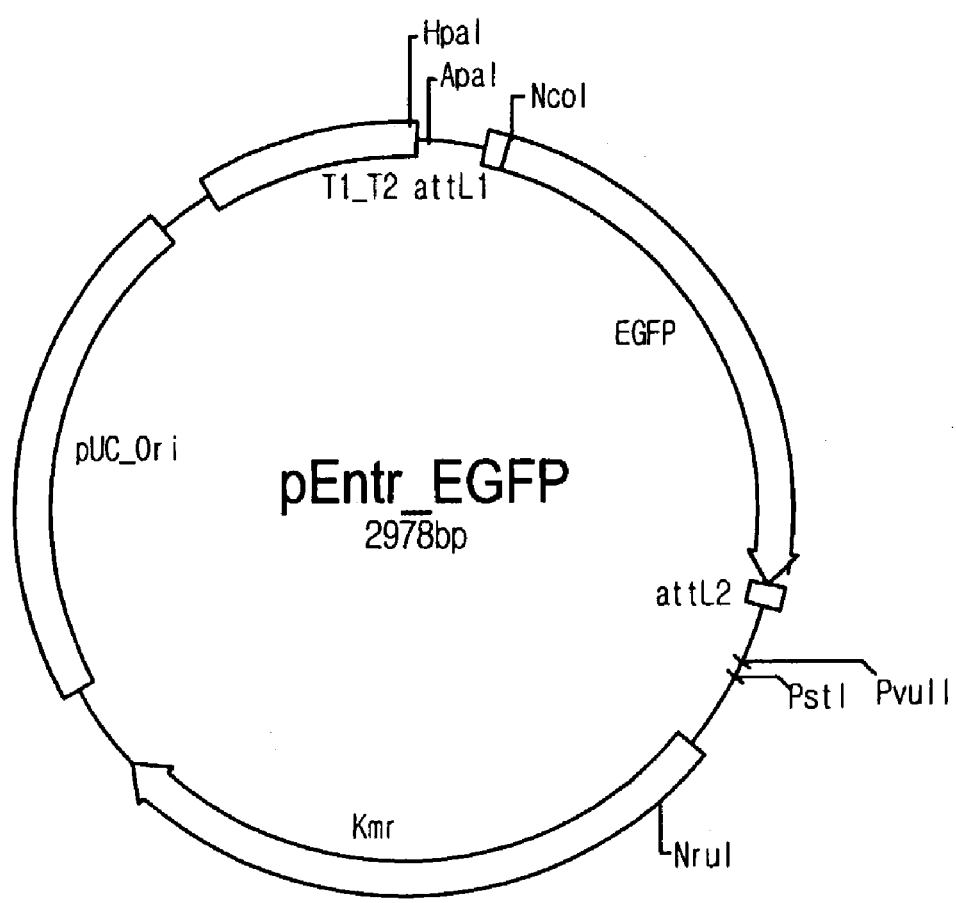
FIG. 12 depicts the cleavage map of pEntr_EGFP.
Figure 13:
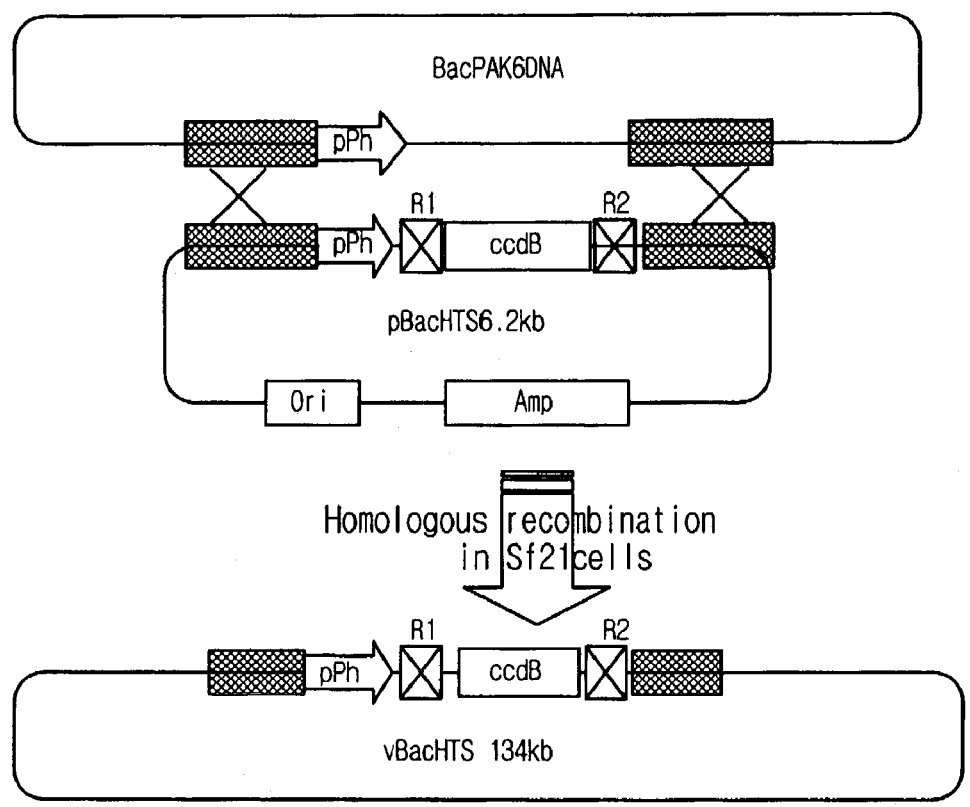
FIG. 13 illustrates the process of preparation of vBacHTS virus.
Figure 14:
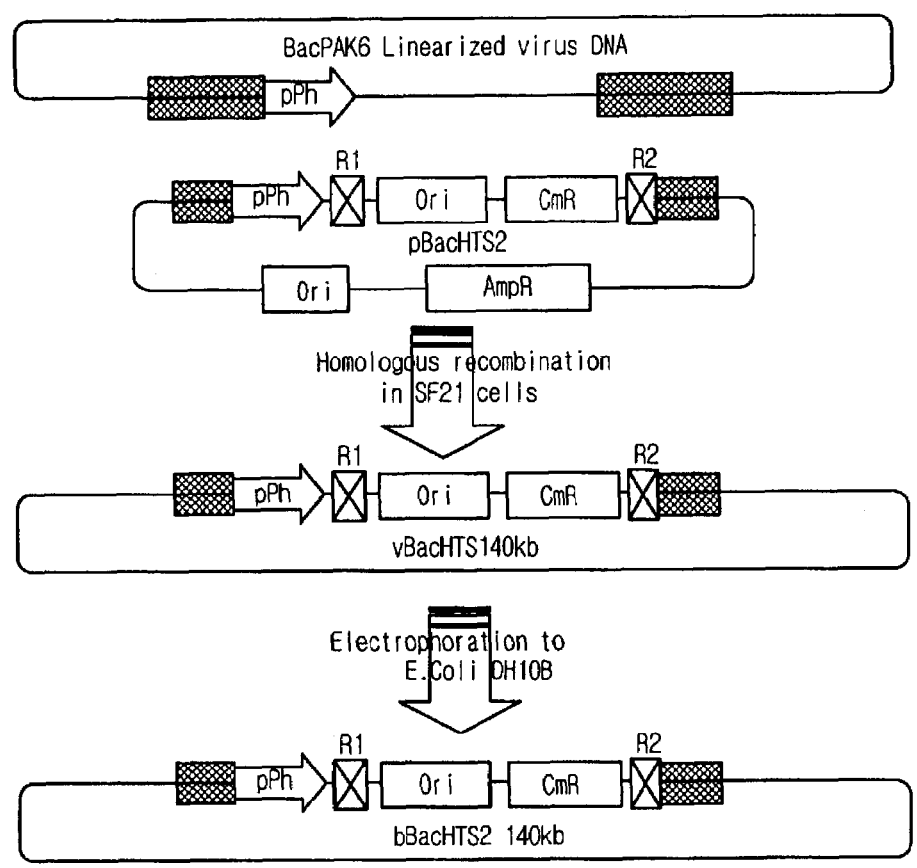
FIG. 14 illustrates the process of preparation of bBacHTS2 clone.
Figure 15:
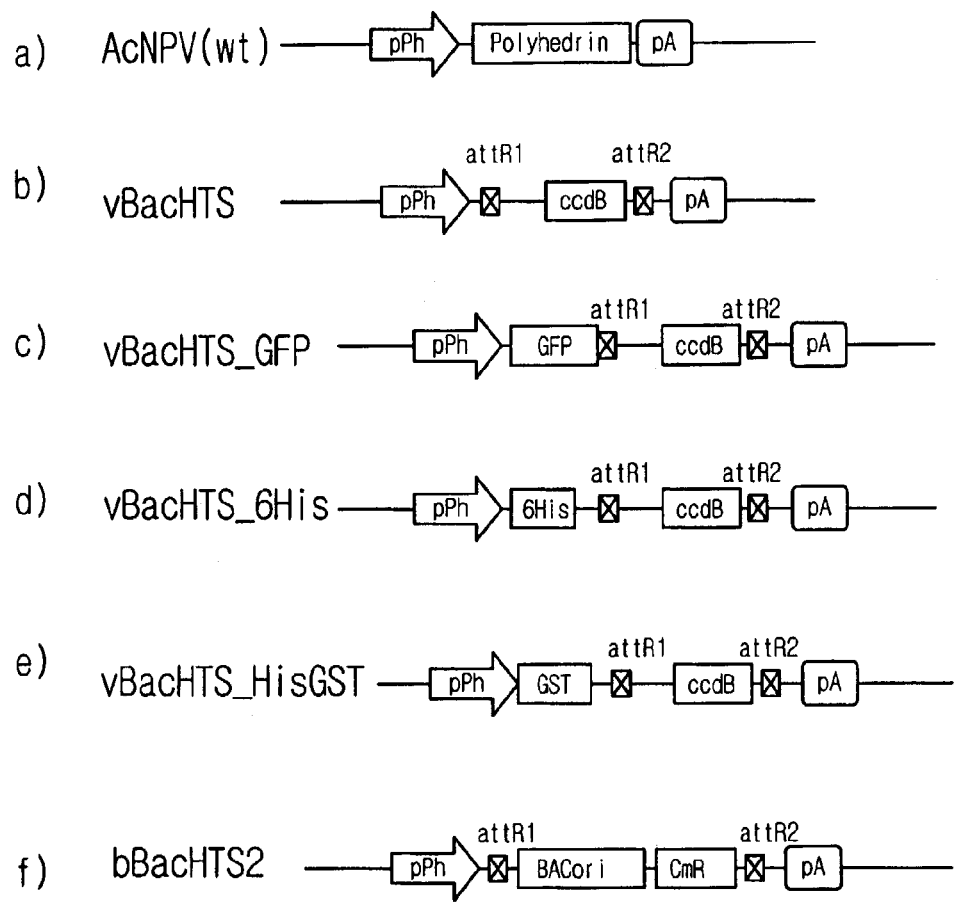
FIG. 15 shows the map of baculoviral polyhedrin locus.

Preparation of DNA of vBacHTS, vBacHTS His, vBacHTS HisGST and vBacHTS GFP Viruses Baculoviruses of which polyhedrin loci were replaced by pBacHTS plasmids were prepared using homologous recombination. Briefly, Sf21 insect cells were transfected with a mixture of pBacHTS plasmid, Bsu36I digested BacPAK6 viral DNA (Clontech, California, U.S.A. #6144-1) and Lipofectin (Life Technologies Inc., Maryland, U.S.A.) to induce homologous recombination in the cells. The recombinant viruses were isolated through twice-repeated plaque assays, which in turn were subjected to PCR. The purified viral clone was named vBacHTS virus (SEQ. ID No. 1: the sequence of its polyhedrin locus) (see FIG. 15). As disclosed in FIG. 13, pBacHTS His (see FIG. 8), pBacHTS_HisGst (see FIG. 9), pBacHTS_GST and pBacHTS_GFP were respectively transferred together with the BacPAK6 virus to generate vBacHTS_His (SEQ. ID No. 2: the sequence of its polyhedrin locus), vBacHTS_HisGst (SEQ. ID No. 3: the sequences of its polyhedrin locus), vBacHTS_GST (SEQ. ID No. 4: the sequence of its polyhedrin locus) and vBacHTS_GFP (SEQ. ID No. 5: the sequence of its polyhedrin locus) (see FIG. 15). Viral plaques were selected from agarose medium.

Example 4

Purification of Viral DNA of vBacHTS, vBacHTS His, vBacHTS HisGst, vBacHTS GFP, and vBacHTS Viral culture medium having $1.2 \times 10^8$ pfu/ml of viral titer was produced after 3 days from infecting Sf21 cells on a cell culture dish (100 mm diameter) in order to isolate vBacHTS viral DNA. Then, $1.25 \times 10^7$ of Sf21 cells were plated again on a cell culture dish (150 mm diameter), which in turn were infected with a 20 times larger number of viruses multiplicity of infection (MOI), i.e., MOI=20. After incubating for 48 hours, about 25 ml of cell culture medium per dish was obtained. A total of 150 ml of cell culture medium from 6 dishes (150 mm diameter) was centrifugated at 20,000 rpm for 90 minutes, and the resulting precipitated viral particles were recovered (with Hanil, Supra22k). The recovered viral particles were suspended in 2 ml of TE (10 mM Tris-HCl pH=8.0, 1 mM EDTA), and then were treated with a sucrose concentration gradient ultra-centrifuge (Beckman SW41 rotor) at 30,000 rpm. Viral particles were purified from the layer between 50% and 40% sucrose solution. The purified viruses were subjected to centrifugation again at 18,000 rpm for 90 minutes. After that, the precipitates of viral particles were suspended again with 2 ml of TE (10 mM Tris-HCl pH=8.0, 1 mM EDTA), and were left at 42° C. for 2 hours after adding 0.5% SDS, 1% beta-mercaptoethanol and 0.2 mg of Proteinase K thereto, so as to isolate viral envelopes. The viral lysate was extracted twice with the same amount of phenol/chloroform solution, and ethanol was added to the extract, resulting in pure viral DNA obtained as precipitates. Then, 50 units of the restriction enzyme Bsu36I (from New England Biolabs, Inc., Massachusetts, U.S.A., NEB #524) were added to the purified DNA (10 μg). The mixture was left at 37° C. for 2 hours before used in the following studies (see FIG. 16).

Example 5

Preparation of Gene Cassette

A pEntr_GFP gene cassette was prepared by inserting PCR products of GFP between the attL1 site and the attL2 site. A pEntr_GUS gene cassette from LTI was employed.

Example 6

Preparation of the Desired Recombinant Viruses Having GFP Gene or GUS Gene

Recombinant viruses expressing GFP and GUS were generated in this study. The pEntr_GFP gene cassette (100 ng) or the pEntr_GUS gene cassette (100 ng) was transferred to a test-tube, and reacted with 100 ng of Bsu36I treated vBacHTS viral DNA at 25° C. for 2 hours, in the presence of integrase mixture comprising 4 μl of integrase, Xis, IHF-α and IHF-β. Then, Sf21 cells were infected with the reaction mixture together with lipofectin (Life Technologies, Inc., Maryland, U.S.A.), thereby recombinant viruses were generated. After 2 days, green fluorescence was observed from the insect cells including the GFP gene cassette. Furthermore, after 4 days, almost every cell showed green fluorescence. Furthermore, fluorescence and symptoms of viral infection were observed in the infected cells.

Figure 18:
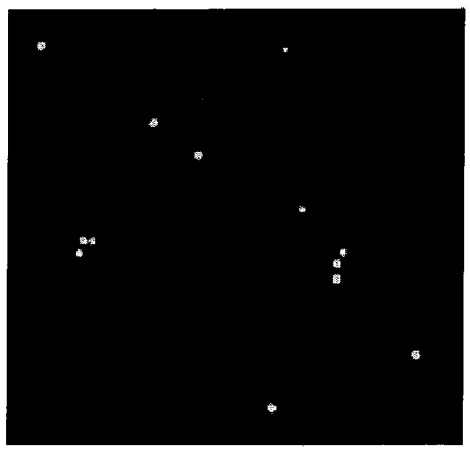
FIG. 18 shows the results of activity assays of GFP baculoviruses and GUS recombinant viruses in a vBacHTS system.
Figure 18:
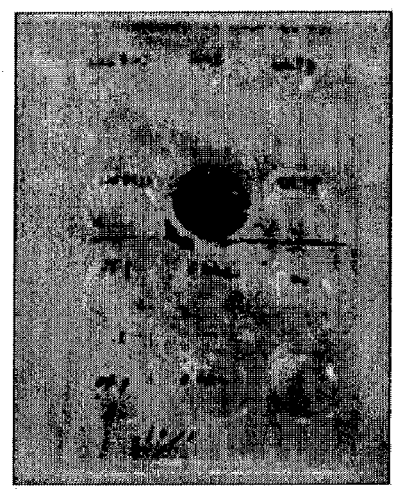
Figure 19:
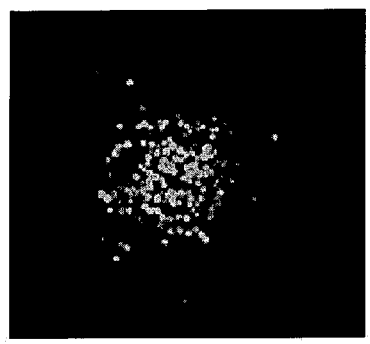
FIG. 19 shows plaque assays for GFP baculoviruses and GUS recombinant viruses in a vBacHTS system.
Figure 19:
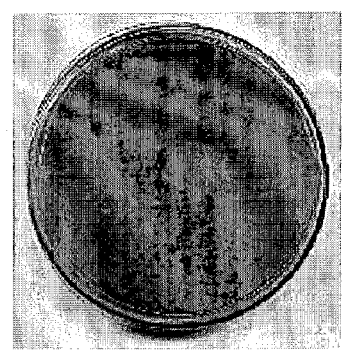
Figure 20:
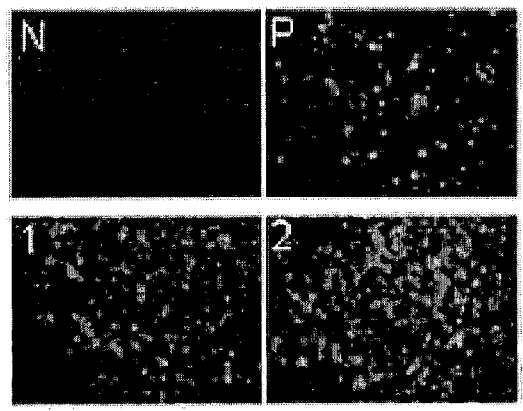
FIG. 20 shows the results of activity assays of GFP baculoviruses in a bBacHTS2 system.
Figure 21:
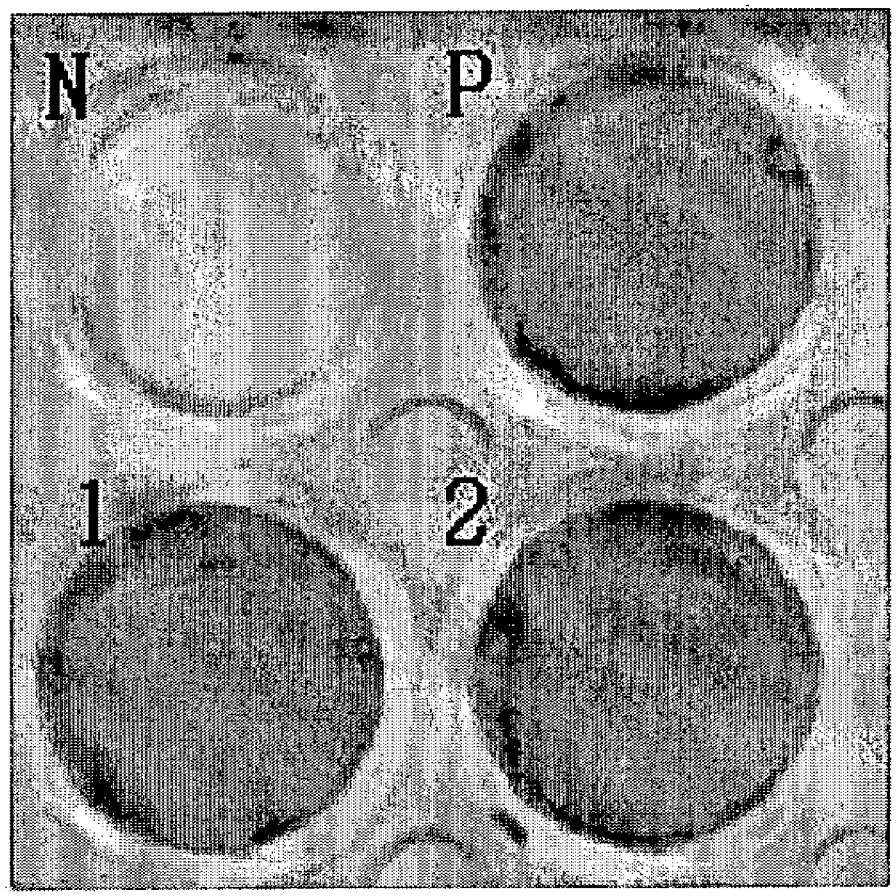
FIG. 21 shows the results of activity assays of GUS recombinant baculoviruses in a bBacHTS2 system.

On the other hand, a mixture containing the pEntr_GUS gene cassette was transferred to Sf21 cells. After 4 days, X-Gluc was added to the cells. After 2 hours of the reaction, the Sf21 cells became blue, which supported the expression of GUS (see FIG. 18). In order to determine the productivity of the recombinant viruses, a 4-day viral culture was dilated and transferred to insect cells. Next, plaques were detected 4 days after adding culture medium containing 1% low-melting point agarose to the infected cells. As the result, most plaques represented blue fluorescence (see FIG. 19).

Example 7

Determination of the Production Efficiency of Recombinant Viruses

Recombinant viruses expressing GFP were prepared in this study. In order to accomplish this, 100 ng of the pEntr_GFP gene cassette containing GFP genes and 200 ng of viral DNA of Bsu36I treated vBacHTS, vBacHTS_His or vBacHTS_HisGST were reacted in the presence of 4 μl of integrase mixture comprising integrase, Xis (excisionase), IHF-α and IHF-β at 25° C. for 6 hours. The resulting mixture was transferred to Sf21 cells together with lipofectin (Life Technologies, Inc., Maryland, U.S.A.) in order to generate recombinant baculoviruses. After incubating at 27° C. for 48 hours, the expression of GFP was detected under fluorescence microscope. Since the cells, in which baculoviruses replicated, represented fluorescence, the efficiency of recombinant viral expression was determined by counting the cells showing green fluorescence. In the meantime, BacPAK6 viral DNA (Clontech, California, U.S.A.) treated with Bsu36I and 500 ng of pBacPAK_GFP were transferred to Sf21 cells, then the expression of GFP in the Sf21 cells was monitored.

TABLE 3

The expression efficiency of GFP baculoviruses.

| Virus DNA | Bsu36I | gene cassette | GFP positive cell# |
|---|---|---|---|
| BacPAK6 | Yes | pBacPAK8 EGFP | 154 |
| VbacHTS |  | pEntr EGFP | 1752 |
| VbacHTS | yes | pEntr EGFP | 572 |
| VbacHTS His |  | pEntr EGFP | 2236 |
| VbacHTS His | yes | pEntr EGFP | 654 |
| VbacHTS HisGST |  | pEntr EGFP | 1433 |
| VbacHTS HisGST | yes | pEntr EGFP | 475 |

As a result, the efficiency of viral expression is much higher in the method of the present invention compared to the prior art (see Table 3).

Example 8

Detection of the Efficiency of Recombinant Viral Expression

Recombinant viruses expressing GUS were prepared, and the number of plaques expressing GUS genes was counted. In order to accomplish this, firstly, 100 ng of the pEntr_GUS gene cassette containing GUS genes and 200 ng of each of the viral DNA of Bsu36I-treated vBacHTS, vBacHTS_His or vBacHTS_HisGST were reacted in the presence of 4 μl of integrase mixture comprising integrase, exisionase, IHF-α and IHF-β at 25° C. for 6 hours. The resulting mixture was transferred to Sf21 cells together with lipofectin (Life Technologies, Inc., Maryland, U.S.A.) to generate recombinant baculoviruses. Plaque assays were carried out for the viral culture medium. On the other hand, in order to detect productivity of the recombinant viruses, a 4-day viral culture medium was dilated and transferred to insect cells. Subsequently, the cells were incubated for 4 days after adding medium containing 1% low-melting point agarose thereto. The number of plaques expressing GUS genes were counted after 4 days visible from the addition of 100 μl of 0.33% neutral red water solution and 25 μl of X-Gluc (20 mg/ml in DMSO) and afer subsequent dye treatment (see Table 4).

TABLE 4

The efficiency of GUS recombinant viral expression.

| Virus DNA | Bsu36I | gene cassette | Total | Recombinant | rate % |
|---|---|---|---|---|---|
| BacPAK6 | yes | pBacPAK8 EGFP | 46 | 41 | 89% |
| VbacHTS |  | pEntr GUS | 28 | 25 | 89% |
| VbacHTS | yes | pEntr GUS | 57 | 57 | 100% |
| VbacHTS His |  | pEntr GUS | 44 | 36 | 82% |
| VbacHTS His | yes | pEntr GUS | 46 | 45 | 98% |
| VbacHTS HisGST |  | pEntr GUS | 82 | 57 | 70% |
| VbacHTS HisGST | yes | pEntr GUS | 32 | 32 | 100% |
| VbacHTS GFP |  | pEntr GUS | 27 | 22 | 81% |
| VbacHTS GFP | yes | pEntr GUS | 21 | 20 | 95% |

As a result, most of the plaques represented blue color when they were treated with X-Gluc, which supported that the efficiency of GUS viral generation was very high in comparison to the prior art.

Example 9

High-Throughput Preparation of Recombinant Viruses in Multi-Well Plate

Desired recombinant viruses were prepared simultaneously from a multi-well plate. For this purpose, the vBacHTS viral DNA was treated with Bsu36I restriction enzyme. In this study, a GFP gene cassette was employed to confirm the generation of recombinant baculoviruses and gene expression. The GFP gene cassettes were incubated in a 96-deep well plate simultaneously and purified using an automatic device. All the processes were carried out in the multi-well plate. The recombination reaction, insect cell incubation, and viral infection were performed using an 8-channel pipette. About 50 ng of the gene cassette and 200 ng of vBacHTS baculoviral DNA were reacted in the presence of 2 μl of recombinase and 4 μl of buffer at 25° C. for 12 hours. A total of 20 pt of reaction mixture was used in this reaction. In order to detect the insertion of the gene cassette, PCR amplification was performed using primers for polyhedrin locus amplification.

Baculo-Forward primer: 5-actgttttcgtaacagttttg-3 (SEQ. ID No.: 6)

Baculo-Reverse primer: 5-acaacgcacagaatctagc-3 (SEQ. ID No.: 7)

Figure 22:
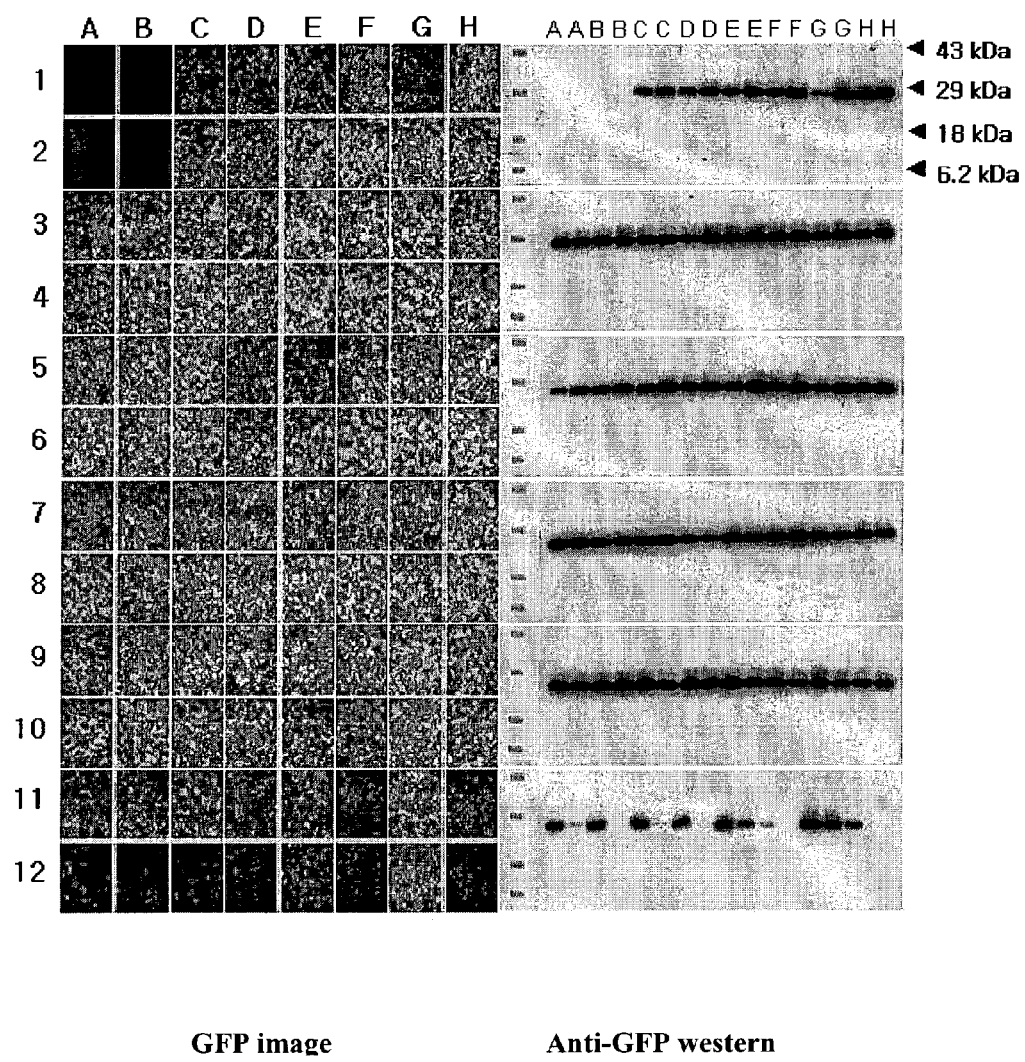
FIG. 22 illustrates a GFP image in multi-well plate and the results of western blot.

As a result, recombinant viral DNA was generated with very high efficiency. Meanwhile, liposome was prepared by mixing 5 μl of the recombinant reaction mixture with 5 μl of 10% lipofectin dilates, which in turn was transfened to 50,000 of Sf21 cells in a 96-well plate (SPL) followed by the incubation of the cells for 4 days. Protein expression was assayed after a 3-day incubation of 50,000 of the Sf21 cells that were infected again with 10 μl of viruses. As for GFP viruses, the expression of green fluorescence was detected under the fluorescence microscope. And, the exhibition of symptoms of GFP viral infection was detected also. The cells were isolated from each of the wells with SDS-PAGE, and the expression of GFP was assayed using GFP-antibody with western blot. With regard to GFP proteins, the measured value showed a similar pattern as detected under the fluorescence microscope (see FIG. 22).

Example 10

Figure 26:
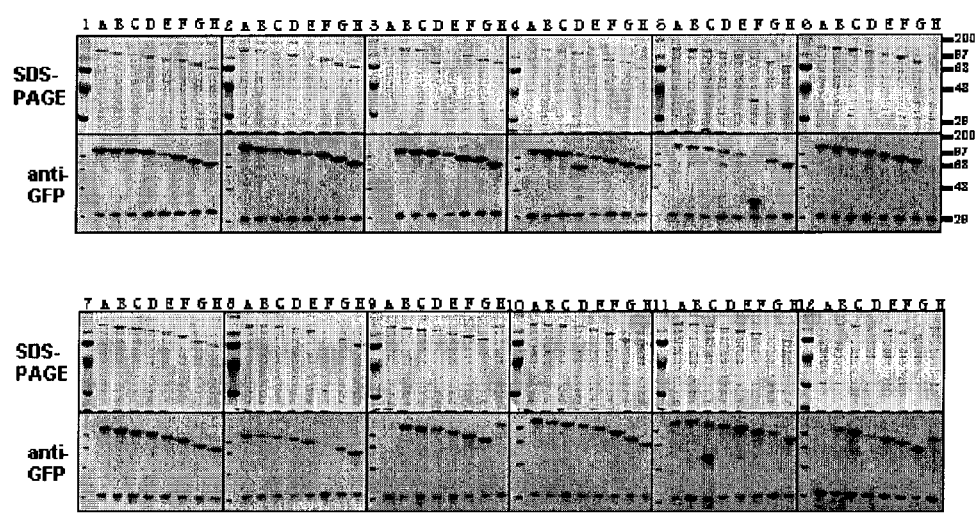
FIG. 26 shows the results of western blot of the expression of GFP-LacZ fusion protein using SDS-PAGE and GFP antibodies.

High-Throughput Preparation and Enzyme Activity Screening of LacZ Gene Mutants in a 96-Well Plate Using GFP Recombinant Baculoviruses In order to prepare desired recombinant baculoviruses (sized about 13.2 kb) from a multi-well plate simultaneously, the vBacHTS_GFP viral DNA was treated with Bsu36I restriction enzyme. Gene cassettes of pEntr_LacZdel were employed in this study. The gene cassettes were prepared in a 96-well plate by PCR cloning of the gene of β-galactosidase from *E. coli* (sized about 3.2 kb), wherein the gene was deleted at the 3'-terminus. More specifically, pEntr_LacZ was prepared by PCR cloning of the gene of LacZ. Afterward, pEntr_LacZ was treated with an ExoIII/S1 deletion kit (#$K_{0421}$) (from Fermentas) to generate pEntr-_LacZdel. All the processes were carried out in a multi-well plate. The recombination reaction, insect cell incubation and viral infection were performed with an 8-channel pipette. 50 ng of gene cassettes and 200 ng of vBacHTS baculoviral DNA was reacted in the presence of 2 μl of recombines and 4 μl of buffer at 25° C. for 12 hours. A total of 20 μl of reaction mixture was used in this reaction. In order to detect the insertion of the gene cassette, PCR amplification was performed using a pair of primers (Seq. ID No. 6 and Seq. ID No. 7) for the amplification of polyhedrin locus. As a result, recombinant viruses were generated at very high efficiency (see FIG. 25). Meanwhile, liposome was prepared by mixing 5 μl of the recombinant reaction mixture and 5 μl of 10% lipofectin dilates, which in turn was transferred to 50,000 of Sf21 cells in a 96-well plate (SPL) followed by incubation of the cells for 4 days (see FIG. 26). In order to assay the expression of GFP fusion proteins, SDS-PAGE analysis and western blotting using GFP antibodies were carried out (see FIG. 26).

Figure 27:
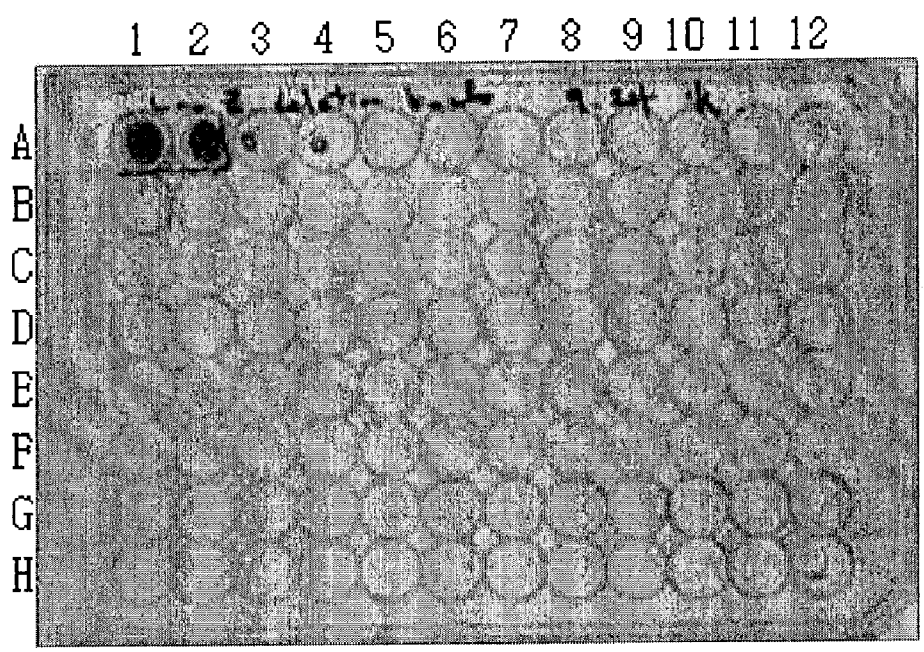
FIG. 27 depicts LacZ enzyme activity in recombinant virus (GFP-LacZ) using X-Gal substrates.

In order to screen the gene activities, 1.5 μl of X-Gal (25 mg/ml in DMSO) of developer of β-galactosidase was added to each well that contained viruses incubated for 3 days after the primary infection. After 12 hrs of reaction, viruses containing β-galactosidase activity were detected in 2 (two) wells (see FIG. 27).

Example 11

High-Throughput Heterologous Gene Expression Using Recombinant Baculoviruses in a 96-Well Plate and the Screening of Enzyme Activity Using the Same

Figure 28:
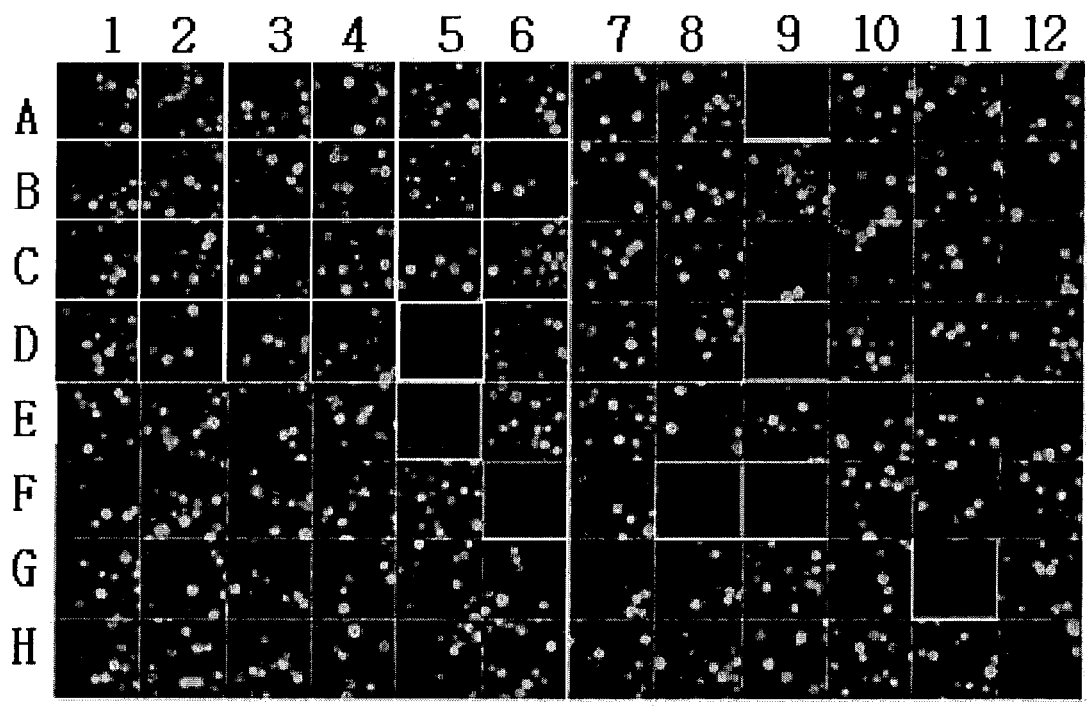
FIG. 28 shows the image of Sf21 cells infected with GFP—YPK baculoviruses from a multi-well plate.
Figure 28:
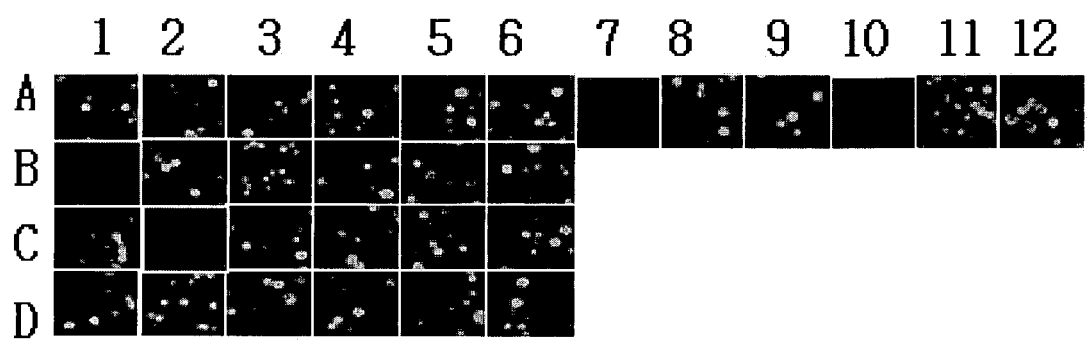

*S. cerevisiae*, which includes 124 protein kinase genes, was employed in this study. PCR amplification and cloning were carried out using gene-specific primers to obtain 112 gene cassettes from the *S. cerevisiae* genome. Recombinant baculoviruses were prepared by the recombination of the gene cassettes and the vBacHTS_GFP vector DNA. The respective recombinant viruses represented particular fluorescence according to the proteins fused to GFP (see FIG. 28). Also, the recombinant baculoviruses having 32 human cDNA were prepared in the same manner.

Figure 29:
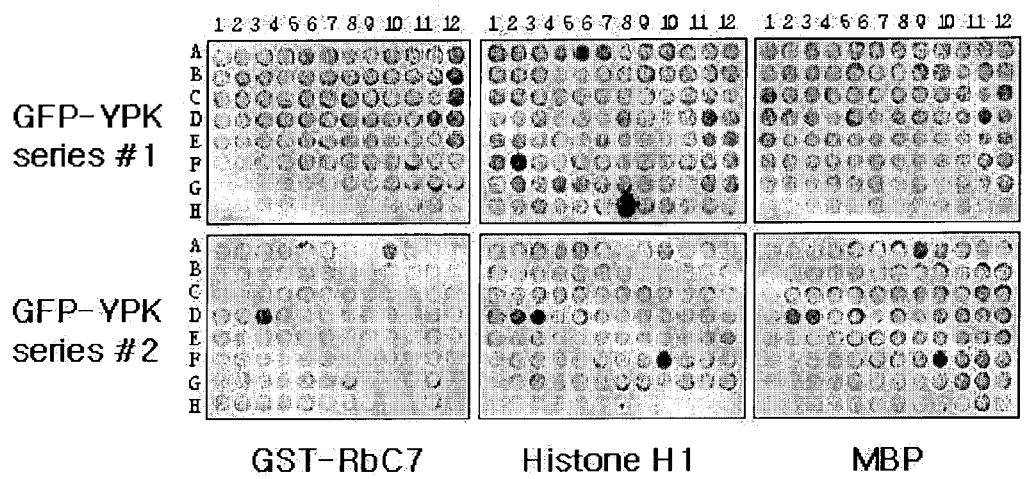
FIG. 29 shows the results of screening protein kinase (Rb, Histone H1, MBP).
Figure 30:
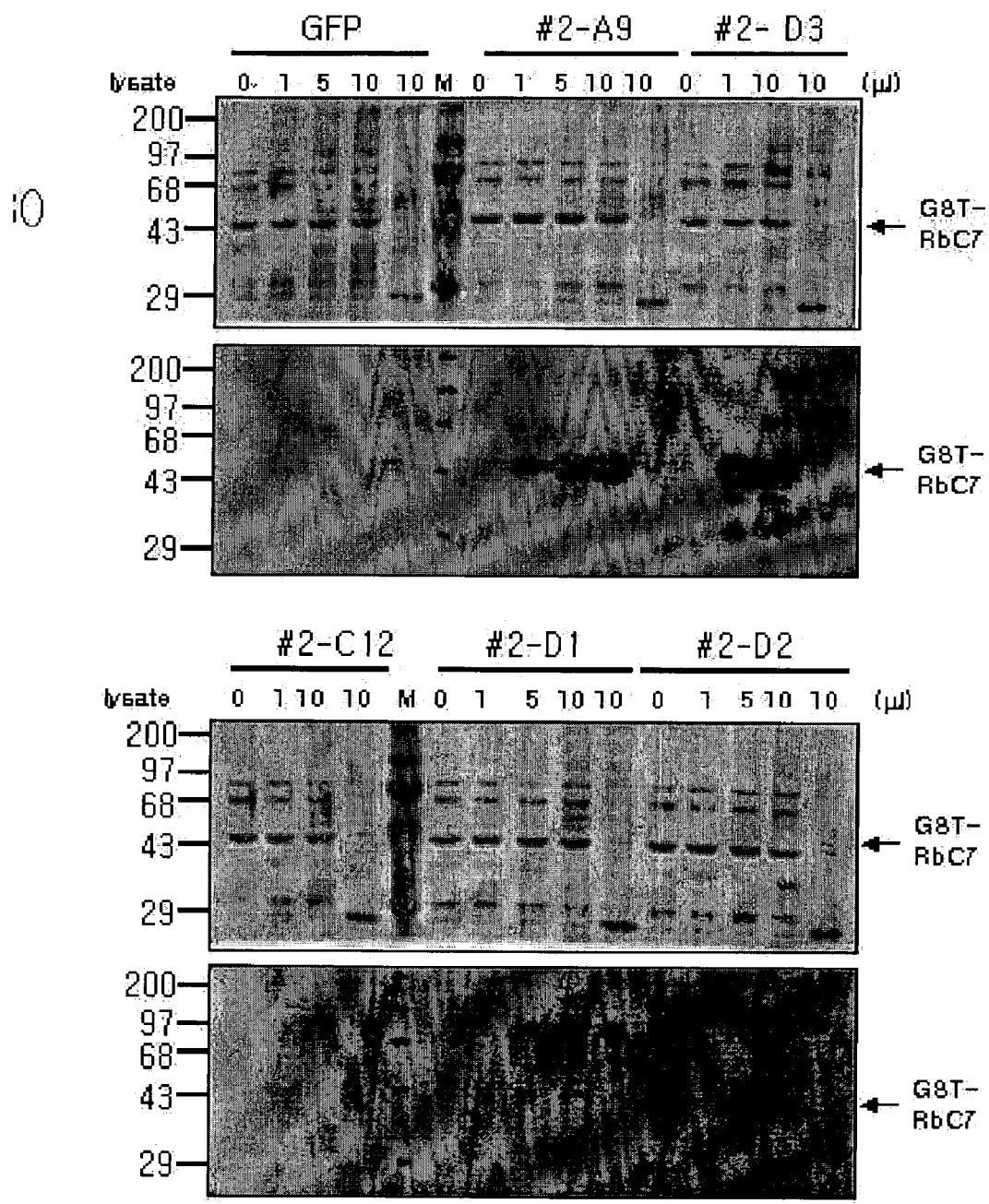
FIG. 30 depicts phosphorylation of Rb (retinoblastoma) protein.
Figure 31:
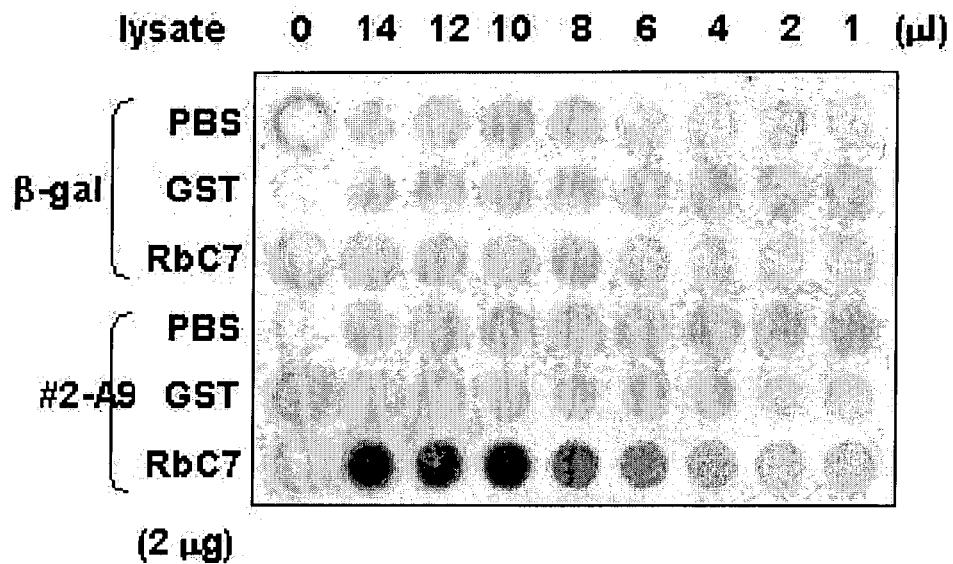
FIG. 31 illustrates phosphorylation of Rb protein by #2-A9 protein kinase.
Figure 31:
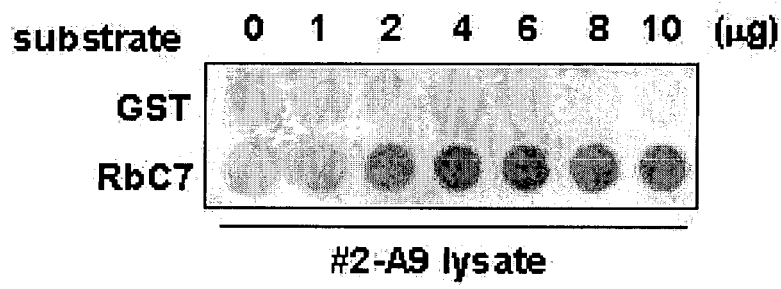
Figure 31:
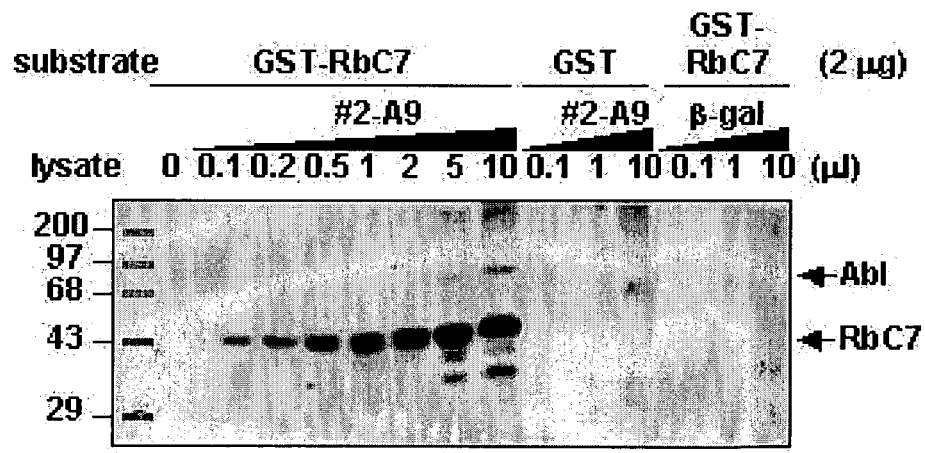

Firstly, cells were infected with these viruses and incubated for 3 days. The cell lysate was generated using a buffer to lyse cells. Viruses, which exhibited protein kinase activities to substrates of Histon H1, myelin basic protein (MBP) and Rb, were screened. 2 μg of protein substrates (histon H1, MBP and Rb) were reacted with 10 μl of cell extracts at 30° C. for 10 minutes, in the presence of 10 μM adenosine triphosphate (ATP), 0.2 uCi of P32-6-labeled ATP (gamma, P32 ATP), and 2 μl of phosphate buffer (200 mM Tris-HCl (pH=8.0), 100 mM of $MgCl_2$, 10 mM of ethylene glycol tetraacetic acid (EGTA) and 10 mM of diothiothreitol (DTT)). After stopping the reaction by adding 120 μl of 1% phosphoric acid solution, the reaction mixture was transferred to a polyvinylidene difluoride (PVDF) membrane (Millipore, Massachusetts, U.S.A., #MAIP-N45). Afterwards, the membrane was washed with detergent (10 mM Tris-HCl (pH-8.0), 1 mM ethylenediamine tetraacetic acid (EDTA) and 150 mM NaCl) four times and dried, which in turn was exposed to phosphoscreen at room temperature. Signals were detected with a Phosphoimager (Molecular Dynamics, California, U.S.A or Fuji, BAS, Japan). As a result, it was observed that protein kinase activities were increased in some viruses (see FIG. 29). Subsequently, SDS-PAGE electophoretic analysis was carried out to confirm the specificity of protein phosphorylation. At that time, the level of Rb protein phosphorylation with regard to the concentration of protein kinase included in cell extracts was detected, while varying the concentrations of cell extracts. As a result, only the cell extracts of the baculoviruses expressing plate#2-D3 protein and plate#2-A9 protein increased Rb protein phosphorylation in a concentration-dependent manner (see FIG. 30). Meanwhile, proteins of plate#2-D1 and plate#2-D2 exhibited very weak phosphorylation activities. And, it was acknowledged that the positive signals from the proteins of plate#2-D1 and plate#2-D2 resulted from auto-phosphorylation activities rather than from Rb protein phosphorylation. Rb protein phosphorylations by plate#2-D3 and plate#2-A9 proteins exhibited a typical protein phosphorylation pattern in that phosphorylation of Rb protein was dependent on the concentration of the substrate and the enzyme (FIG. 31). Thus, it is possible to find out new useful proteins from baculoviral libraries obtained from the high-throughput system according to the present invention.

Example 12

The Preparation of pBacHTS2 and pBacHTS2 GFP

Baculoviral transfer vector of pBacHTS2 was prepared in order to generate vBacHTS2 viruses (SEQ. ID No. 8: the sequence of its polyhedrin locus) that can replicate and can be applied to a recombination reaction in vitro. The pBacHTS2 had a bacterial artificial chromosome (BAC) vector originated the replication origin and chloramphenichol resistance gene (CmR) at the Bsu36I restriction enzyme recognition site located between the attR1 site and the attR2 site thereof. Thus, it was the type of BAC vector that can replicate in bacteria. Replacing the BAC vector originated replication origin and CmR with the desired gene cassette generated vBacHTS viruses in vitro.

In order to prepare pBacHTS2, firstly, 6.5 kb of DNA fragment containing the BAC vector replication origin and CmR was generated using pBACe3.6 (Genbank: U80929) as a template. Then, PCR amplification was carried out using 10 μmol of a pair of sequences having Bsu36I recognition sequences, 200 μM of dNTPs and 2.5 μl of PfuTurbo polymerase (Stratagene) with PCR cycler (Applied Biosystems, California, U.S.A., Gene Amp PCR System 2700). A total of 50 μl of reaction mixture was used. PCR was carried out for 20 cycles (DNA denaturation at 95° C., 30 seconds, DNA extension at 60° C., 30 seconds, DNA amplification at 72° C., 7 minutes). PCR products of 6.5 kb of DNA fragment and vBacHTS vector were digested by Bsu36I, and were reacted in the presence of T4 ligase at 16° C. overnight. *E. coli* (DH5a) was transformed using the resulting mixture, which in turn was incubated with Cland Amp medium (for selection) to produce pBacHTS2. Likewise, Bsu36I treated PCR products of 6.5 kb of DNA fragment were inserted to Bsu36I site of the pBacHTS_GFP vector so as to obtain pBacHTS2_GFP vector.

Example 13

Preparation of Viruses Having Site-Specific Recombination Sites

Figure 16:
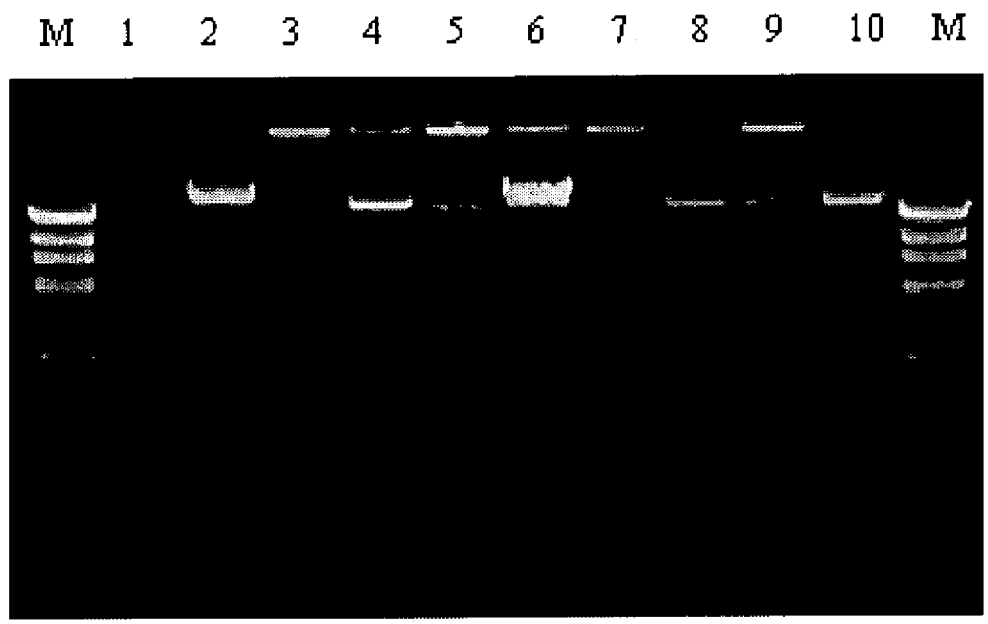
FIG. 16 illustrates agarose gel electrophoretic analysis of vBacHTS viral DNA and bBacHTS2 viral DNA.
Figure 17:
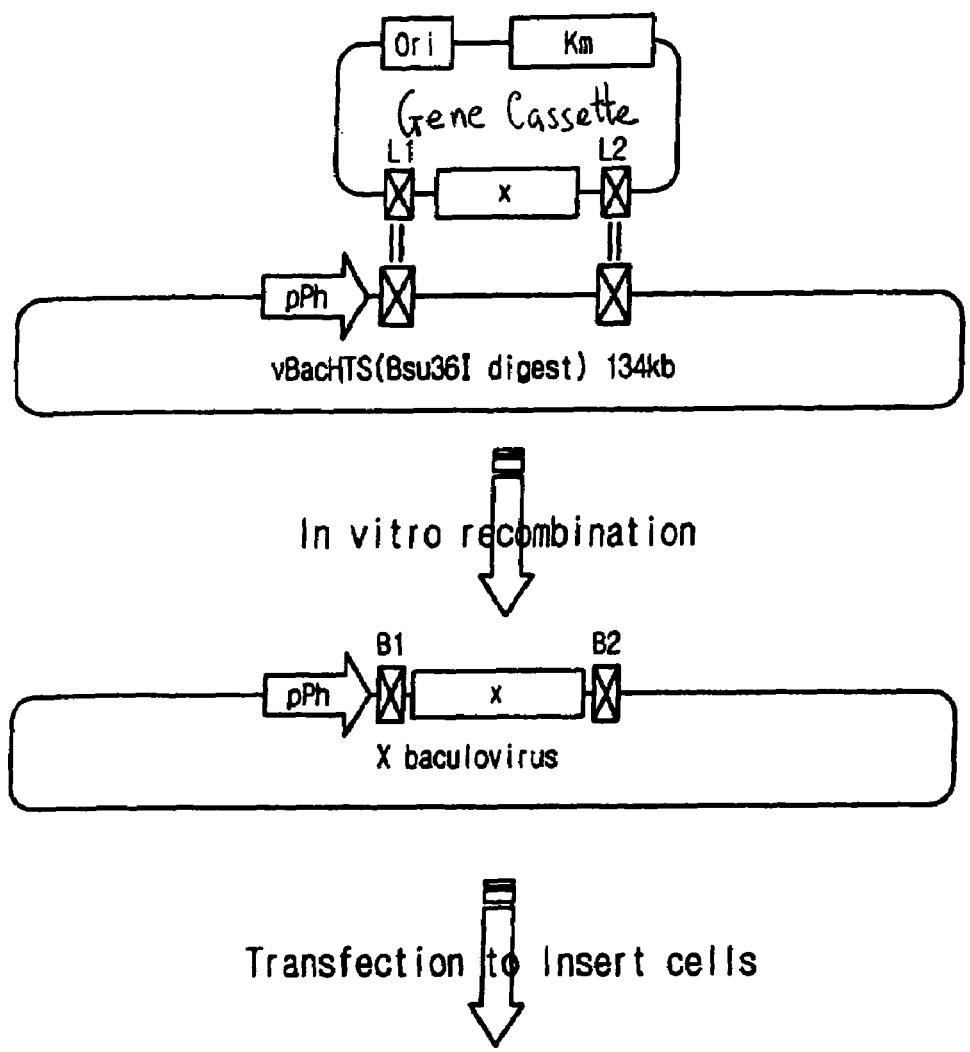
FIG. 17 illustrates procedures for the preparation of desired recombinant viruses using vBacHTS and a gene cassette.

Baculoviruses were prepared using homologous recombination, which replicated in bacteria. Briefly, the homologous recombination was induced in St21 cells by transferring a mixture of pBacHTS2 plasmid, Bsu36I digested BacPAK6 DNA and Lipofectin (Life Technologies, Inc., Maryland, U.S.A.). The infected cells were incubated at 27° C. for 4 days, and were transferred to 5×10⁶ of Sf21 cells (in 100 mm dish). Thereby, high titer of viruses was obtained. Then, precipitates of viral particles were produced by centrifugation after adding 2 ml of 50% PEG6000 to the cell culture medium. Next, proteinase K was added to the mixture at 42° C. and left alone for 2 hours to dismantle the viral envelope. The viral lysate was extracted twice using the same amount of phenol/chloroform, and ethanol was added thereto. Thereby, precipitated and purified vBacHTS2 viral DNA (SEQ. ID No. 8: the sequence of its polyhedrin locus) were obtained. Then, cell lines (Life Technologies, Inc., Maryland, U.S.A.) were transformed with the purified DNA using MicroPulser (Bio-Rad, California, U.S.A.), which are in turn incubated in Cm medium to form a bacterial colony. The bacteria were incubated in 1 liter of 2xYT medium (10 g of Yeast extract powder, 16 g of tryptone, 5 g of NaCl within per liter), then DNA was purified and named as bBacHTS2 (FIG. 16). Thus, according to this method, it is possible to reduce the required time-period and cost significantly, since the viral DNA can be obtained from bacterial culture without the need of incubation in insect cells. Purified 10 μg of DNA was digested with 50 units of Bsu36I at 37° C. for 5 hours, which in turn was heat treated at 80° C. for 20 minutes to inactivate Bsu36I enzyme. Likewise, vBacHTS2_GFP (SEQ. ID No. 9) was prepared from pBacHTS2_GFP vector by homologous recombination; and then was transferred to DH10B by electrophoration. The DNA was purified and named as bBacHTS2_GFP (see FIG. 16).

Example 14

Preparation of the Desired Recombinant Viruses Using vBacHTS2 and vBacHTS2 GFP DNA Generated from Bacteria 50 ng of the pEntr_GFP and the pEntr_GUS gene cassettes were reacted with 200 ng of Bsu36I treated vBacHTS2 viral DNA in the presence of 1 μl of integrase mixture in vitro at 25° C. for 12 hours. The same reaction was carried out except for the use of the pEntr_GUS gene cassette in place of the pEntr_GFP gene cassette. PCR was performed as disclosed in the Examples mentioned above. PCR amplification was carried out using the reaction mixture, as templates, and a pair of primers amplifying the viral polyhedrin locus to confirm whether a recombination reaction occurred. A total of 20 cycles of PCR were carried out using each of 10 pmole of the primers and 1 tube of Bioneer premix kit, in which one cycle of PCR was performed at 95° C. for 30 seconds, 50° C. for 30 seconds and 72° C. for 3 minutes. After completing PCR reaction, electrophoresis was carried out for the PCR products on 1% agarose gel to confirm efficient performance of recombination. The gene cassette reaction mixture was transferred to Sf21 cells together with 5 μl of Lipofectin (Life Technologies, Inc., Maryland, U.S.A.) so as to obtain baculoviruses.

Green fluorescence was observed in insect cells, after 2 days from transferring GFP gene cassette reaction mixture thereto. In addition, most of the cells represented green fluorescence after 4 days from transfer (see FIG. 25). Sf21 cells were infected again with the viral culture medium to confirm green fluorescence and the symptoms of infection. Likewise, pEntr_GUS gene cassette was reacted with Bsu36I treated vBacHTS2 DNA at 25° C. for 12 hours. Then, the obtained reaction mixture was transferred to Sf21 cells and was incubated at 27° C. for 4 days. When 6 μl of X-Gluc (20 mg/ml in DMSO) was added to incubated cells, all the culture medium represented a strong blue color, which supported not only the expression of GUS genes but also efficient generation of recombinant viruses containing GUS genes.

---

What is claimed is:

1. A method for preparing expressive circular recombinant viral vectors, comprising:
   i) providing a plurality of linearized viral DNA fragments wherein each fragment contains at least two site-specific recombination sites and at least one restriction enzyme recognition site;
   ii) providing a plurality of viral vector carriers wherein each viral vector carrier contains a gene cassette having a desired genomic material with a desired nucleic acid sequence flanked with at least two site-specific sites for homologous recombination with the linearized DNA fragments at the two site-specific recombination sites; and
   iii) reacting the linearized viral DNA fragments and the viral vector carriers to create homologous recombinations in vitro wherein a plurality of recombinant viral vectors carrying the desired genomic material is formed in vitro therefrom;
   iv) wherein non-recombined linearized viral DNA fragments, non-recombined viral vector carriers, and non-linearized viral DNA do not express a gene for a protein responsible for viral replication and viral particle formation.

2. The method for preparing expressive circular recombinant viral vectors as claimed in claim 1, wherein one or more viral DNA fragments are digested with restriction enzymes at one or more sites to generate the linearized viral DNA fragments.

3. The method for preparing expressive circular recombinant viral vectors as claimed in claim 1, wherein the recombinant viral vectors are obtained from the group consisting of baculovirus, poliomavirus, papillomavirus, and hepatitis B virus (HBV).

4. The method for preparing expressive circular recombinant viral vectors as claimed in claim 2, wherein said one or more sites comprise the nucleotide sequence of CCTNAGG.

5. A method of preparing recombinant viruses having circular genomic DNA, comprising:
   i) providing a plurality of linearized viral DNA fragments wherein each fragment contains at least two site-specific recombination sites and at least one restriction enzyme recognition site;
   ii) providing a plurality of viral vector carriers wherein each viral vector carrier contains a gene cassette having a desired genomic material with a desired nucleic acid sequence flanked with at least two site-specific sites for homologous recombination with the linearized DNA fragments at the two site-specific recombination sites; and
   iii) reacting the linearized viral DNA fragments and the viral vector carriers to create homologous recombinations in vitro to produce a reaction mixture including expressive circular recombinant viral vectors carrying the desired genomic material formed in vitro therefrom;
   iv) wherein non-recombined linearized viral DNA fragments, non-recombined viral vector carriers and non-linearized viral DNA do not express a gene for a protein responsible for viral replication and viral particle formation; and
   v) transferring the reaction mixture to host cells in a multi-well plate.

6. The method of preparing recombinant viruses having circular genomic DNA as claimed in claim 5, wherein the transfer of the reaction mixture to host cells is carried out without a need for a selection process to isolate the circular genomic DNA.

7. The method of preparing recombinant viruses having circular genomic DNA as claimed in claim 5, wherein viral genomic DNA of i) are digested with a restriction enzyme at one or more sites to generate the linearized viral DNA fragments.

8. The method of preparing recombinant viruses having circular genomic DNA as claimed in claim 5, wherein the recombinant viral vectors are obtained from the group consisting of baculovirus, poliomavirus, papillomavirus, and hepatitis B virus (HBV).

9. The method of preparing recombinant viruses having circular genomic DNA as claimed in claim 7, wherein said one or more sites comprise the nucleotide sequence of CCTNAGG.

* * * * *